US007803835B2

(12) United States Patent  
Gopalsamy et al.

(10) Patent No.: US 7,803,835 B2
(45) Date of Patent: Sep. 28, 2010

(54) SUBSTITUTED ACETIC ACID DERIVATIVES

(75) Inventors: Ariamala Gopalsamy, Mahwah, NJ (US); Scott Lee Kincaid, Middletown, NY (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 12/168,499

(22) Filed: Jul. 7, 2008

(65) Prior Publication Data

US 2008/0312308 A1 Dec. 18, 2008

Related U.S. Application Data

(62) Division of application No. 10/947,711, filed on Sep. 23, 2004, now Pat. No. 7,411,083.

(60) Provisional application No. 60/505,913, filed on Sep. 25, 2003.

(51) Int. Cl.
*A61K 31/403* (2006.01)
*A61K 31/195* (2006.01)
*C07D 209/04* (2006.01)
*C07C 59/74* (2006.01)

(52) U.S. Cl. .................. 514/419; 514/567; 548/491; 562/469

(58) Field of Classification Search .............. 514/419, 514/567; 548/491; 562/469
See application file for complete search history.

(56) References Cited

U.S. PATENT DOCUMENTS

| 3,026,325 | A | 3/1962 | Heinzelman et al. ......... 548/496 |
| 3,476,770 | A | 11/1969 | Scherrer ...................... 548/494 |
| 3,557,142 | A | 1/1971 | Bell ............................ 548/516 |
| 3,843,683 | A | 10/1974 | Bell ............................ 548/493 |
| 4,478,819 | A | 10/1984 | Hercelin et al. ............. 424/457 |
| 4,736,043 | A | 4/1988 | Michel et al. ................ 548/492 |
| 4,851,406 | A | 7/1989 | Martens et al. ........ 514/217.04 |
| 5,164,372 | A | 11/1992 | Matsuo et al. ................ 514/19 |
| 5,254,577 | A | 10/1993 | Carlson et al. .............. 514/376 |
| 5,420,289 | A | 5/1995 | Musser et al. .............. 548/159 |
| 5,482,960 | A | 1/1996 | Berryman .................... 514/414 |
| 5,502,187 | A | 3/1996 | Ayer et al. ................... 544/117 |
| 5,541,343 | A | 7/1996 | Himmelsbach et al. ..... 514/424 |
| 5,599,663 | A | 2/1997 | Vaughan ........................ 435/6 |
| 5,612,360 | A | 3/1997 | Boyd et al. .................. 514/381 |
| 5,840,758 | A | 11/1998 | Brooks et al. ............... 514/564 |
| 5,859,044 | A | 1/1999 | Dow et al. ................... 514/419 |
| 6,048,875 | A | 4/2000 | De Nanteuil et al. ........ 514/314 |
| 6,110,963 | A | 8/2000 | Malamas ..................... 514/443 |
| 6,166,069 | A | 12/2000 | Malamas et al. ............. 514/469 |
| 6,232,322 | B1 | 5/2001 | Malamas et al. ............. 514/303 |
| 6,251,936 | B1 | 6/2001 | Wrobel et al. ............... 514/443 |
| 6,302,837 | B1 | 10/2001 | De Nanteuil et al. ........ 514/337 |
| 6,479,524 | B1 | 11/2002 | Priepke et al. .............. 514/352 |
| 6,599,929 | B2 | 7/2003 | Cho et al. .................... 514/415 |
| 6,787,556 | B1 | 9/2004 | Hargreaves et al. ......... 514/311 |
| 6,800,645 | B1 | 10/2004 | Cox et al. .................... 514/314 |
| 6,800,654 | B2 | 10/2004 | Mayer et al. ................ 514/381 |
| 6,844,358 | B2 | 1/2005 | Malamas et al. ............. 514/336 |
| 2003/0013732 | A1 | 1/2003 | Elokdah ...................... 514/301 |
| 2003/0018067 | A1 | 1/2003 | Elokdah et al. .............. 514/469 |
| 2003/0060497 | A1 | 3/2003 | Gerlach et al. .............. 514/414 |
| 2003/0125371 | A1 | 7/2003 | Elokdah et al. .............. 514/419 |
| 2004/0116488 | A1 | 6/2004 | Jennings et al. ............. 514/374 |
| 2004/0116504 | A1 | 6/2004 | Elokdah et al. .............. 514/419 |
| 2004/0122070 | A1 | 6/2004 | Jennings ..................... 514/374 |
| 2004/0138283 | A1 | 7/2004 | Jennings et al. ............. 514/414 |
| 2004/0204417 | A1 | 10/2004 | Perez et al. .................. 514/249 |
| 2005/0070584 | A1 | 3/2005 | Havran et al. ............... 514/357 |
| 2005/0070585 | A1 | 3/2005 | Elokdah et al. .............. 514/364 |
| 2005/0070587 | A1 | 3/2005 | Elokdah et al. .............. 514/381 |
| 2005/0070592 | A1 | 3/2005 | Gundersen .................. 514/415 |
| 2005/0096377 | A1 | 5/2005 | Hu .............................. 514/419 |
| 2005/0113428 | A1 | 5/2005 | Gopalsamy et al. ......... 514/364 |
| 2005/0113436 | A1 | 5/2005 | Elokdah et al. .............. 514/411 |
| 2005/0113438 | A1 | 5/2005 | Hu et al. ..................... 514/414 |
| 2005/0113439 | A1 | 5/2005 | Hu .............................. 514/414 |
| 2005/0119296 | A1 | 6/2005 | Elokdah et al. .............. 514/300 |
| 2005/0119326 | A1 | 6/2005 | Havran et al. ............... 514/414 |
| 2005/0119327 | A1 | 6/2005 | Hu .............................. 514/414 |
| 2005/0215626 | A1 | 9/2005 | Havran et al. ............... 514/469 |
| 2006/0020003 | A1 | 1/2006 | Commons et al. ........... 514/374 |
| 2006/0052348 | A1 | 3/2006 | Commons et al. ............. 514/92 |
| 2006/0052349 | A1 | 3/2006 | Commons et al. ............. 514/95 |
| 2006/0052420 | A1 | 3/2006 | Commons ................... 514/340 |

FOREIGN PATENT DOCUMENTS

| DE | 2455432 A1 | 6/1975 |
| DE | 3147276 A1 | 6/1983 |
| DE | 43 38 770 A1 | 5/1995 |

(Continued)

OTHER PUBLICATIONS van Dijk et al. "Oxime Ether Derivatives, a New Class of Nonsteroidal Antiinflammatory Compounds" Journal of Medicinal Chemistry, 1977, vol. 20, No. 9, pp. 1199-1206.*

(Continued)

*Primary Examiner*—Joseph R Kosack
(74) *Attorney, Agent, or Firm*—Mabel Ng

(57) ABSTRACT

The present invention relates generally to substituted acetic acid derivatives and methods of using them.

16 Claims, No Drawings

FOREIGN PATENT DOCUMENTS

| | | |
|---|---|---|
| DE | 19543639 A1 | 5/1997 |
| DE | 19753522 | 6/1999 |
| EP | 0 077 854 A1 | 5/1983 |
| EP | 0 352 781 A2 | 1/1990 |
| EP | 0 416 609 A2 | 3/1991 |
| EP | 0 508 723 A1 | 10/1992 |
| EP | 0 512 570 A1 | 11/1992 |
| EP | 0 540 956 A1 | 5/1993 |
| EP | 0 655 439 A2 | 5/1995 |
| EP | 0 759 434 A1 | 2/1997 |
| EP | 0 819 686 A1 | 1/1998 |
| EP | 0 822 185 A1 | 2/1998 |
| EP | 0 955 299 A1 | 11/1999 |
| EP | 1 092 716 | 4/2001 |
| EP | 1 156 045 A1 | 11/2001 |
| FR | 2 244 499 A1 | 4/1975 |
| FR | 2 777 886 A1 | 10/1999 |
| FR | 2 799 756 A1 | 4/2001 |
| GB | 1 321 433 | 6/1973 |
| JP | 2004-256443 | 9/2004 |
| WO | 94/13637 A1 | 6/1994 |
| WO | 94/14434 A1 | 7/1994 |
| WO | 94/26738 A1 | 11/1994 |
| WO | 95/10513 A1 | 4/1995 |
| WO | 96/06840 A1 | 3/1996 |
| WO | 96/21656 A1 | 7/1996 |
| WO | 96/26207 A1 | 8/1996 |
| WO | 96/32379 A1 | 10/1996 |
| WO | 97/09308 A1 | 3/1997 |
| WO | 97/43260 A1 | 11/1997 |
| WO | 97/48697 A1 | 12/1997 |
| WO | 98/08818 A1 | 3/1998 |
| WO | 99/28297 A1 | 6/1999 |
| WO | 99/43651 A2 | 9/1999 |
| WO | 99/43654 A2 | 9/1999 |
| WO | 99/43672 A1 | 9/1999 |
| WO | 99/46260 A1 | 9/1999 |
| WO | 99/50268 A1 | 10/1999 |
| WO | 99/58519 A1 | 11/1999 |
| WO | 99/61435 A1 | 12/1999 |
| WO | 00/32180 A2 | 6/2000 |
| WO | 00/35919 A1 | 6/2000 |
| WO | WO 0035859 A1 | 6/2000 |
| WO | 00/46195 A1 | 8/2000 |
| WO | 00/46197 A1 | 8/2000 |
| WO | 00/64876 A1 | 11/2000 |
| WO | 00/64888 A1 | 11/2000 |
| WO | 01/12187 A2 | 2/2001 |
| WO | 02/030895 A1 | 4/2002 |
| WO | 02/072549 A1 | 9/2002 |
| WO | 03/000253 A1 | 1/2003 |
| WO | 03/031409 A1 | 4/2003 |
| WO | 03/068742 A1 | 8/2003 |
| WO | 03/087087 A2 | 10/2003 |
| WO | 2004/052854 A2 | 6/2004 |

OTHER PUBLICATIONS

Krishnamurti, C. et al., "Plasminogen Activator Inhibitor: A Regulator of Ancrod-Induced Fibrin Deposition in Rabbits," *Blood*, 69(3): 798-803 (Mar. 1987).

Reilly, C. et al., "Both Circulating and Clot-Bound Plasminogen Activator-1 Inhibit Endogenous Fibrinolysis in the Rat," *Arteriosclerosis and Thrombosis*, 11(5): 1276-1286 (Sep./Oct. 1991).

Carmeliet, P. et al., "Plasminogen Activator Inhibitor -1 Gene-deficient Mice," *Journal of Clinical Investigation*, 92: 2756-2760 (Dec. 1993).

Rocha, E. et al., "The Relationship Between Impaired Fibrinolysis and Coronary Heart Disease," *Fibrinolysis*, 8: 294-303 (1994).

Aznar, J. et al., "Role of Plasminogen Activator Inhibitor Type 1 in the Pathogenesis of Coronary Artery Diseases," *Haemostasis* 24: 243-251 (1994).

Biemond, B. J. et al., "Thrombolysis and Reocclusion in Experimental Jugular Vein and Coronary Artery Thrombosis," *Circulation*, 91: 1175-1181 (1995).

Levi, M. et al., "Inhibition of Plasminogen Activator Inhibitor-1 Activity Results in Promotion of Endogenous Thrombolysis and Inhibition of Thrombus Experimental Thrombosis," *Circulation* 85:305-312 (1992).

Nordt, T. K. et al., "Differential Regulation by Troglitazone of Plasminogen Activator Inhibitor Type 1 in Human Hepatic and Vascular Cells," *Journal of Clinical Endocrinology and Metabolism*, 85(4):1563-1568 (2000).

Daci, E. et al., "Mice Lacking the Plasminogen Activator Inhibitor 1 are Protected from Trabecular Bone Loss Induced by Estrogen Deficiency," *Journal of Bone Mineral Research*, 15(8):1510-1516 (Nov. 8, 2000).

Schneiderman J. et al., "Increased type 1 plasminogen activator inhibitor gene expression in atherosclerotic human arteries," *Proc. Natl Acad Sci* 89: 6998-7002 (Aug. 1992).

Juhan-Vague, I. et al., "Deficient t-PA Release and Elevated PA Inhibitor Levels in Patients with Spontaneous or Recurrent Deep Venous Thrombosis," *Thromb Haemost* 57: 67-72 (1987).

Juhan-Vague, I. et. al., "PAI-1, Obesity, Insulin Resistance and Risk of Cardiovascular Events," *Thromb Haemost* 78: 565-660 (1997).

Hamsten, A. et. al., "Plasminogen Activator Inhibitor in Plasma: Risk Factor For Recurrent Myocardial Infarction," *Lancet* 2: 3-9 (Jul. 4, 1987).

Siemens, H. J. et. al., "Course of Molecular Hemostatic Markers During and After Different Surgical Procedures," *J Clin Anesthesia* 11: 622-629 (Dec. 1999).

Koh, K. et. al., "Effects of Hormone-Replacement Therapy on Fibrinolysis in Postmenopausal Women," *N Engl J Med* 336(10): 683-690 (Mar. 6, 1997).

Yoshikawa, H. et al., "Benzaldehyde O-Alkyloximes as New Plant Growth Regulators," *BioSci. Biotechnol. Biochem.*, 62(5), pp. 996-997, 1998.

Yoshikawa, H. et al., "Synthesis and Biological Activity of Benzaldehyde o-Alkyloximes as Abscisic Acid Mimics (Part I)," *BioSci. Biotechnol. Biochem.*, 56(2), pp. 256-260, 1992.

Van Dijk, J. et al., "Oxime ether derivatives, a new class of nonsteroidal antiinflammatory compounds," *J Med Chem*, 20(9), pp. 1199-1206 (Sep. 1977).

Ley, J. P. et al., "Hydroxy- or Methoxy-Substituted Benzaldoximes and Benzaldehyde-*O*-alkyloximes as Tyrosinase Inhibitors," *Bioorganic & Medicinal Chemistry*, 2001, 9:1879-1885.

Aggarwal et al., "A catalytic antibody programmed for torsional activation of amide bond hydrolysis," *Chemistry—A European Journal*, Jan. 25, 2003, 9(13):3132-3142.

Richardson et al., "Aminooxyacetic acid Derivatives," *Journal of Medicinal Chemistry*, 1964, 7:824-826.

Chemical Abstracts Service, Columbus, Ohio, US; 1996, Benedetti. F. et al., "Anti-Sulfonamide antibodies catalyze the hydrolysis of a heterocyclic amide," retrieved from STN database accession No. 1996:402975 abstract & *Chemical Commications*, 1996, 12:1417-1418.

Chemical Abstracts Service, Columbus, Ohio, US; 1995, Sheppard, G. S. et al., "Synthesis and evaluation of water soluble indole pyrrolothiazole PAF antagonists," retrieved from STN database accession No. 1995:1002157 abstract & *Bioorganic & Medicinal Chemistry Letters*, 1995, 5(23):2913-18.

Chemical Abstracts Service, Columbus, Ohio, US; 1989, Takalo, H.et al., "Preparation of complexing compounds containing two 2,6-bis N, N-bis(carboxymethyl)aminomethyl)]-4-ethynylpyridine subunits," retrieved from STN database accession No. 1989:477814, abstract & *Acta Chemica Scandinavica, Series B: Organic Chemistry and Biochemistry*, 1988, B42(10):662-665.

Chemical Abstracts Service, Columbus, Ohio, US; 1979, Forrester, A. R. et al., "Iminyls. Part 2. Intramolecular aromatic substitution by iminyls. A new route to phenanthridines," retrieved from STN database accession No. 1979:491472 abstract & *Journal of the Chemical Society, Perkin Transactions 1: Organic and Bio-Organic Chemistry*, 1979, (1972-1999)(3):612-615.

Chemical Abstracts Service, Columbus, Ohio, US; 1978, Forrester, A. R. et al., "Fragmentation of oxyalkyl radicals: a new general route to nitrogen radicals," retrieved from STN database accession No. 1978:104807 abstract & *Tetrahedron Letters*, 1977, 40:3601-3604.

Chemical Abstracts Service, Columbus, Ohio, US; 1977, Van Dijk, J.. et al., "Oxime ether derivatives, a new class of nonsteroidal anti-inflammatory compounds," retrieved from STN database accession No. 1977:478244 abstract & *J Medicinal Chemistry*, 1977, 20(9):1199-1206.

Chemical Abstracts Service, Columbus, Ohio, US; 1977, Georgiadis, M. P., "Novel carboxylates: aminooxyacetic acid derivatives," retrieved from STN database accession No. 1977:189585, abstract & *Chimika Chronika*, 1976, 5(4):287-294.

Chemical Abstracts Service, Columbus, Ohio, US; 1975, Forrester, A. R.. et al., "New chemistry of iminyl radicals," retrieved from STN database accession No. 1975:457707, abstract & *Journal of the Chemical Society, Chemical Communications*, 1975, 8:291-292.

Database Beilstein, Feb. 2, 1997, Database Accession No. BRN: 7546867 & Benedetti et al., "1-(toluene-4-sulfonyl)-1H-indol-3-ylmethyleneaminooxy]acetic acid," *J Chem Soc Chem Commun*, 1996, 12:1417-1418.

Aggarwal et al., "A catalytic antibody programmed for torsional activation of amide bond hydrolysis," *Chem. Eur. J.*, Jan. 25, 2003, 9(13), 3132-3142.

Ballantine, J. A., "The Chemistry of Bacteria," *Journal of the Chemical Society Abstracts*, 1957, 2222-2227.

Charlton, Peter, "The status of plasminogen activator inhibitor-1 as a therapeutic target," *Expert Opinion On Investigational Drugs*, May 1997, 6(5), 539-554.

Crandall, D. L. et al., "Characterization and comparative evaluation of a structurally unique PAI-1 inhibitor exhibiting oral in-vivo efficacy," *Journal of Thrombosis and Haemostasis*, Mar. 17, 2004, 2, 1422-1428.

Da Settimo, A. et al., "Reaction of indole derivatives with bromine, substitution, oxidation, and dimerization," *J Org Chem*, 1970, 35(8):2546-2551.

Delgado et al., Journal of Organic Chemistry (1993), 58(10), pp. 2862-2866.

Dillard R. D. et al., "Indole Inhibitors of Human Nonpancreatic Secretory Phospholipase $A_2$ 1. Indole-3-Acetamides", *Journal of Medicinal Chemistry*, American Chemical Society, 39(26), 5119-5136, 1996.

Guzzo, P.R. et al., "Synthesis of a conformationally constrained threonin-valine dipeptide mimetic: design of a potential inhibitor of plasminogen activator inhibitor-1," *Tetrahedron Letters*, 2002 43(1), 41-43.

Hipskind, P. A. et al., "Potent and selective 1,2,3-trisubstituted indole NPY Y-1 antagonists," *J Med Chem*, 1997, 40(23), 3712-3714.

Julia et al., CA 57:49169, 1962.

Malamas, M. S. et al., "Antihyperglycemic activity of new 1,2,4-oxadiazolidine-3,5-diones," *Eur. J. Med. Chem.*, 2001, 36, 31-42.

Malamas, M.S. et al. "Novel benzofuran and benzothiophene biphenyls as inhibitors of protein tyrosine phosphatase 1B with antihyperglycemic properties," *Journal of Medicinal Chemistry*, Apr. 6, 2000, 43(7), 1293-1310.

Moody et al., CA 120:298300, 1994.

Shengeliya, M. S. et al., "N-Glycosides of 5-amino-2-(ethoxycarbonyl)indole," *Zhurnal Organicheskoi Khimii*, 1986, 22(9), 1868-1873.

\* cited by examiner

SUBSTITUTED ACETIC ACID DERIVATIVES

CROSS-REFERENCE TO RELATED APPLICATIONS

This is a divisional of copending application Ser. Nos. 10/974,711 filed on Sep. 23, 2004, and 60/505,913 filed Sep. 25, 2003 the entire disclosure of which is hereby incorporated by reference.

BACKGROUND

The present invention relates generally to substituted acetic acid derivatives and methods of using them.

The serine protease inhibitor PAI-1 is one of the primary inhibitors of the fibrinolytic system. The fibrinolytic system includes the proenzyme plasminogen, which is converted to the active enzyme, plasmin, by one of two tissue type plasminogen activators, t-PA or u-PA. PAI-1 is the principal physiological inhibitor of t-PA and u-PA. One of plasmin's main responsibilities in the fibrinolytic system is to digest fibrin at the site of vascular injury. The fibrinolytic system, however, is not only responsible for the removal of fibrin from circulation but is also involved in several other biological processes including ovulation, embryogenesis, intima proliferation, angiogenesis, tumorigenesis, and atherosclerosis.

Elevated levels of PAI-1 have been associated with a variety of diseases and conditions including those associated with impairment of the fibrinolytic system. For example, elevated levels of PAI-1 have been implicated in thrombotic diseases, e.g., diseases characterized by formation of a thrombus that obstructs vascular blood flow locally or detaches and embolizes to occlude blood flow downstream. (Krishnamurti, *Blood*, 69, 798 (1987); Reilly, Arteriosclerosis and Thrombosis, 11, 1276 (1991); Carmeliet, *Journal of Clinical Investigation*, 92, 2756 (1993), Rocha, *Fibrinolysis*, 8, 294, 1994; Aznar, *Haemostasis* 24, 243 (1994)). Antibody neutralization of PAI-1 activity resulted in promotion of endogenous thrombolysis and reperfusion (Biemond, *Circulation*, 91, 1175 (1995); Levi, *Circulation* 85, 305, (1992)). Elevated levels of PAI-1 have also been implicated in diseases such as polycystic ovary syndrome (Nordt, *Journal of clinical Endocrinology and Metabolism*, 85, 4, 1563 (2000)), bone loss induced by estrogen deficiency (Daci, *Journal of Bone and Mineral Research*, 15, 8, 1510 (2000)), cystic fibrosis, diabetes, chronic periodontitis, lymphomas, diseases associated with extracellular matrix accumulation, malignancies and diseases associated with neoangiogenesis, inflammatory diseases, vascular damage associated with infections, and diseases associated with increased uPA levels such as breast and ovarian cancer.

In view of the foregoing, there exists a need for the identification of inhibitors of PAI-1 activity and for methods of using the identified inhibitors to modulate PAI-1 expression or activity in a subject in order to treat disorders associated with elevated PAI-1 levels.

SUMMARY

The present invention provides substituted acetic acid derivatives and methods of using them. In certain embodiments, substituted acetic acid derivatives of the present invention include those compounds of the following formula:

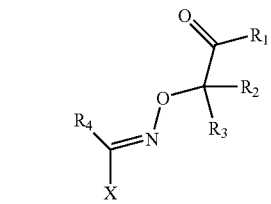

Formula 1 wherein:

$R_1$ is —OH, —OC$_1$-C$_8$ alkyl, or NH$_2$;

$R_2$ and $R_3$ are, independently, hydrogen, C$_1$-C$_8$ alkyl, —CH$_2$—C$_3$-C$_6$ cycloalkyl, —CH$_2$-pyridinyl, phenyl, or benzyl;

$R_4$ is hydrogen, C$_1$-C$_8$ alkyl, C$_3$-C$_6$ cycloalkyl, —CH$_2$—C$_3$-C$_6$ cycloalkyl, phenyl, benzyl, heteroaryl, or —CH$_2$-heteroaryl;

X is

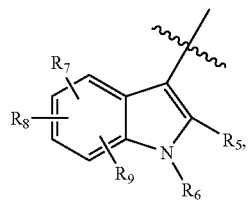

Formula A

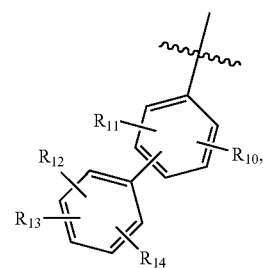

Formula B

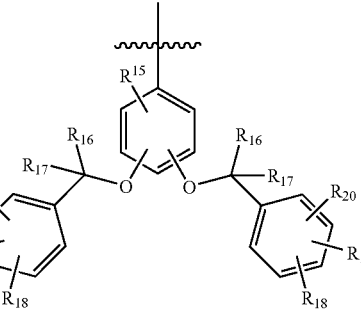

Formula C or

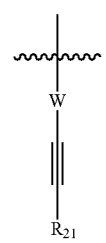

Formula D wherein:
- $R_5$ is hydrogen, $C_1$-$C_8$ alkyl, $C_3$-$C_6$ cycloalkyl, —$CH_2$—$C_3$-$C_6$ cycloalkyl, phenyl, benzyl, heteroaryl, or —$CH_2$-heteoraryl;
- $R_6$ is hydrogen, $C_1$-$C_8$ alkyl, —$(CH_2)_n$—, —$(CH_2)_n$—CH=$CH_2$, —$(CH_2)_n$—CH=CH-alkyl, —$(CH_2)_n$C≡CH, —$(CH_2)_n$C≡C-alkyl, aryl, $(CH_2)_n$-aryl, heteroaryl, $(CH_2)_n$-heteroaryl, —CO-aryl, —CO-heteroaryl, —CO-alkyl, —$SO_2$-alkyl, —$SO_2$-aryl, or —$SO_2$-heteroaryl;
- $R_7$, $R_8$ and $R_9$ are, independently, hydrogen, halogen, $C_1$-$C_6$ alkyl, $C_1$-$C_3$ perfluoroalkyl, —O—$C_1$-$C_3$ perfluoroalkyl, $C_1$-$C_3$ alkoxy, —OH, —$NH_2$, —$NO_2$, —$O(CH_2)_n$-aryl, —$O(CH_2)_n$-heteroaryl, aryl, or heteroaryl;
- $R_{10}$, $R_{11}$, $R_{12}$, $R_{13}$ and $R_{14}$ are, independently, hydrogen, halogen, $C_1$-$C_6$ alkyl, $C_1$-$C_3$ perfluoroalkyl, —O—$C_1$-$C_3$ perfluoroalkyl, $C_1$-$C_3$ alkoxy, —OH, —$NH_2$, —$NO_2$, —$O(CH_2)_n$-aryl, —$O(CH_2)_n$-heteroaryl, aryl, or heteroaryl;
- $R_{16}$ and $R_{17}$ are, independently, hydrogen, $C_1$-$C_8$ alkyl, $C_3$-$C_6$ cycloalkyl, —$CH_2$—$C_3$-$C_6$ cycloalkyl, aryl, benzyl, heteroaryl, or —$CH_2$-heteoraryl;
- $R_{15}$, $R_{18}$, $R_{19}$ and $R_{20}$ are, independently, hydrogen, halogen, $C_1$-$C_6$ alkyl, $C_1$-$C_3$ perfluoroalkyl, —O—$C_1$-$C_3$ perfluoroalkyl, $C_1$-$C_3$ alkoxy, —OH, —$NH_2$, —$NO_2$, —$O(CH_2)_n$-aryl, —$O(CH_2)_n$-heteroaryl, aryl, or heteroaryl;
- $R_{21}$ is hydrogen, $C_1$-$C_8$ alkyl, $C_1$-$C_8$ alkenyl, $C_1$-$C_8$ alkynyl, —$(CH_2)_p$-aryl, —$(CH_2)_p$-heteroaryl, —$(CH_2)_p$—O-aryl, —$(CH_2)_p$—O-heteroaryl, —$(CH_2)_p$—O—$(CH_2)_m$-aryl, —$(CH_2)_p$—O—$(CH_2)_m$-heteroaryl, aryl, or heteroaryl;
- W is aryl or heteroaryl;
- n is an integer from 0 to 5;
- p is an integer from 1 to 5; and
- m is an integer from 0 to 5.

Accordingly, the present invention provides, inter alia, substituted indolymethylideneaminooxy acetic acid derivatives of the following formula:

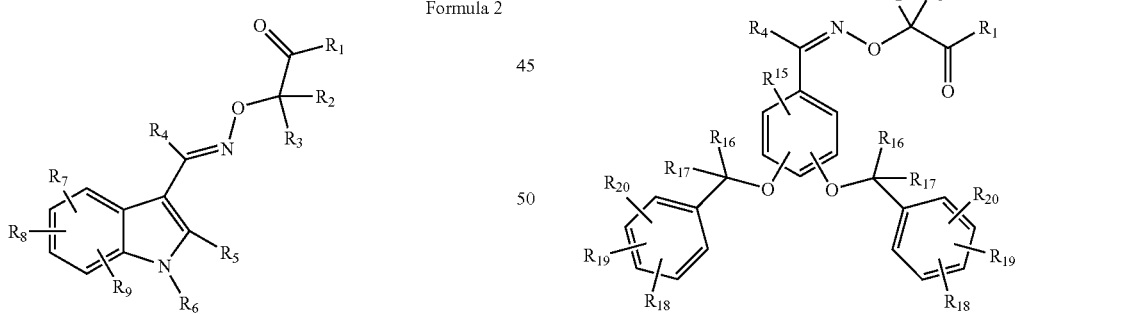

Formula 2 wherein $R_1$, $R_2$, $R_3$, $R_4$, $R_5$, $R_6$, $R_7$, $R_8$, $R_9$, and n are defined as above for Formula 1.

In certain exemplary embodiments of compounds of Formula 2, $R_1$ is —OH, $R_2$ is hydrogen, $R_3$ is hydrogen, $R_4$ is hydrogen, $R_5$ is hydrogen, $R_6$ is alkyl, alkenyl (allyl), alkynyl (propargyl) or arylalkyl (benzyl); $R_7$ is H, $R_8$ is benzyloxy where the benzyl group is optionally substituted with one or more groups selected from halogen, $C_1$-$C_6$ straight chain alkyl or $C_1$-$C_6$ branched alkyl, $C_1$-$C_3$ perfluoroalkyl, —O—$C_1$-$C_3$ perfluoroalkyl, $C_1$-$C_6$ alkoxy, or naphthyl; and $R_9$ is H.

The present invention also provides, inter alia, substituted biphenylmethylidene aminooxy acetic acid derivatives of the following formula:

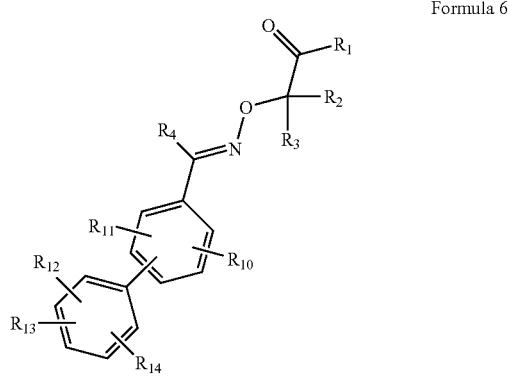

Formula 6 wherein $R_1$, $R_2$, $R_3$, $R_4$, $R_{10}$, $R_{11}$, $R_{12}$, $R_{13}$, $R_{14}$, and n are defined as above for Formula 1.

In certain exemplary embodiments of compounds of Formula 6, $R_1$ is —OH, $R_2$ is hydrogen, $R_3$ is hydrogen, $R_4$ is hydrogen, $R_{10}$ is hydrogen; $R_{11}$ is hydrogen; $R_{12}$ is hydrogen; $R_{13}$ is benzyloxy where the benzyl group is optionally substituted with one or more groups selected from halogen, $C_1$-$C_6$ straight chain alkyl or $C_1$-$C_6$ branched alkyl, $C_1$-$C_3$ perfluoroalkyl, —O—$C_1$-$C_3$ perfluoroalkyl, $C_1$-$C_6$ alkoxy, or naphthyl; and $R_{14}$ is hydrogen.

The present invention also provides, inter alia, bisbenzyloxyphenylmethylidene aminooxy acetic acid derivatives of the following formula:

Formula 9 wherein $R_1$, $R_2$, $R_3$, $R_4$, $R_{15}$, $R_{16}$, $R_{17}$, $R_{18}$, $R_{19}$, $R_{20}$, and n are defined as above for Formula 1.

In certain exemplary embodiments of compounds of Formula 9, $R_1$ is OH; $R_2$ is hydrogen; $R_3$ is hydrogen, $R_4$ is hydrogen, $R_{15}$ is hydrogen; $R_{16}$ is hydrogen, $R_{17}$ is hydrogen, $R_{18}$, $R_{19}$ and $R_{20}$ are independently hydrogen, halogen, alkyl, or perfluoroalkyl.

The present invention also provides, inter alia, substituted acetylenic oximeacetic acid derivatives of the following formula:

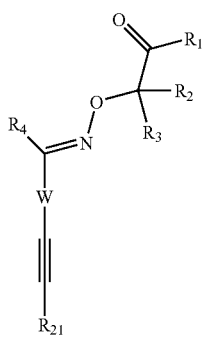

Formula 11 wherein $R_1$, $R_2$, $R_3$, $R_4$, W, $R_{21}$, m, and p are defined as above for Formula 1.

In certain embodiments of Formula 11, $R_1$ is OH; $R_2$ is hydrogen; $R_3$ is hydrogen, $R_4$ is hydrogen, W is aryl, and $R_{21}$ is straight chain alkyl, branched alkyl, or —(CH$_2$)—O-aryl where the aryl group is optionally substituted with one or more groups selected from halogen, straight chain alkyl, branched alkyl, or perfluoroalkyl.

The present invention also provides, inter alia, pharmaceutically acceptable salt or ester forms of formulas 1-13.

The present invention further provides, inter alia, methods of using substituted acetic acid derivatives. In one aspect of the present invention, a therapeutically effective amount of one or more substituted acetic acid derivatives is administered to a subject in order to treat a PAI-1 related disorder, e.g., by inhibiting PAI-1 activity in the subject. PAI-1 activity is associated with a number of diseases and conditions. For example, in one embodiment of the present invention, PAI-1 activity is associated with impairment of the fibrinolytic system. In other embodiments, PAI-1 activity is associated with thrombosis, e.g., venous thrombosis, arterial thrombosis, cerebral thrombosis, and deep vein thrombosis, atrial fibrillation, pulmonary fibrosis, thromboembolic complications of surgery, cardiovascular disease, e.g., myocardial ischemia, atherosclerotic plaque formation, chronic obstructive pulmonary disease, renal fibrosis, polycystic ovary syndrome, Alzheimer's disease, or cancer.

DETAILED DESCRIPTION

A. General Overview

The present invention provides compounds that inhibit PAI-1 activity, processes for preparing such compounds, pharmaceutical compositions containing such compounds, and methods for using such compounds in medical therapies. The compounds have properties that are useful for the treatment, including the prevention and inhibition, of a wide variety of diseases and disorders involving the production and/or action of PAI-1. These include disorders resulting from impairment of the fibrinolytic system including, but not limited to, thrombosis, coronary heart disease, renal fibrosis, atherosclerotic plaque formation, pulmonary disease, myocardial ischemia, atrial fibrillation, coagulation syndromes, thromboembolic complications of surgery, peripheral arterial occlusion and pulmonary fibrosis. Other disorders include, but are not limited to, polycystic ovary syndrome, Alzheimer's disease, and cancer.

The terms "alkyl" and "alkylene," as used herein, whether used alone or as part of another group, refer to substituted or unsubstituted aliphatic hydrocarbon chains, the difference being that alkyl groups are monovalent (i.e., terminal) in nature whereas alkylene groups are divalent and typically serve as linkers. Both include, but are not limited to, straight and branched chains containing from 1 to about 12 carbon atoms, preferably 1 to 6 carbon atoms, unless explicitly specified otherwise. For example, methyl, ethyl, propyl, isopropyl, butyl, i-butyl and t-butyl are encompassed by the term "alkyl." Specifically included within the definition of "alkyl" are those aliphatic hydrocarbon chains that are optionally substituted. Representative optional substituents include, but are not limited to, hydroxy, acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl. Preferably, alkyl and alkylene groups are unsubstituted.

The carbon number as used in the definitions herein refers to carbon backbone and carbon branching, but does not include carbon atoms of the substituents, such as alkoxy substitutions and the like, when present.

The term "alkenyl", as used herein, whether used alone or as part of another group, refers to a substituted or unsubstituted aliphatic hydrocarbon chain and includes, but is not limited to, straight and branched chains having 2 to about 10 carbon atoms (unless explicitly specified otherwise) and containing at least one double bond. Preferably, the alkenyl moiety has 1 or 2 double bonds. Such alkenyl moieties can exist in the E or Z conformations and the compounds of this invention include both conformations. Specifically included within the definition of "alkenyl" are those aliphatic hydrocarbon chains that are optionally substituted. Representative optional substituents include, but are not limited to, hydroxy, acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl. Heteroatoms, such as O or S attached to an alkenyl should not be attached to a carbon atom that is bonded to a double bond. Preferably, alkenyl groups are unsubstituted.

The term "alkynyl", as used herein, whether used alone or as part of another group, refers to a substituted or unsubstituted aliphatic hydrocarbon chain and includes, but is not limited to, straight and branched chains having 2 to about 10 carbon atoms (unless explicitly specified otherwise) and containing at least one triple bond. Preferably, the alkynyl moiety has 3 to 6 carbon atoms. In certain embodiments, the alkynyl can contain more than one triple bond and, in such cases, the alknyl group must contain at least three carbon atoms. Specifically included within the definition of "alkynyl" are those aliphatic hydrocarbon chains that are optionally substituted. Representative optional substituents include, but are not limited to, hydroxy, acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl. Heteroatoms, such as O or S attached to an alkynyl should not be attached to the carbon that is bonded to a triple bond. Preferably, alkynyl groups are unsubstituted.

The term "cycloalkyl" as used herein, whether alone or as part of another group, refers to a substituted or unsubstituted alicyclic hydrocarbon group having 3 to about 20 carbon atoms (unless explicitly specified otherwise), preferably 3 to 8 carbon atoms. Specifically included within the definition of "cycloalkyl" are those alicyclic hydrocarbon groups that are optionally substituted. For example, in certain embodiments of the present invention, the rings of the cycloalkyl are optionally substituted by 1 to 3 groups selected from halogen, $C_1$-$C_3$ alkyl, $C_1$-$C_3$ perfluoroalkyl, —O—$C_1$-$C_3$ perfluoroalkyl, $C_1$-$C_3$ alkoxy, —OH, —NH$_2$, —CN, or —NO$_2$. Preferably, cycloalkyl groups are unsubstituted.

The term "aryl", as used herein, whether used alone or as part of another group, is defined as a substituted or unsubstituted aromatic hydrocarbon ring group having 5 to about 50 carbon atoms with from 6 to 14 carbon atoms being preferred. The "aryl" group can have a single ring or multiple condensed rings. The term "aryl" includes, but is not limited to phenyl, α-naphthyl, β-naphthyl, biphenyl, anthryl, phenanthryl, tetrahydronaphthyl, fluorenyl, indanyl, biphenylenyl, and acenaphthenyl. Specifically included within the definition of "aryl" are those aromatic groups that are optionally substituted. Accordingly, the aryl groups (e.g., phenyl) described herein refer to both unsubstituted or substituted groups. For example, in representative embodiments of the present invention, the, "aryl" groups are optionally substituted with from 1 to 5 substituents selected from the group consisting of acyloxy, hydroxy, acyl, aryl, alkyl of 1 to 6 carbon atoms, alkoxy of 1 to 6 carbon atoms, alkenyl of 2 to 6 carbon atoms, alkynyl of 2 to 6 carbon atoms, substituted alkyl, substituted alkoxy, substituted alkenyl, substituted alkynyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. Exemplary substituents on the aryl groups herein include alkyl, alkoxy, halo, cyano, nitro, trihalomethyl, and thioalkoxy. In certain embodiments of the present invention, the rings of the aryl groups are optionally substituted by 1 to 3 groups independently selected from halogen, $C_1$-$C_3$ alkyl, $C_1$-$C_3$ perfluoroalkyl, —O—$C_1$-$C_3$ perfluoroalkyl, $C_1$-$C_3$ alkoxy, naphthyl, —OH, —NH$_2$, —CN or —NO$_2$.

As used herein, the term "heteroaryl", whether used alone or as part of another group, is defined as a substituted or unsubstituted aromatic heterocyclic ring system (monocyclic or bicyclic). Heteroaryl groups can have, for example, from about 3 to about 50 carbon atoms (unless explicitly specified otherwise) with from 4 to 10 being preferred. In some embodiments, heteroaryl groups are aromatic heterocyclic rings systems having 4 to 14 ring atoms including carbon atoms and 1, 2, 3, or 4 heteroatoms selected from oxygen, nitrogen or sulfur. Representative heteroaryl groups are furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Specifically included within the definition of "heteroaryl" are those aromatic groups that are optionally substituted. Accordingly, the heteroaryl groups (e.g., pyridinyl) described herein refer to both unsubstituted or substituted groups. In representative embodiments of the present invention, the, "heteroaryl" groups are optionally substituted with 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, substituted alkyl, substituted alkoxy, substituted alkenyl, substituted alkynyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. In exemplary embodiments of the present invention, the rings of the heteroaryl group are optionally substituted by 1 to 3 groups selected from halogen, $C_1$-$C_3$ alkyl, $C_1$-$C_3$ perfluoroalkyl, —O—$C_1$-$C_3$ perfluoroalkyl, $C_1$-$C_3$ alkoxy, —OH, —NH$_2$, —CN, or —NO$_2$.

The term "alkoxy" as used herein, refers to the group $R_a$—O— wherein $R_a$ is an alkyl group as defined above. Specifically included within the definition of "alkoxy" are those alkoxy groups that are optionally substituted Exemplary substituents on the alkyl, alkenyl, alkynyl, thioalkoxy and alkoxy groups mentioned above include, but are not limited to, halogen, —O—$C_1$-$C_6$ alkyl, —NH—$C_1$-$C_6$ alkyl, —CN, —OH, and amino groups, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl.

The rings of the cycloalkyl, pyridinyl, phenyl, and benzyl groups mentioned above are optionally substituted by 1 to 3 groups. Exemplary substituents on the rings of the cycloalkyl, pyridinyl, phenyl, and benzyl groups include halogen, $C_1$-$C_3$ alkyl, $C_1$-$C_3$ perfluoroalkyl, —O—$C_1$-$C_3$ perfluoroalkyl, $C_1$-$C_3$ alkoxy, —OH, —CN, —NH$_2$, or —NO$_2$.

The term "arylalkyl", as used herein, whether used alone or as part of another group, refers to the group —$R_a$—$R_b$, where $R_a$ is an alkylene group as defined above, substituted by $R_b$, an aryl group, as defined above. Examples of arylalkyl moieties include, but are not limited to, benzyl, 1-phenylethyl, 2-phenylethyl, 3-phenylpropyl, 2-phenylpropyl and the like.

The term "alkylheteroaryl", as used herein, whether used alone or as part of another group, refers to the group —$R_c$—$R_a$, where $R_c$ is a heteroaryl group as defined above, substituted with $R_a$, an alkylene group as defined above.

The term "heterocycle", as used herein, whether used alone or as part of another group, refers to a stable 3 to about 10-member ring containing carbons atoms and from 1 to 3 heteroatoms selected from the group consisting of nitrogen, phosphorous, oxygen, and sulfur. A heterocycle of this invention can be either a monocyclic or bicyclic ring system, and can be either saturated or partially saturated. Heterocycle groups include, but are not limited to, aziridinyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, and tetrahydroisoquinolinyl.

The term "perfluoroalkyl", as used herein, whether used alone or as part of another group, refers to a saturated aliphatic hydrocarbon having 1 to about 6 carbon atoms and two or more fluorine atoms and includes, but is not limited to, straight or branched chains, such as —$CF_3$, —$CH_2CF_3$, —$CF_2CF_3$ and —$CH(CF_3)_2$.

The term "halogen" or "halo" refers to chlorine, bromine, fluorine, and iodine.

The term "m" can be 0, 1, 2, 3, 4, 5. "p" can be 0, 1, 2, 3, 4, or 5. "n" can be 0, 1, 2, 3, 4, 5.

The term "treating" or "treatment" refers to any indicia of success in amelioration of an injury, pathology, or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being. The treatment or amelioration of symptoms can be based on objective or subjective parameters; including the results of a physical examination, neurological examination, and/or psychiatric evaluation. "Treating" or "treatment of a PAI-1 related disorder" includes preventing the onset of symptoms in a subject that may be predisposed to a PAI-1 related disorder but does not yet experience or exhibit symptoms of the disorder (prophylactic treatment), inhibiting the symptoms of the disorder (slowing or arresting its development), providing relief from the symptoms or side-effects of the disorder (including palliative treatment), and/or relieving the symptoms of the disorder (causing regression). Accordingly, the term "treating" includes the administration of the compounds or agents of the present invention to a subject to prevent or delay, to alleviate, or to arrest or inhibit development of the symptoms or conditions associated with PAI-1 related disorders, e.g., tumor growth associated with cancer. A skilled medical practitioner will know how to use standard methods to determine whether a patient is suffering from a disease associated with enhanced levels and/or activity of PAI-1, e.g., by examining the patient and determining whether the patient is suffering from a disease known to be associated with elevated PAI-1 levels or activity or by assaying for PAI-1 levels in blood plasma or tissue of the individual suspected of suffering from a PAI-1 related disease and comparing PAI-1 levels in the blood plasma or tissue of the individual suspected of suffering from a PAI-1 related disease to PAI-1 levels in the blood plasma or tissue of a healthy individual. Increased PAI-1 levels are indicative of disease. Accordingly, the present invention provides, inter alia, methods of administering a compound of the present invention to a subject and determining levels of PAI-1 in the subject. The level of PAI-1 in the subject can be determined before and/or after administration of the compound.

In healthy individuals, PAI-1 is found at low levels in the plasma (from about 5-26 ng/mL), but it is elevated in many PAI-1 related disorders, including, for example, atherosclerosis (Schneiderman J. et. al, *Proc Natl Acad Sci* 89: 6998-7002, 1992) deep vein thrombosis (Juhan-Vague I, et. al, *Thromb Haemost* 57: 67-72, 1987), and non-insulin dependent diabetes mellitus (Juhan-Vague I, et. al, *Thromb Haemost* 78: 565-660, 1997). PAI-1 stabilizes both arterial and venous thrombi, contributing respectively to coronary arterial occlusion in post-myocardial infarction (Hamsten A, et. al. *Lancet* 2:3-9, 1987), and venous thrombosis following post-operative recovery from orthopedic surgery. (Siemens H J, et. al, *J Clin Anesthesia* 11: 622-629, 1999). Plasma PAI-1 is also elevated, for example, in postmenopausal women, and has been proposed to contribute to the increased incidence of cardiovascular disease in this population (Koh K et. al, *N Engl J Med* 336: 683-690, 1997).

The term "PAI-1 related disorder or disease" refers to any disease or condition that is associated with increased or enhanced expression or activity of PAI-1 or increased or enhanced expression or activity of a gene encoding PAI-1. Examples of such increased activity or expression can include one or more of the following: activity of the protein or expression of the gene encoding the protein is increased above the level of that in normal subjects; activity of the protein or expression of the gene encoding the protein is in an organ, tissue or cell where it is not normally detected in normal subjects (i.e. spatial distribution of the protein or expression of the gene encoding the protein is altered); activity of the protein or expression of the gene encoding the protein is increased when activity of the protein or expression of the gene encoding the protein is present in an organ, tissue or cell for a longer period than in a normal subjects (i.e., duration of activity of the protein or expression of the gene encoding the protein is increased). A normal or healthy subject is a subject not suffering from a PAI-1 related disorder or disease.

The term "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" refers to salts and esters that are pharmaceutically acceptable and have the desired pharmacological properties. Such salts include, for example, salts that can be formed where acidic protons present in the compounds are capable of reacting with inorganic or organic bases. Suitable inorganic salts include, for example, those formed with the alkali metals or alkaline earth metals, e.g. sodium and potassium, magnesium, calcium, and aluminum. Suitable organic salts include, for example, those formed with organic bases such as the amine bases, e.g. ethanolamine, diethanolamine, triethanolamine, tromethamine, N methylglucamine, and the like. Pharmaceutically acceptable salts can also include acid addition salts formed from the reaction of basic moieties, such as amines, in the parent compound with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g. $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention can be present in more than one stereoisomeric form, and the naming of such compounds is intended to include all single stereoisomers and all mixtures (whether racemic or otherwise) of such stereoisomers.

"Inhibitors," "activators," and "modulators" of expression or of activity are used to refer to inhibitory, activating, or modulating molecules, respectively, identified using in vitro and in vivo assays for expression or activity. Inhibitors of the present invention are compositions that, inhibit expression of PAI-1 or bind to, partially or totally block stimulation, decrease, prevent, delay activation, inactivate, desensitize, or down regulate the activity of PAI-1. Samples or assays comprising PAI-1 can be treated with a composition of the present invention and compared to control samples without a composition of the present invention. Control samples (untreated with compositions of the present invention) can be assigned a relative activity value of 100%. In certain embodiments, inhibition of PAI-1 is achieved when the activity value relative to the control is about 80% or less, optionally 50% or 25, 10%, 5% or 1%.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the compound.

A "therapeutically effective amount" or "pharmaceutically effective amount" means the amount that, when administered to a subject, produces effects for which it is administered. For example, a "therapeutically effective amount," when administered to a subject to inhibit PAI-1 activity, is sufficient to inhibit PAI-1 activity. A "therapeutically effective amount," when administered to a subject for treating a disease, is sufficient to effect treatment for that disease.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and formulations of the present invention.

When any variable occurs more than one time in any constituent or in any formula, its definition in each occurrence is independent of its definition at every other occurrence. Combinations of substituents and/or variables are permissible only if such combinations result in stable compounds.

B. Substituted Acetic Acid Derivatives

The present invention provides substituted acetic acid derivatives. Such derivatives are preferably administered to inhibit PAI-1 expression or activity in a subject and, ultimately, to treat diseases or conditions associated with increased PAI-1 activity in a subject, e.g., a PAI-1 related disorder.

Substituted acetic acid derivatives include those compounds of the following formula:

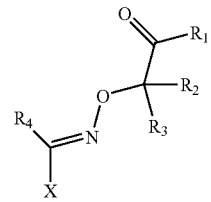

Formula 1 wherein:
$R_1$ is —OH, —$OC_1$-$C_8$ alkyl, or —$NH_2$;
$R_2$ and $R_3$ are, independently, hydrogen, $C_1$-$C_8$ alkyl, —$CH_2$—$C_3$-$C_6$ cycloalkyl, —$CH_2$-pyridinyl, phenyl, or benzyl;
$R_4$ is hydrogen, $C_1$-$C_8$ alkyl, $C_3$-$C_6$ cycloalkyl, —$CH_2$—$C_3$-$C_6$ cycloalkyl, pyridinyl, —$CH_2$-pyridinyl, phenyl, benzyl, heteroaryl, or —$CH_2$-hetoaryl;
X is

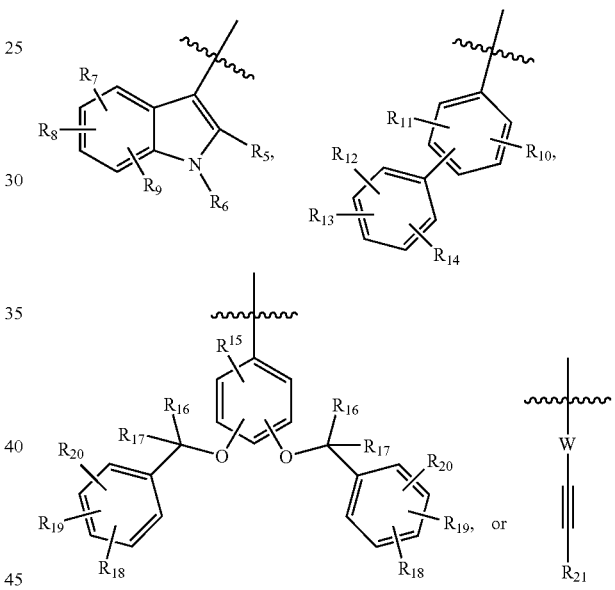

wherein:
$R_5$ is hydrogen, $C_1$-$C_8$ alkyl, $C_3$-$C_6$ cycloalkyl, —$CH_2$—$C_3$-$C_6$ cycloalkyl, pyridinyl, —$CH_2$-pyridinyl, phenyl, benzyl, heteroaryl, or —$CH_2$-heteroaryl;
$R_6$ is hydrogen, $C_1$-$C_8$ alkyl, —$(CH_2)_n$—CH=CH, —$(CH_2)$, —CH=C-alkyl, —$(CH_2)_n$C≡CH, —$(CH_2)_n$C≡C-alkyl, aryl, $(CH_2)_n$-aryl, heteroaryl, $(CH_2)_n$-heteroaryl, —CO-aryl, —CO-heteroaryl, —CO-alkyl, —$SO_2$-alkyl, —$SO_2$-aryl, or —$SO_2$-heteroaryl;
$R_7$, $R_8$ and $R_9$ are, independently, hydrogen, halogen, $C_1$-$C_6$ alkyl, $C_1$-$C_3$ perfluoroalkyl, —O—$C_1$-$C_3$ perfluoroalkyl, $C_1$-$C_3$ alkoxy, —OH, —$NH_2$, —$NO_2$, —$O(CH_2)_n$-aryl, —$O(CH_2)_n$-heteroaryl, aryl, or heteroaryl;
$R_{10}$, $R_{11}$, $R_{12}$, $R_{13}$ and $R_{14}$ are, independently, hydrogen, halogen, $C_1$-$C_6$ alkyl, $C_1$-$C_3$ perfluoroalkyl, —O—$C_1$-$C_3$ perfluoroalkyl, $C_1$-$C_3$ alkoxy, —OH, —$NH_2$, —$NO_2$, —$O(CH_2)_n$-aryl, —$O(CH_2)_n$-heteroaryl, aryl, or heteroaryl;

$R_{16}$ and $R_{17}$ are, independently, hydrogen, $C_1$-$C_8$ alkyl, $C_3$-$C_6$ cycloalkyl, —$CH_2$—$C_3$-$C_6$ cycloalkyl, pyridinyl, —$CH_2$-pyridinyl, aryl, benzyl, heteroaryl, or —$CH_2$-heteroaryl;

$R_{15}$, $R_{18}$, $R_{19}$ and $R_{20}$ are, independently, hydrogen, halogen, $C_1$-$C_6$ alkyl, $C_1$-$C_3$ perfluoroalkyl, —O—$C_1$-$C_3$ perfluoroalkyl, $C_1$-$C_3$ alkoxy, —OH, —$NH_2$, —$NO_2$, —O($CH_2$)$_n$-aryl, —O($CH_2$)$_n$-heteroaryl, aryl, or heteroaryl;

$R_{21}$ is hydrogen, $C_1$-$C_8$ alkyl, $C_1$-$C_8$ alkenyl, $C_1$-$C_8$ alkynyl, —($CH_2$)$_p$-aryl, —($CH_2$)$_p$-heteroaryl, —($CH_2$)$_p$—O-aryl, —($CH_2$)$_p$—O-heteroaryl, —($CH_2$)$_p$—O—($CH_2$)$_m$-aryl, —($CH_2$)$_p$—O—($CH_2$)$_m$-heteroaryl, aryl, or heteroaryl;

W is aryl or heteroaryl;

n is an integer from 0 to 5;

p is an integer from 1 to 5; and m is an integer from 0 to 5.

Accordingly, in some embodiments, substituted acetic acid derivatives of the present invention include substituted indolymethylideneaminooxy acetic acid derivatives of the following formula:

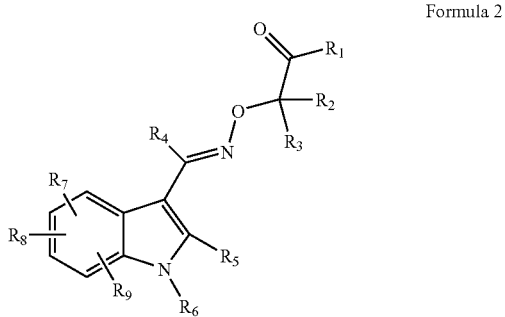

Formula 2 wherein $R_1$, $R_2$, $R_3$, $R_4$, $R_5$, $R_6$, $R_7$, $R_8$, $R_9$, and n are defined as above for Formula 1.

Compounds of the present invention also include prodrugs, stereoisomers, or pharmaceutically acceptable salt or ester forms of Formula 2.

$R_1$ can be —OH, —O$C_1$-$C_8$ alkyl, or $NH_2$. In certain compounds of Formula 2, $R_1$ is —O$C_1$-$C_6$ alkyl or —OH. Most preferably $R_1$ is —OH. In such embodiments, $R_2$, $R_3$, $R_4$, $R_5$, $R_6$, $R_7$, $R_8$, $R_9$, and n are as defined herein for compounds of Formula 2.

$R_2$ and $R_3$ can be hydrogen, $C_1$-$C_8$ alkyl, —$CH_2$—$C_3$-$C_6$ cycloalkyl, —$CH_2$-pyridinyl, phenyl, or benzyl. In certain compounds of Formula 2, $R_2$ and $R_3$ are, independently, $CH_2$—$C_3$-$C_6$ cycloalkyl, —$CH_2$-pyridinyl, phenyl, or benzyl wherein the rings of the cycloalkyl, pyridinyl, phenyl or benzyl groups are optionally substituted by 1 to 3 groups selected from halogen, $C_1$-$C_3$ alkyl, $C_1$-$C_3$ perfluoroalkyl, —O—$C_1$-$C_3$ perfluoroalkyl, $C_1$-$C_3$ alkoxy, —OH, —$NH_2$, —CN, or —$NO_2$. In other embodiments, $R_2$ and $R_3$ are, independently alkyl or hydrogen. In certain preferred embodiments, $R_2$ and $R_3$ are hydrogen. In such embodiments, $R_1$, $R_4$, $R_5$, $R_6$, $R_7$, $R_8$, $R_9$, and n are as defined herein for compounds of Formula 2

$R_4$ can be hydrogen, $C_1$-$C_8$ alkyl, $C_3$-$C_6$ cycloalkyl, —$CH_2$—$C_3$-$C_6$ cycloalkyl, phenyl, benzyl, heteroaryl, or —$CH_2$-heteroaryl and $R_5$ can be hydrogen, $C_1$-$C_8$ alkyl, $C_3$-$C_6$ cycloalkyl, —$CH_2$—$C_3$-$C_6$ cycloalkyl, phenyl, benzyl, heteroaryl, or —$CH_2$-heteroaryl. In certain compounds of Formula 2, $R_4$ and $R_5$ are, independently, $C_3$-$C_6$ cycloalkyl, $CH_2$—$C_3$-$C_6$ cycloalkyl, pyridinyl, —$CH_2$-pyridinyl, phenyl or benzyl wherein the rings of the cycloalkyl, pyridinyl, phenyl, and benzyl groups are optionally substituted by 1 to 3 groups selected from halogen, $C_1$-$C_3$ alkyl, $C_1$-$C_3$ perfluoroalkyl, —O—$C_1$-$C_3$ perfluoroalkyl, $C_1$-$C_3$ alkoxy, —OH, —$NH_2$, or —$NO_2$. In other embodiments, $R_4$ and $R_5$ groups are hydrogen or $C_1$-$C_6$ alkyl. In certain preferred embodiments, $R_4$ and $R_5$ are hydrogen. In such embodiments, $R_1$, $R_2$, $R_3$, $R_5$, $R_6$, $R_7$, $R_8$, $R_9$, and n are as defined herein for compounds of Formula 2

$R_6$ can be hydrogen, $C_1$-$C_8$ alkyl, —($CH_2$), —CH=CH, —($CH_2$), —CH=C-alkyl, —($CH_2$)$_n$C≡CH, —($CH_2$)$_n$C≡C-alkyl, aryl, ($CH_2$)$_n$-aryl, heteroaryl, ($CH_2$)$_n$-heteroaryl, —CO-aryl, —CO-heteroaryl, —CO-alkyl, —$SO_2$-alkyl, —$SO_2$-aryl, or —$SO_2$-heteroaryl. In certain compounds of Formula 2, $R_6$ is aryl, ($CH_2$)$_n$-aryl, heteroaryl, ($CH_2$)$_n$-heteroaryl, —CO-aryl, —CO-heteroaryl, —$SO_2$-aryl, or —$SO_2$-heteroaryl wherein the rings of the aryl and heteroaryl groups are optionally substituted by 1 to 3 groups selected from halogen, $C_1$-$C_3$ alkyl, $C_1$-$C_3$ perfluoroalkyl, —O—$C_1$-$C_3$ perfluoralkyl, $C_1$-$C_3$ alkoxy, —OH, —$NH_2$, or —$NO_2$. In certain preferred embodiments $R_6$ is —$SO_2$-alkyl, aralkyl, alkyl, alkenyl, or alkynyl. For example, in some embodiments, $R_6$ is benzyl, allyl, ethyl, propargyl, or methyl. In such embodiments, $R_1$, $R_2$, $R_3$, $R_4$, $R_5$, $R_7$, $R_8$, $R_9$, and n are as defined herein for compounds of Formula 2.

$R_7$, $R_8$ and $R_9$ can be hydrogen, halogen, $C_1$-$C_6$ alkyl, $C_1$-$C_3$ perfluoroalkyl, —O—$C_1$-$C_3$ perfluoroalkyl, $C_1$-$C_3$ alkoxy, —OH, —$NH_2$, —$NO_2$, —O($CH_2$)$_n$-aryl, —O($CH_2$)$_n$-heteroaryl, aryl, or heteroaryl. In certain compounds of Formula 2, $R_7$, $R_8$, and $R_9$ are, independently, —O($CH_2$)$_n$-aryl, —O($CH_2$)$_n$-heteroaryl, aryl, or hetreoaryl wherein the rings of the aryl and/or heteroaryl groups are optionally substituted by 1 to 3 groups selected from halogen, $C_1$-$C_3$ alkyl, $C_1$-$C_3$ perfluoroalkyl, —O—$C_1$-$C_3$ perfluoralkyl, $C_1$-$C_3$ alkoxy, —OH, —$NH_2$, or —$NO_2$. In certain preferred embodiments, $R_7$, $R_8$, and $R_9$ are, independently, hydrogen, or O($CH_2$)$_n$-aryl where the ring of the aryl group is optionally substituted with 1 to 3 groups selected from alkyl, perfluoroalkyl, halogen, or aryl. In some embodiments, $R_7$, $R_8$, and $R_9$ are, independently, hydrogen, or benzyloxy where the benzyl ring is optionally substituted with 1 to 3 groups selected from butyl, $CF_3$, bromine, chlorine, methyl and naphthyl. In such embodiments, $R_1$, $R_2$, $R_3$, $R_4$, $R_5$, $R_6$, and n are as defined herein for compounds of Formula 2

In one exemplary embodiment of the present invention, $R_4$ is hydrogen, $C_3$-$C_6$ cycloalkyl, —$CH_2$—$C_3$-$C_6$ cycloalkyl, phenyl, benzyl, heteroaryl, or —$CH_2$-heteoaryl and $R_1$, $R_2$, $R_3$, $R_5$, $R_6$, $R_7$, $R_7$, $R_8$, $R_9$, and n are as described herein for compounds of Formula 2.

In another exemplary embodiment of the present invention, $R_1$, $R_2$, $R_3$, $R_5$, $R_6$, $R_7$, $R_8$, and $R_9$ cannot simultaneously be hydrogen.

In certain embodiments of the present invention, such substituted indolymethylideneaminooxy acetic acid derivatives include the following compounds:

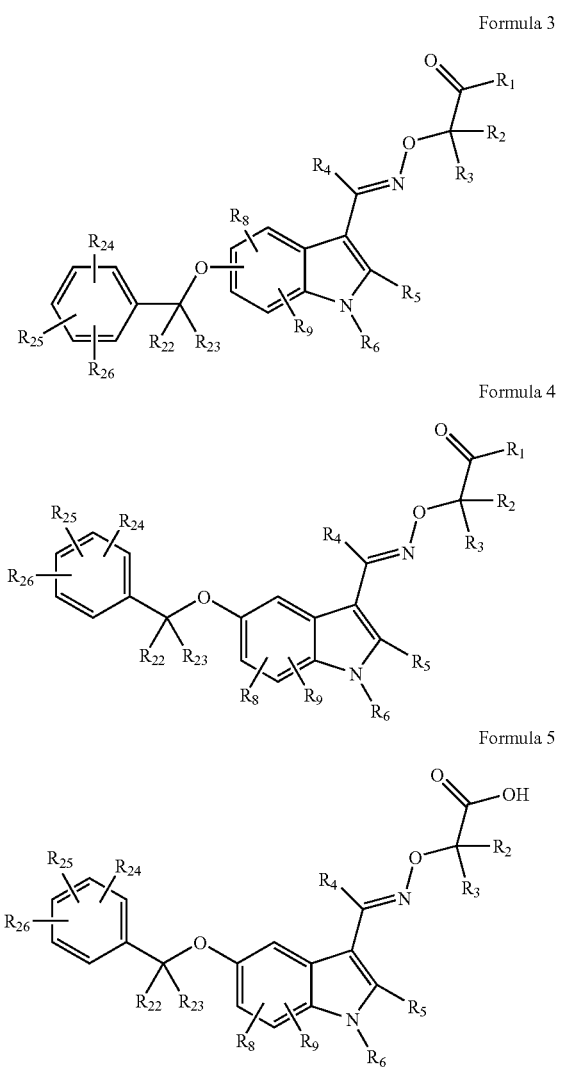

Formula 3

Formula 4

Formula 5 wherein $R_1$, $R_2$, $R_3$, $R_4$, $R_5$, $R_6$, $R_7$, $R_8$, $R_9$, and n are defined as above for Formula 1, and $R_{22}$ and $R_{23}$ can be, independently, hydrogen, $C_1$-$C_8$ alkyl, —$CH_2$—$C_3$-$C_6$ cycloalkyl, —$CH_2$-pyridinyl, phenyl, or benzyl; and $R_{24}$, $R_{25}$ and $R_{26}$ can be, independently, hydrogen, halogen, $C_1$-$C_6$ alkyl (preferably $C_1$-$C_3$ alkyl), $C_1$-$C_3$ perfluoroalkyl, —O—$C_1$-$C_3$ perfluoroalkyl, $C_1$-$C_6$ alkoxy (preferably $C_1$-$C_3$ alkoxy), —OH, —$NH_2$, —$NO_2$, —O($CH_2$)$_n$-aryl, —O($CH_2$)$_n$-heteroaryl, aryl, or heteroaryl.

In certain exemplary embodiments, the rings of the cycloalkyl, pyridinyl, phenyl and benzyl groups represented by $R_{22}$ and $R_{23}$ are optionally substituted by 1 to 3 groups selected from halogen, $C_1$-$C_3$ alkyl, $C_1$-$C_3$ perfluoroalkyl, —O—$C_1$-$C_3$ perfluoroalkyl, $C_1$-$C_3$ alkoxy, —OH, —$NH_2$, or —$NO_2$ and/or the rings of the aryl and heteroaryl groups represented by $R_{24}$, $R_{25}$, and $R_{26}$ are optionally substituted by 1 to 3 groups selected from halogen, $C_1$-$C_3$ alkyl, $C_1$-$C_3$ perfluoroalkyl, —O—$C_1$-$C_3$ perfluoroalkyl, $C_1$-$C_3$ alkoxy, —OH, —$NH_2$, or —$NO_2$.

In certain preferred embodiments of the present invention, $R_1$ is —OH, unsubstituted —O$C_1$-$C_8$ alkyl, or $NH_2$;

$R_2$ and $R_3$ are, independently, hydrogen, unsubstituted $C_1$-$C_8$ alkyl, —$CH_2$—$C_3$-$C_6$ cycloalkyl, —$CH_2$-pyridinyl, phenyl, or benzyl wherein the rings of the cycloalkyl, pyridinyl, phenyl, or benzyl groups are optionally substituted by 1 to 3 groups selected from halogen, unsubstituted $C_1$-$C_3$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —CN, —OH, —$NH_2$, or —$NO_2$;

$R_4$ is hydrogen, unsubstituted $C_1$-$C_8$ alkyl, $C_3$-$C_6$ cycloalkyl, —$CH_2$—$C_3$-$C_6$ cycloalkyl, pyridinyl, —$CH_2$-pyridinyl, phenyl, benzyl, heteroaryl, or —$CH_2$-heteoaryl wherein the rings of the cycloalkyl, pyridinyl, phenyl, heteroaryl, or benzyl groups are optionally substituted by 1 to 3 groups selected from halogen, unsubstituted $C_1$-$C_3$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —OH, —$NH_2$, or —$NO_2$;

$R_5$ is hydrogen, unsubstituted $C_1$-$C_8$ alkyl, $C_3$-$C_6$ cycloalkyl, —$CH_2$—$C_3$-$C_6$ cycloalkyl, pyridinyl, —$CH_2$-pyridinyl, phenyl, benzyl, heteroaryl, or —$CH_2$-heteoaryl wherein the rings of the cycloalkyl, pyridinyl, phenyl, heteroaryl, or benzyl groups are optionally substituted by 1 to 3 groups selected from halogen, unsubstituted $C_1$-$C_3$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —OH, —$NH_2$, or —$NO_2$;

$R_6$ is hydrogen, unsubstituted $C_1$-$C_8$ alkyl, —($CH_2$), —CH=CH, unsubstituted —($CH_2$), —CH=C-alkyl, —($CH_2$)$_n$C≡CH, unsubstituted —($CH_2$)$_n$C≡C-alkyl, aryl, ($CH_2$)$_n$-aryl, heteroaryl, ($CH_2$)$_n$-heteroaryl, —CO-aryl, —CO-heteroaryl, unsubstituted —CO-alkyl, unsubstituted —$SO_2$-alkyl, —$SO_2$-aryl, or —$SO_2$-heteroaryl wherein the rings of the aryl and heteroaryl groups are optionally substituted by 1 to 3 groups selected from halogen, unsubstituted $C_1$-$C_3$ alkyl, unsubstituted $C_1$-$C_3$ perfluoroalkyl, unsubstituted —O—$C_1$-$C_3$ perfluoroalkyl, $C_1$-$C_3$ alkoxy, —OH, —$NH_2$, or —$NO_2$;

$R_7$, $R_8$ and $R_9$ are, independently, hydrogen, halogen, unsubstituted $C_1$-$C_6$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —OH, —$NH_2$, —$NO_2$, —O($CH_2$)$_n$-aryl, —O($CH_2$)$_n$-heteroaryl, aryl, or heteroaryl wherein the rings of the aryl and heteroaryl groups are optionally substituted by 1 to 3 groups selected from halogen, unsubstituted $C_1$-$C_3$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —OH, —$NH_2$, or —$NO_2$;

$R_{22}$ and $R_{23}$ are, independently, hydrogen, unsubstituted $C_1$-$C_8$ alkyl, —$CH_2$—$C_3$-$C_6$ cycloalkyl, —$CH_2$-pyridinyl, phenyl, or benzyl wherein the rings of the cycloalkyl, pyridinyl, phenyl and benzyl groups are optionally substituted by 1 to 3 groups selected from halogen, unsubstituted $C_1$-$C_3$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —OH, —$NH_2$, or —$NO_2$; and $R_{24}$, $R_{25}$ and $R_{26}$ are, independently, hydrogen, halogen, unsubstituted $C_1$-$C_6$ alkyl (preferably $C_1$-$C_3$ alkyl), unsubstituted $C_1$-$C_3$ perfluoroalkyl, unsubstituted —O—$C_1$-$C_3$ perfluoroalkyl, unsubstituted $C_1$-$C_6$ alkoxy (preferably $C_1$-$C_3$ alkoxy), —OH, —$NH_2$, —$NO_2$, —O($CH_2$)$_n$-aryl, —O($CH_2$)$_n$-heteroaryl, aryl, or heteroaryl wherein the rings of the aryl and heteroaryl groups are optionally substituted by 1 to 3 groups selected from halogen, unsubstituted $C_1$-$C_3$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —OH, —$NH_2$, or —$NO_2$.

Exemplary substituted indolymethylideneaminooxy acetic acid derivatives of the present invention include, but are not limited to, ({[(1E)-(1-allyl-5-{[4-(trifluoromethyl)benzyl]oxy}-1H-indol-3-yl)methylidene]amino}oxy)acetic acid or a pharmaceutically acceptable salt or ester form thereof; ({[(1E)-(1-ethyl-5-{[4-(trifluoromethyl)benzyl]oxy}-1H-indol-3-yl)methylidene]amino}oxy)acetic acid or a pharmaceutically acceptable salt or ester form thereof; ({[(1E)-(1-benzyl-5-{[4-(trifluoromethyl)benzyl]oxy}-1H-indol-3-yl)methylidene]amino}oxy)acetic acid or a pharmaceutically acceptable salt or ester form thereof; {[((1E)-{1-allyl-5-[(4-tert-butylbenzyl)oxy]-1H-indol-3-yl}methylidene)amino]oxy}acetic acid or a pharmaceutically acceptable salt or ester form thereof; {[((1E)-{5-[(4-tert-butylbenzyl)oxy]-1-ethyl-1H-indol-3-yl}methylidene)amino]oxy}acetic acid or a pharmaceutically acceptable salt or ester form thereof; {[((1E)-{1-benzyl-5-[(4-tert-butylbenzyl)oxy]-1H-indol-3-yl}methylidene)amino]oxy}acetic acid or a pharmaceutically acceptable salt or ester form thereof; {[((1E)-{1-allyl-5-[(4-bromobenzyl)oxy]-1H-indol-3-yl}methylidene)amino]oxy}acetic acid or a pharmaceutically acceptable salt or ester form thereof; {[((1E)-{5-[(4-bromobenzyl)oxy]-1-ethyl-1H-indol-3-yl}methylidene)amino]oxy}acetic acid or a pharmaceutically acceptable salt or ester form thereof; {[((1E)-{1-benzyl-5-[(4-bromobenzyl)oxy]-1H-indol-3-yl}methylidene)amino]oxy}acetic acid or a pharmaceutically acceptable salt or ester form thereof; ({[(1E)-(1-allyl-5-{[3,5-bis(trifluoromethyl)benzyl]oxy}-1H-indol-3-yl)methylidene]amino}oxy)acetic acid or a pharmaceutically acceptable salt or ester form thereof; ({[(1E)-(5-{[3,5-bis(trifluoromethyl)benzyl]oxy}-1-ethyl-1H-indol-3-yl)methylidene]amino}oxy)acetic acid or a pharmaceutically acceptable salt or ester form thereof; ({[(1E)-(1-benzyl-5-{[3,5-bis(trifluoromethyl)benzyl]oxy}-1H-indol-3-yl)methylidene]amino}oxy)acetic acid or a pharmaceutically acceptable salt or ester form thereof; {[((1E)-{1-allyl-5-[(3-bromobenzyl)oxy]-1H-indol-3-yl}methylidene)amino]oxy}acetic acid or a pharmaceutically acceptable salt or ester form thereof; {[((1E)-{5-[(3-bromobenzyl)oxy]-1-ethyl-1H-indol-3-yl}methylidene)amino]oxy}acetic acid or a pharmaceutically acceptable salt or ester form thereof; {[((1E)-{1-benzyl-5-[(3-bromobenzyl)oxy]-1H-indol-3-yl}methylidene)amino]oxy}acetic acid or a pharmaceutically acceptable salt or ester form thereof; {[((1E)-{1-allyl-5-[(3-chlorobenzyl)oxy]-1H-indol-3-yl}methylidene)amino]oxy}acetic acid or a pharmaceutically acceptable salt or ester form thereof; {[((1E)-{5-[(3-chlorobenzyl)oxy]-1-ethyl-1H-indol-3-yl}methylidene)amino]oxy}acetic acid or a pharmaceutically acceptable salt or ester form thereof; {[((1E)-{1-benzyl-5-[(3-chlorobenzyl)oxy]-1H-indol-3-yl}methylidene)amino]oxy}acetic acid or a pharmaceutically acceptable salt or ester form thereof; {[((1E)-{1-allyl-5-[(4-methylbenzyl)oxy]-1H-indol-3-yl}methylidene)amino]oxy}acetic acid or a pharmaceutically acceptable salt or ester form thereof; {[((1E)-{1-ethyl-5-[(4-methylbenzyl)oxy]-1H-indol-3-yl}methylidene)amino]oxy}acetic acid or a pharmaceutically acceptable salt or ester form thereof; {[((1E)-{1-benzyl-5-[(4-methylbenzyl)oxy]-1H-indol-3-yl}methylidene)amino]oxy}acetic acid or a pharmaceutically acceptable salt or ester form thereof; ({[(1E)-(1-allyl-5-{[3-(trifluoromethyl)benzyl]oxy}-1H-indol-3-yl)methylidene]amino}oxy)acetic acid or a pharmaceutically acceptable salt or ester form thereof; ({[(1E)-(1-ethyl-5-{[3-(trifluoromethyl)benzyl]oxy}-1H-indol-3-yl)methylidene]amino}oxy)acetic acid or a pharmaceutically acceptable salt or ester form thereof; ({[(1E)-(1-benzyl-5-{[3-(trifluoromethyl)benzyl]oxy}-1H-indol-3-yl)methylidene]amino}oxy)acetic acid or a pharmaceutically acceptable salt or ester form thereof; {[((1E)-{1-allyl-5-[(3-methylbenzyl)oxy]-1H-indol-3-yl}methylidene)amino]oxy}acetic acid or a pharmaceutically acceptable salt or ester form thereof; {[((1E)-{1-ethyl-5-[(3-methylbenzyl)oxy]-1H-indol-3-yl}methylidene)amino]oxy}acetic acid or a pharmaceutically acceptable salt or ester form thereof; {[((1E)-{1-benzyl-5-[(3-methylbenzyl)oxy]-1H-indol-3-yl}methylidene)amino]oxy}acetic acid or a pharmaceutically acceptable salt or ester form thereof; {[((1E)-{5-[(2-chlorobenzyl)oxy]-1-ethyl-1H-indol-3-yl}methylidene)amino]oxy}acetic acid or ester form thereof; {[((1E)-{1-benzyl-5-[(2-chlorobenzyl)oxy]-1H-indol-3-yl}methylidene)amino]oxy}acetic acid or a pharmaceutically acceptable salt or ester form thereof; {[((1E)-{5-[(2-chlorobenzyl)oxy]-1H-indol-3-yl}methylidene)amino]oxy}acetic acid or a pharmaceutically acceptable salt or ester form thereof; ({[(1E)-(1-(2-propynyl)-5-{[4-(trifluoromethyl)benzyl]oxy}-1H-indol-3-yl)methylidene]amino}oxy)acetic acid or a pharmaceutically acceptable salt or ester form thereof; ({[(1E)-(1-methyl-5-{[4-(trifluoromethyl)benzyl]oxy}-1H-indol-3-yl)methylidene]amino}oxy)acetic acid or a pharmaceutically acceptable salt or ester form thereof; [({(1E)-[5-[(4-tert-butylbenzyl)oxy]-1-(2-propynyl)-1H-indol-3-yl]methylidene}amino)oxy]acetic acid or a pharmaceutically acceptable salt or ester form thereof; {[((1E)-{5-[(4-tert-butylbenzyl)oxy]-1-methyl-1H-indol-3-yl}methylidene)amino]oxy}acetic acid or a pharmaceutically acceptable salt or ester form thereof; [({(1E)-[5-{[3,5-bis(trifluoromethyl)benzyl]oxy}-1-(2-propynyl)-1H-indol-3-yl]methylidene}amino)oxy]acetic acid or a pharmaceutically acceptable salt or ester form thereof; [({(1E)-[5-[(3-bromobenzyl)oxy]-1-(2-propynyl)-1H-indol-3-yl]methylidene}amino)oxy]acetic acid or a pharmaceutically acceptable salt or ester form thereof; {[((1E)-{5-[(3-bromobenzyl)oxy]-1-methyl-1H-indol-3-yl}methylidene)amino]oxy}acetic acid or a pharmaceutically acceptable salt or ester form thereof; [({(1E)-[5-[(3-chlorobenzyl)oxy]-1-(2-propynyl)-1H-indol-3-yl]methylidene}amino)oxy]acetic acid or a pharmaceutically acceptable salt or ester form thereof; {[((1E)-{5-[(3-chlorobenzyl)oxy]-1-methyl-1H-indol-3-yl}methylidene)amino]oxy}acetic acid or a pharmaceutically acceptable salt or ester form thereof; [({(1E)-[1-allyl-5-(benzyloxy)-1H-indol-3-yl]methylidene}amino)oxy]acetic acid or a pharmaceutically acceptable salt or ester form thereof; [({(1E)-[1-benzyl-5-(benzyloxy)-1H-indol-3-yl]methylidene}amino)oxy]acetic acid or a pharmaceutically acceptable salt or ester form thereof; ({[(1E)-(1-(2-propynyl)-5-{[3-(trifluoromethyl)benzyl]oxy}-1H-indol-3-yl)methylidene]amino}oxy)acetic acid or a pharmaceutically acceptable salt or ester form thereof; ({[(1E)-(1-methyl-5-{[3-(trifluoromethyl)benzyl]oxy}-1H-indol-3-yl)methylidene]amino}oxy)acetic acid or a pharmaceutically acceptable salt or ester form thereof; [({(1E)-[5-[(4-chlorobenzyl)oxy]-1-(2-propynyl)-1H-indol-3-yl]methylidene}amino oxy]acetic acid or a pharmaceutically acceptable salt or ester form thereof; {[((1E)-{1-allyl-5-[(4-chlorobenzyl)oxy]-1H-indol-3-yl}methylidene)amino]oxy}acetic acid or a pharmaceutically acceptable salt or ester form thereof; {[((1E)-{1-benzyl-5-[(4-chlorobenzyl)oxy]-1H-indol-3-yl}methylidene)amino]oxy}acetic acid or a pharmaceutically acceptable salt or ester form thereof; {[((1E)-{5-[(4-chlorobenzyl)oxy]-1-methyl-1H-indol-3-yl}methylidene)amino]oxy}acetic acid or a pharmaceutically acceptable salt or ester form thereof; [({(1E)-5-[(2-chlorobenzyl)oxy]-1-(2-propynyl)-1H-indol-3-yl]methylidene}amino)oxy]acetic acid or a pharmaceutically acceptable salt or ester form thereof; {[((1E)-{1-allyl-5-[(2-chlorobenzyl)oxy]-1H-indol-3-yl}methylidene)amino]oxy}acetic acid or a pharmaceutically acceptable salt or ester form thereof; {[((1E)-{5-[(2-chlorobenzyl)oxy]-1-methyl-1H-indol-3-yl}methylidene)amino]oxy}acetic acid or a pharmaceutically acceptable salt or ester form thereof; [({(1E)-[5-[(3,4-dichlorobenzyl)oxy]-1-(2-propynyl)-1H-indol-3-yl]methylidene}amino)oxy]acetic acid or a pharmaceutically acceptable salt or ester form thereof; {[((1E)-{1-allyl-5-[(3,4-dichlorobenzyl)oxy]-1H-indol-3-yl}methylidene)amino]oxy}acetic acid or a pharmaceutically acceptable salt or ester form thereof; {[((1E)-{1-benzyl-5-[(3,4-dichlorobenzyl)oxy]-1H-indol-3-yl}methylidene)amino]oxy}acetic acid or a pharmaceutically acceptable salt or ester form thereof; {[((1E)-{5-[(3,4-dichlorobenzyl)oxy]-1-methyl-1H-indol-3-yl}methylidene)amino]oxy}acetic acid or a pharmaceutically acceptable salt or ester form thereof; [({(1E)-[1-allyl-5-(2-naphthylmethoxy)-1H-indol-3-yl]methylidene}amino)oxy]acetic acid or a pharmaceutically acceptable salt or ester form thereof; [({(1E)-[1-benzyl-5-(2-naphthylmethoxy)-1H-indol-3-yl]methylidene}amino)oxy]acetic acid or a pharmaceutically acceptable salt or ester form thereof; and [({(1E)-[1-methyl-5-(2-naphthylmethoxy)-1H-indol-3-yl]methylidene}amino)oxy]acetic acid or a pharmaceutically acceptable salt or ester form thereof.

In alternative embodiments of the present invention, acetic acid derivatives include biphenylmethylidene aminooxy acetic acid derivatives of the following formula:

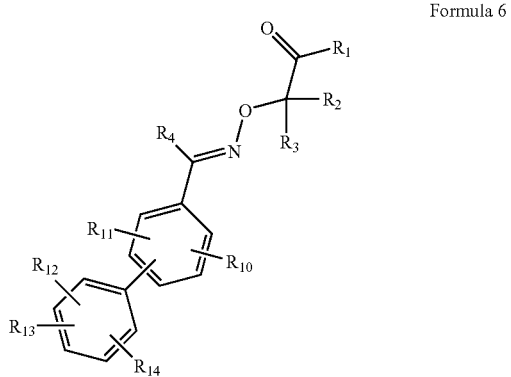

Formula 6 wherein $R_1$, $R_2$, $R_3$, $R_4$, $R_{10}$, $R_{11}$, $R_{12}$, $R_{13}$, $R_{14}$, and n are defined as above for Formula 1.

Compounds of the present invention also include prodrugs, stereoisomers, or pharmaceutically acceptable salt or ester forms of Formula 6.

In certain compounds of Formula 6, $R_1$ is —$OC_1$-$C_6$ alkyl or —OH. In certain preferred embodiments, $R_1$ is —OH. In such embodiments, $R_2$, $R_3$, $R_4$, $R_{10}$, $R_{11}$, $R_{12}$, $R_{13}$, $R_{14}$, and n are as defined herein for compounds of Formula 6.

In certain compounds of Formula 6, $R_2$ and $R_3$ are, independently, $CH_2$—$C_3$-$C_6$ cycloalkyl, —$CH_2$-pyridinyl, or benzyl wherein the rings of the cycloalkyl, pyridinyl, and benzyl groups are optionally substituted by 1 to 3 groups selected from halogen, $C_1$-$C_3$ alkyl, $C_1$-$C_3$ perfluoroalkyl, —O—$C_1$-$C_3$ perfluoroalkyl, $C_1$-$C_3$ alkoxy, —OH, —$NH_2$, —CN, or —$NO_2$. In other embodiments, $R_2$ and $R_3$ are, independently, alkyl or hydrogen. In certain preferred embodiments, $R_2$ and $R_3$ are hydrogen. In such embodiments, $R_1$, $R_4$, $R_{10}$, $R_{11}$, $R_{12}$, $R_{13}$, $R_{14}$, and n are as defined herein for compounds of Formula 6.

In certain compounds of Formula 6, $R_4$ is $C_3$-$C_6$ cycloalkyl, $CH_2$—$C_3$-$C_6$ cycloalkyl, pyridinyl, —$CH_2$-pyridinyl, phenyl or benzyl wherein the rings of the cycloalkyl, pyridinyl, phenyl, and benzyl groups are optionally substituted by 1 to 3 groups selected from halogen, $C_1$-$C_3$ alkyl, $C_1$-$C_3$ perfluoroalkyl, —O—$C_1$-$C_3$ perfluoroalkyl, $C_1$-$C_3$ alkoxy, —OH, —$NH_2$, or —$NO_2$. In other embodiments, $R_4$ and $R_5$ are, independently, alkyl or hydrogen. In certain preferred embodiments, $R_4$ is hydrogen. In such embodiments, $R_1$, $R_2$, $R_3$, $R_{10}$, $R_{11}$, $R_{12}$, $R_{13}$, $R_{14}$, and n are as defined herein for compounds of Formula 6.

$R_{10}$, $R_{11}$, $R_{12}$, $R_{13}$ and $R_{14}$ can be hydrogen, halogen, $C_1$-$C_6$ alkyl, $C_1$-$C_3$ perfluoroalkyl, —O—$C_1$-$C_3$ perfluoroalkyl, $C_1$-$C_3$ alkoxy, —OH, —$NH_2$, —$NO_2$, —$O(CH_2)_n$-aryl, —$O(CH_2)_n$-heteroaryl, aryl, or heteroaryl.

In certain compounds of Formula 6, $R_{10}$ and $R_{11}$ are, independently, aryl, $O(CH_2)_n$-aryl, heteroaryl, or $O(CH_2)_n$-heteroaryl wherein the rings of the aryl and heteroaryl groups are optionally substituted by 1 to 3 groups selected from halogen, $C_1$-$C_3$ alkyl, $C_1$-$C_3$ perfluoroalkyl, —O—$C_1$-$C_3$ perfluoralkyl, $C_1$-$C_3$ alkoxy, —OH, —$NH_2$, or —$NO_2$. In other embodiments, $R_{10}$ and $R_{11}$ are, independently, $C_1$-$C_6$ alkyl, halogen, $C_1$-$C_3$ alkyl, $C_1$-$C_3$ perfluoroalkyl, —O—$C_1$-$C_3$ perfluoralkyl, or $C_1$-$C_3$ alkoxy. In certain preferred embodiments, $R_{10}$ and $R_{11}$ are hydrogen. In such embodiments, $R_1$, $R_2$, $R_3$, $R_4$, $R_{12}$, $R_{13}$, $R_{14}$, and n are as defined herein for compounds of Formula 6.

In certain compounds of Formula 6, $R_{12}$, $R_{13}$ and $R_{14}$ are, independently, aryl, $O(CH_2)_n$-aryl, heteroaryl, or $O(CH_2)_n$-heteroaryl wherein the rings of the aryl and heteroaryl groups are optionally substituted by 1 to 3 groups selected from halogen, $C_1$-$C_3$ alkyl, $C_1$-$C_3$ perfluoroalkyl, —O—$C_1$-$C_3$ perfluoralkyl, $C_1$-$C_3$ alkoxy, —OH, —$NH_2$, or —$NO_2$. In certain preferred embodiments, $R_{12}$, $R_{13}$ and $R_{14}$ are, independently, hydrogen, $C_1$-$C_6$ alkyl, halogen, $C_1$-$C_3$ alkyl, $C_1$-$C_3$ perfluoroalkyl, —O—$C_1$-$C_3$ perfluoralkyl, or $C_1$-$C_3$ alkoxy. More preferably $R_{12}$, $R_{13}$ and $R_{14}$ are, independently hydrogen or —$O(CH_2)_n$-aryl wherein the ring of the aryl group is optionally substituted with 1 to 3 groups selected from alkyl, perfluoralkyl, halogen, or aryl. For example, in some embodiments, $R_{12}$, $R_{13}$ and $R_{14}$ are, independently hydrogen or benzyloxy wherein the benzyl group is optionally substituted with 1 to 3 groups selected from butyl, $CF_3$, bromine, chlorine, methyl, and naphthyl. In such embodiments, $R_1$, $R_2$, $R_3$, $R_4$, $R_{10}$, $R_{11}$, and n are as defined herein for compounds of Formula 6.

In certain embodiments of the present invention, such biphenylmethylidene aminooxy acetic acid derivatives include the following compounds:

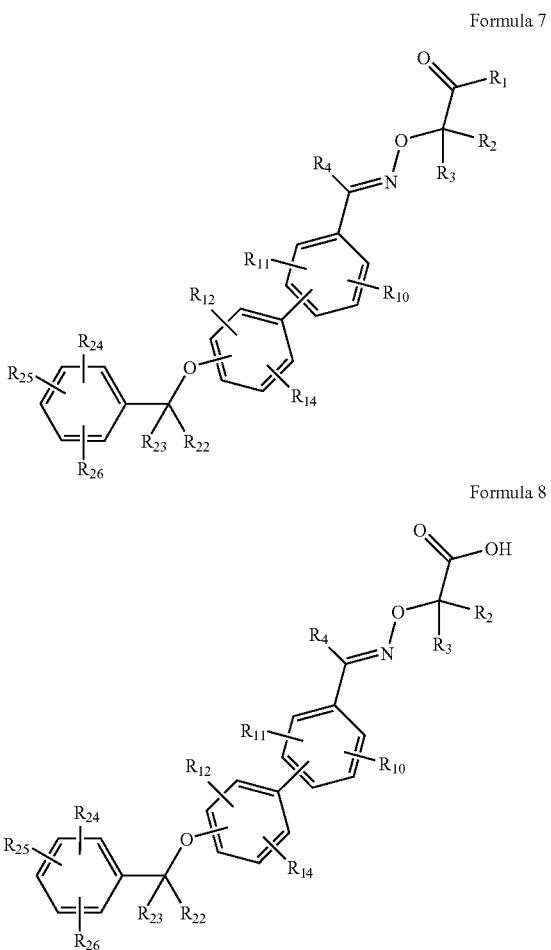

Formula 7

Formula 8 wherein $R_1$, $R_2$, $R_3$, $R_4$, $R_{10}$, $R_{11}$, $R_{12}$, $R_{13}$, $R_{14}$, $R_{22}$, $R_{23}$, $R_{24}$, $R_{25}$, $R_{26}$ and n are defined as above for Formulas 1 and Formulas 3-5.

In certain preferred embodiments of the present invention, $R_1$ is —OH, unsubstituted —$OC_1$-$C_8$ alkyl, or $NH_2$;

$R_2$ and $R_3$ are, independently, hydrogen, unsubstituted $C_1$-$C_8$ alkyl, —$CH_2$—$C_3$-$C_6$ cycloalkyl, —$CH_2$-pyridinyl, phenyl, or benzyl wherein the rings of the cycloalkyl, pyridinyl, phenyl, or benzyl groups are optionally substituted by 1 to 3 groups selected from halogen, unsubstituted $C_1$-$C_3$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —CN, —OH, —$NH_2$, or —$NO_2$;

$R_4$ is hydrogen, unsubstituted $C_1$-$C_8$ alkyl, $C_3$-$C_6$ cycloalkyl, —$CH_2$—$C_3$-$C_6$ cycloalkyl, phenyl, benzyl, pyridinyl, or —$CH_2$-pyridinyl wherein the rings of the cycloalkyl, pyridinyl, phenyl, or benzyl groups are optionally substituted by 1 to 3 groups selected from halogen, unsubstituted $C_1$-$C_3$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —OH, —$NH_2$, or —$NO_2$;

$R_{10}$, $R_{11}$, $R_{12}$, $R_{13}$ and $R_{14}$ are, independently, hydrogen, halogen, unsubstituted $C_1$-$C_6$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —OH, —$NH_2$, —$NO_2$, —$O(CH_2)_n$-aryl, —$O(CH_2)_n$-heteroaryl, aryl, or heteroaryl wherein the rings of the aryl and heteroaryl groups are optionally substituted by 1 to 3 groups selected from halogen, unsubstituted $C_1$-$C_3$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —OH, —$NH_2$, or —$NO_2$;

$R_{22}$ and $R_{23}$ are, independently, hydrogen, unsubstituted $C_1$-$C_8$ alkyl, —$CH_2$—$C_3$-$C_6$ cycloalkyl, —$CH_2$-pyridinyl, phenyl, or benzyl wherein the rings of the cycloalkyl, pyridinyl, phenyl and benzyl groups are optionally substituted by 1 to 3 groups selected from halogen, unsubstituted $C_1$-$C_3$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —OH, —$NH_2$, or —$NO_2$; and $R_{24}$, $R_{25}$ and $R_{26}$ are, independently, hydrogen, halogen, unsubstituted $C_1$-$C_6$ alkyl (preferably $C_1$-$C_3$ alkyl), unsubstituted $C_1$-$C_3$ perfluoroalkyl, unsubstituted —O—$C_1$-$C_3$ perfluoroalkyl, unsubstituted $C_1$-$C_6$ alkoxy (preferably $C_1$-$C_3$ alkoxy), —OH, —$NH_2$, —$NO_2$, —$O(CH_2)_n$-aryl, —$O(CH_2)_n$-heteroaryl, aryl, or heteroaryl wherein the rings of the aryl and heteroaryl groups are optionally substituted by 1 to 3 groups selected from halogen, unsubstituted $C_1$-$C_3$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —OH, —$NH_2$, or —$NO_2$.

Exemplary substituted biphenylmethylidene aminooxy acetic acid derivatives of the present invention include, but are not limited to, ({[(1E)-(3'-{[4-(trifluoromethyl)benzyl]oxy}-1,1'-biphenyl-3-yl)methylidene]amino}oxy)acetic acid or a pharmaceutically acceptable salt or ester form thereof; {[((1E)-{3'-[(4-tert-butylbenzyl)oxy]-1,1'-biphenyl-3-yl}methylidene)amino]oxy}acetic acid or a pharmaceutically acceptable salt or ester form thereof; {[((1E)-{3'-[(4-bromobenzyl)oxy]-1,1'-biphenyl-3-yl}methylidene)amino]oxy}acetic acid or a pharmaceutically acceptable salt or ester form thereof; ({[(1E)-(3'-{[3,5-bis(trifluoromethyl)benzyl]oxy}-1,1'-biphenyl-3-yl)methylidene]amino}oxy)acetic acid or a pharmaceutically acceptable salt or ester form thereof; {[((1E)-{3'-[(3-bromobenzyl)oxy]-1,1'-biphenyl-3-yl}methylidene)amino]oxy}acetic acid or a pharmaceutically acceptable salt or ester form thereof; {[((1E)-{3'-[(3-chlorobenzyl)oxy]-1,1'-biphenyl-3-yl}methylidene)amino]oxy}acetic acid or a pharmaceutically acceptable salt or ester form thereof; [({(1E)-[3'-(benzyloxy)-1,1'-biphenyl-3-yl]methylidene}amino)oxy]acetic acid or a pharmaceutically acceptable salt or ester form thereof; ({[(1E)-(3'-{[3-(trifluoromethyl)benzyl]oxy}-1,1'-biphenyl-3-yl)methylidene]amino}oxy)acetic acid or a pharmaceutically acceptable salt or ester form thereof; {[((1E)-{3'-[(4-chlorobenzyl)oxy]-1,1'-biphenyl-3-yl}methylidene)amino]oxy}acetic acid or a pharmaceutically acceptable salt or ester form thereof; {[((1E)-{3'-[(2-chlorobenzyl)oxy]-1,1'-biphenyl-3-yl}methylidene)amino]oxy}acetic acid or a pharmaceutically acceptable salt or ester form thereof; {[((1E)-{3'-[(3,4-dichlorobenzyl)oxy]-1,1'-biphenyl-3-yl}methylidene)amino]oxy}acetic acid or a pharmaceutically acceptable salt or ester form thereof; [({(1E)-[3'-(2-naphthylmethoxy)-1,1'-biphenyl-3-yl]methylidene}amino)oxy]acetic acid or a pharmaceutically acceptable salt or ester form thereof; {[((1E)-{3'-[(4-methylbenzyl)oxy]-1,1'-biphenyl-3-yl}methylidene)amino]oxy}acetic acid or a pharmaceutically acceptable salt or ester form thereof; {[((1E)-{3'-[(3-methylbenzyl)oxy]-1,1'-biphenyl-3-yl}methylidene)amino]oxy}acetic acid or a pharmaceutically acceptable salt or ester form thereof; {[((1E)-{3'-[(2,6-dichlorobenzyl)oxy]-1,1'-biphenyl-3-yl}methylidene)amino]oxy}acetic acid or a pharmaceutically acceptable salt or ester form thereof; ({[(1E)-(4'-{[4-(trifluoromethyl)benzyl]oxy}-1,1'-biphenyl-3-yl)methylidene]amino}oxy)acetic acid or a pharmaceutically acceptable salt or ester form thereof; {[((1E)-{4'-[(4-tert-butylbenzyl)oxy]-1,1'-biphenyl-3-yl}methylidene)amino]oxy}acetic acid or a pharmaceutically acceptable salt or ester form thereof; {[((1E)-{4'-[(4-bromobenzyl)oxy]-1,1'-biphenyl-3-yl}methylidene)amino]oxy}acetic acid or a pharmaceutically acceptable salt or ester form thereof; ({[(1E)-(4'-{[3,5-bis(trifluoromethyl)benzyl]oxy}-1,1'-biphenyl-3-yl)methylidene]amino}oxy)acetic acid or a pharmaceutically acceptable salt or ester form thereof; {[((1E)-{4'-[(3-bromobenzyl)oxy]-1,1'-biphenyl-3-yl}methylidene)amino]oxy}acetic acid or a pharmaceutically acceptable salt or ester form thereof; {[((1E)-{4'-[(3-chlorobenzyl)oxy]-1,1'-biphenyl-3-yl}methylidene)amino]oxy}acetic acid or a pharmaceutically acceptable salt or ester form thereof; [({(1E)-[4'-(benzyloxy)-1,1'-biphenyl-3-yl]methylidene}amino)oxy]acetic acid or a pharmaceutically acceptable salt or ester form thereof; ({[(1E)-(4'-{[3-(trifluoromethyl)benzyl]oxy}-1,1'-biphenyl-3-yl)methylidene]amino}oxy)acetic acid or a pharmaceutically acceptable salt or ester form thereof; {[((1E)-{4'-[(4-chlorobenzyl)oxy]-1,1'-biphenyl-3-yl}methylidene)amino]oxy}acetic acid or a pharmaceutically acceptable salt or ester form thereof; {[((1E)-{4'-[(2-chlorobenzyl)oxy]-1,1'-biphenyl-3-yl}methylidene)amino]oxy}acetic acid or a pharmaceutically acceptable salt or ester form thereof; {[((1E)-{4'-[(3,4-dichlorobenzyl)oxy]-1,1'-biphenyl-3-yl}methylidene)amino]oxy}acetic acid or a pharmaceutically acceptable salt or ester form thereof; [({(1E)-[4'-(2-naphthylmethoxy)-1,1'-biphenyl-3-yl]methylidene}amino)oxy]acetic acid or a pharmaceutically acceptable salt or ester form thereof; {[((1E)-{4'-[(4-methylbenzyl)oxy]-1,1'-biphenyl-3-yl}methylidene)amino]oxy}acetic acid or a pharmaceutically acceptable salt or ester form thereof; {[((1E)-{4'-[(3-methylbenzyl)oxy]-1,1'-biphenyl-3-yl}methylidene)amino]oxy}acetic acid or a pharmaceutically acceptable salt or ester form thereof; {[((1E)-{4'-[(2,6-dichlorobenzyl)oxy]-1,1'-biphenyl-3-yl}methylidene)amino]oxy}acetic acid or a pharmaceutically acceptable salt or ester form thereof; ({[(1E)-(3'-{[4-(trifluoromethyl)benzyl]oxy}-1,1'-biphenyl-4-yl)methylidene]amino}oxy)acetic acid or a pharmaceutically acceptable salt or ester form thereof; {[((1E)-{3'-[(4-tert-butylbenzyl)oxy]-1,1'-biphenyl-4-yl}methylidene)amino]oxy}acetic acid or a pharmaceutically acceptable salt or ester form thereof; ({[(1E)-(3'-{[3,5-bis(trifluoromethyl)benzyl]oxy}-1,1'-biphenyl-4-yl)methylidene]amino}oxy)acetic acid or a pharmaceutically acceptable salt or ester form thereof; {[((1E)-{3'-[(3-bromobenzyl)oxy]-1,1'-biphenyl-4-yl}methylidene)amino]oxy}acetic acid or a pharmaceutically acceptable salt or ester form thereof; {[((1E)-{3'-[(3-chlorobenzyl)oxy]-1,1'-biphenyl-4-yl}methylidene)amino]oxy}acetic acid or a pharmaceutically acceptable salt or ester form thereof; [({(1E)-[3'-(benzyloxy)-1,1'-biphenyl-4-yl]methylidene}amino)oxy]acetic acid or a pharmaceutically acceptable salt or ester form thereof; ({[(1E)-(3'-{[3-(trifluoromethyl)benzyl]oxy}-1,1'-biphenyl-4-yl)methylidene]amino}oxy)acetic acid or a pharmaceutically acceptable salt or ester form thereof; {[((1E)-{3'-[(4-chlorobenzyl)oxy]-1,1'-biphenyl-4-yl}methylidene)amino]oxy}acetic acid or a pharmaceutically acceptable salt or ester form thereof; {[((1E)-{3'-[(2-chlorobenzyl)oxy]-1,1'-biphenyl-4-yl}methylidene)amino]oxy}acetic acid or a pharmaceutically acceptable salt or ester form thereof; {[((1E)-{3'-[(3,4-dichlorobenzyl)oxy]-1,1'-biphenyl-4-yl}methylidene)amino]oxy}acetic acid or a pharmaceutically acceptable salt or ester form thereof; [({(1E)-[3'-(2-naphthylmethoxy)-1,1'-biphenyl-4-yl]methylidene}amino)oxy]acetic acid or a pharmaceutically acceptable salt or ester form thereof; {[((1E)-{3'-[(4-methylbenzyl)oxy]-1,1'-biphenyl-4-yl}methylidene)amino]oxy}acetic acid or a pharmaceutically acceptable salt or ester form thereof; {[((1E)-{3'-[(3-methylbenzyl)oxy]-1,1'-biphenyl-4-yl}methylidene)amino]oxy}acetic acid or a pharmaceutically acceptable salt or ester form thereof; {[((1E)-{3'-[(2,6-dichlorobenzyl)oxy]-1,1'-biphenyl-4-yl}methylidene)amino]oxy}acetic acid or a pharmaceutically acceptable salt or ester form thereof; {[((1E)-{4'-[(4-tert-butylbenzyl)oxy]-1,1'-biphenyl-4-yl}methylidene)amino]oxy}acetic acid or a pharmaceutically acceptable salt or ester form thereof; {[((1E)-{4'-[(3-bromobenzyl)oxy]-1,1'-biphenyl-4-yl}methylidene)amino]oxy}acetic acid or a pharmaceutically acceptable salt or ester form thereof; {[((1E)-{4'-[(3-chlorobenzyl)oxy]-1,1'-biphenyl-4-yl}methylidene)amino]oxy}acetic acid or a pharmaceutically acceptable salt or ester form thereof; [({(1E)-[4'-(benzyloxy)-1,1'-biphenyl-4-yl]methylidene}amino)oxy]acetic acid or a pharmaceutically acceptable salt or ester form thereof; ({[(1E)-(4'-{[3-(trifluoromethyl)benzyl]oxy}-1,1'-biphenyl-4-yl)methylidene]amino}oxy)acetic acid or a pharmaceutically acceptable salt or ester form thereof; {[((1E)-{4'-[(2-chlorobenzyl)oxy]-1,1'-biphenyl-4-yl}methylidene)amino]oxy}acetic acid or a pharmaceutically acceptable salt or ester form thereof; {[((1E)-{4'-[(3,4-dichlorobenzyl)oxy]-1,1'-biphenyl-4-yl}methylidene)amino]oxy}acetic acid or a pharmaceutically acceptable salt or ester form thereof; {[((1E)-{4'-[(4-methylbenzyl)oxy]-1,1'-biphenyl-4-yl}methylidene)amino]oxy}acetic acid or a pharmaceutically acceptable salt or ester form thereof; {[((1E)-{4'-[(3-methylbenzyl)oxy]-1,1'-biphenyl-4-yl}methylidene)amino]oxy}acetic acid or a pharmaceutically acceptable salt or ester form thereof; and {[((1E)-{4'-[(2,6-dichlorobenzyl)oxy]-1,1'-biphenyl-4-yl}methylidene)amino]oxy}acetic acid or a pharmaceutically acceptable salt or ester form thereof.

In alternative embodiments of the present invention, substituted acetic acid derivatives include substituted bisbenzyloxyphenylmethylidene aminooxy acetic acid derivatives off the following formula:

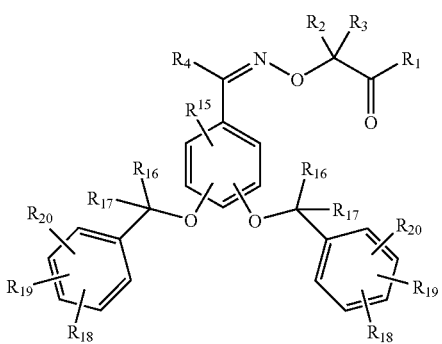

Formula 9 wherein $R_1$, $R_2$, $R_3$, $R_4$, $R_{15}$, $R_{16}$, $R_{17}$, $R_{18}$, $R_{19}$, $R_{20}$, and n are defined as above for Formula 1.

Compounds of the present invention also include prodrugs, stereoisomers, or pharmaceutically acceptable salt or ester forms of Formula 9.

In certain compounds of Formula 9, $R_1$ is $-OC_1-C_6$ alkyl or $-OH$. In certain preferred embodiments, $R_1$ is $-OH$. In such embodiments, $R_2$, $R_3$, $R_4$, $R_{15}$, $R_{16}$, $R_{17}$, $R_{18}$, $R_{19}$, $R_{20}$, and n are as defined herein for compounds of Formula 9.

In certain compounds of Formula 9, $R_2$ and $R_3$ are, independently, $CH_2-C_3-C_6$ cycloalkyl, $-CH_2$-pyridinyl, or benzyl wherein the rings of the cycloalkyl, pyridinyl, and benzyl groups are optionally substituted by 1 to 3 groups selected from halogen, $C_1$-$C_3$ alkyl, $C_1$-$C_3$ perfluoroalkyl, —O—$C_1$-$C_3$ perfluoroalkyl, $C_1$-$C_3$ alkoxy, —OH, —$NH_2$, —CN, or —$NO_2$. In other embodiments, $R_2$ and $R_3$ are, independently, alkyl or hydrogen. In certain preferred embodiments, $R_2$ and $R_3$ are hydrogen. In such embodiments, $R_1$, $R_4$, $R_{15}$, $R_{16}$, $R_{17}$, $R_{18}$, $R_{19}$, $R_{20}$, and n are as defined herein for compounds of Formula 9.

In certain compounds of Formula 9, $R_4$ is $C_3$-$C_6$ cycloalkyl, $CH_2$—$C_3$-$C_6$ cycloalkyl, pyridinyl, —$CH_2$-pyridinyl, phenyl or benzyl wherein the rings of the cycloalkyl, pyridinyl, phenyl, and benzyl groups are optionally substituted by 1 to 3 groups selected from halogen, $C_1$-$C_3$ alkyl, $C_1$-$C_3$ perfluoroalkyl, —O—$C_1$-$C_3$ perfluoroalkyl, $C_1$-$C_3$ alkoxy, —OH, —$NH_2$, or —$NO_2$. In other embodiments, $R_4$ is alkyl or hydrogen. In certain preferred embodiments, $R_4$ is hydrogen. In such embodiments, $R_1$, $R_2$, $R_3$, $R_4$, $R_{15}$, $R_{16}$, $R_{17}$, $R_{18}$, $R_{19}$, $R_{20}$, and n are as defined herein for compounds of Formula 9.

$R_{16}$ and $R_{17}$ can be hydrogen, $C_1$-$C_8$ alkyl, $C_3$-$C_6$ cycloalkyl, —$CH_2$—$C_3$-$C_6$ cycloalkyl, aryl, benzyl, heteroaryl, or —$CH_2$-heteroaryl. In certain compounds of Formula 9, $R_{16}$ and $R_{17}$ are, independently, $C_3$-$C_6$ cycloalkyl, $CH_2$—$C_3$-$C_6$ cycloalkyl, pyridinyl, —$CH_2$-pyridinyl or benzyl wherein the rings of the cycloalkyl, pyridinyl, and benzyl groups are optionally substituted by 1 to 3 groups selected from halogen, $C_1$-$C_3$ alkyl, $C_1$-$C_3$ perfluoroalkyl, —O—$C_1$-$C_3$ perfluoroalkyl, $C_1$-$C_3$ alkoxy, —OH, —$NH_2$, or —$NO_2$. In other embodiments, $R_{16}$ and $R_{17}$ are, independently, alkyl or hydrogen. In certain preferred embodiments, $R_{16}$ and $R_{17}$ are hydrogen. In such embodiments, $R_1$, $R_2$, $R_3$, $R_{15}$, $R_{18}$, $R_{19}$, $R_{20}$, and n are as defined herein for compounds of Formula 9

$R_{15}$, $R_{18}$, $R_{19}$ and $R_{20}$ can be hydrogen, halogen, $C_1$-$C_6$ alkyl, $C_1$-$C_3$ perfluoroalkyl, —O—$C_1$-$C_3$ perfluoroalkyl, $C_1$-$C_3$ alkoxy, —OH, —$NH_2$, —$NO_2$, —$O(CH_2)_n$-aryl, —$O(CH_2)_n$-heteroaryl, aryl, or heteroaryl. In certain compounds of Formula 9, $R_{15}$ is aryl, $O(CH_2)_n$-aryl, heteroaryl, or $O(CH_2)_n$-heteroaryl wherein the rings of the aryl and heteroaryl groups are optionally substituted by 1 to 3 groups selected from halogen, $C_1$-$C_3$ alkyl, $C_1$-$C_3$ perfluoroalkyl, —O—$C_1$-$C_3$ perfluoralkyl, $C_1$-$C_3$ alkoxy, —OH, —$NH_2$, or —$NO_2$. In other embodiments $R_{15}$ is hydrogen, $C_1$-$C_6$ alkyl, $C_1$-$C_3$ perfluoroalkyl, —O—$C_1$-$C_3$ perfluoralkyl, or $C_1$-$C_3$ alkoxy. In certain preferred embodiments, $R_{15}$ is hydrogen. In such embodiments, $R_1$, $R_2$, $R_3$, $R_4$, $R_{16}$, $R_{17}$, $R_{18}$, $R_{19}$, and $R_{20}$ and n are as defined herein for compounds of Formula 9.

In certain compounds of Formula 9, $R_{18}$, $R_{19}$, and $R_{20}$ are, independently, aryl, $O(CH_2)_n$-aryl, heteroaryl, or $O(CH_2)_n$-heteroaryl wherein the rings of the aryl and heteroaryl groups are optionally substituted by 1 to 3 groups selected from halogen, $C_1$-$C_3$ alkyl, $C_1$-$C_3$ perfluoroalkyl, —O—$C_1$-$C_3$ perfluoralkyl, $C_1$-$C_3$ alkoxy, —OH, —$NH_2$, or —$NO_2$. In certain embodiments, $R_{18}$, $R_{19}$, and $R_{20}$ are, independently, hydrogen, $C_1$-$C_6$ alkyl, $C_1$-$C_3$ perfluoroalkyl, —O—$C_1$-$C_3$ perfluoralkyl, or $C_1$-$C_3$ alkoxy. For example, in some embodiments, $R_{18}$, $R_{19}$, and $R_{20}$ are, independently hydrogen, methyl, butyl, $CF_3$, chlorine, or bromine. In such embodiments, $R_1$, $R_2$, $R_3$, $R_4$, $R_{15}$, $R_{17}$, and n are as defined herein for compounds of Formula 9.

In certain embodiments, such substituted bisbenzyloxyphenylmethylidene aminooxy acetic acid derivatives include the following compounds:

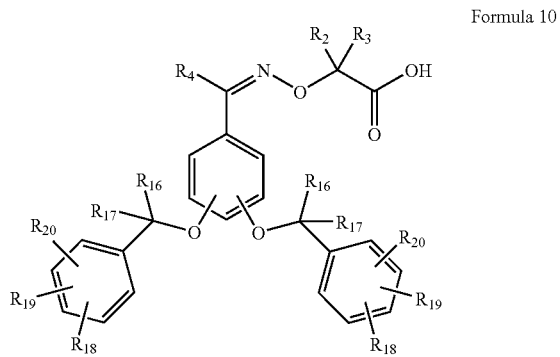
Formula 10 wherein $R_1$, $R_2$, $R_3$, $R_4$, $R_{15}$, $R_{16}$, $R_{17}$, $R_{18}$, $R_{19}$, $R_{20}$, and n are defined as above for Formula 1.

In certain embodiments of the present invention, $R_1$ is —OH, unsubstituted —$OC_1$-$C_8$ alkyl, or $NH_2$;

$R_2$ and $R_3$ are, independently, hydrogen, unsubstituted $C_1$-$C_8$ alkyl, —$CH_2$—$C_3$-$C_6$ cycloalkyl, —$CH_2$-pyridinyl, phenyl, or benzyl wherein the rings of the cycloalkyl, pyridinyl, phenyl, or benzyl groups are optionally substituted by 1 to 3 groups selected from halogen, unsubstituted $C_1$-$C_3$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —OH, —CN, —$NH_2$, or —$NO_2$;

$R_4$ is hydrogen, unsubstituted $C_1$-$C_8$ alkyl, $C_3$-$C_6$ cycloalkyl, —$CH_2$—$C_3$-$C_6$ cycloalkyl, phenyl, benzyl, pyridinyl, or —$CH_2$-pyridinyl wherein the rings of the cycloalkyl, pyridinyl, phenyl, or benzyl groups are optionally substituted by 1 to 3 groups selected from halogen, unsubstituted $C_1$-$C_3$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —OH, —$NH_2$, or —$NO_2$;

$R_{16}$ and $R_{17}$ are, independently, hydrogen, unsubstituted $C_1$-$C_8$ alkyl, $C_3$-$C_6$ cycloalkyl, —$CH_2$—$C_3$-$C_6$ cycloalkyl, aryl, benzyl, heteroaryl, or —$CH_2$-heteroaryl wherein the reigns of the aryl and heteroaryl groups are optionally substituted by 1 to 3 groups selected from halogen, unsubstituted $C_1$-$C_3$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —OH, —$NH_2$, or —$NO_2$;

$R_{15}$, $R_{18}$, $R_{19}$ and $R_{20}$ are, independently, hydrogen, halogen, unsubstituted $C_1$-$C_6$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —OH, —$NH_2$, —$NO_2$, —$O(CH_2)_n$-aryl, —$O(CH_2)_n$-heteroaryl, aryl, or heteroaryl wherein the rings of the aryl and heteroaryl groups are optionally substituted by 1 to 3 groups selected from halogen, unsubstituted $C_1$-$C_3$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —OH, —$NH_2$, or —$NO_2$.

Exemplary bisbenzyloxyphenylmethylidene aminooxy acetic acid derivatives include, but are not limited to, {[((1E)-{3,4-bis[(4-tert-butylbenzyl)oxy]phenyl}methylidene) amino]oxy}acetic acid or a pharmaceutically acceptable salt or ester form thereof; {[((1E)-{3,4-bis[(4-fluorobenzyl)oxy]phenyl}methylidene)amino]oxy}acetic acid or a pharmaceutically acceptable salt or ester form thereof; ({[(1E)-(3,4-bis{[4-(trifluoromethyl)benzyl]oxy}phenyl)methylidene] amino}oxy)acetic acid or a pharmaceutically acceptable salt or ester form thereof; {[((1E)-{3,4-bis[(4-bromobenzyl)oxy]

phenyl}methylidene)amino]oxy}acetic acid or a pharmaceutically acceptable salt or ester form thereof; {[((1E)-{3,4-bis[(3-chlorobenzyl)oxy]phenyl}methylidene)amino]oxy}acetic acid or a pharmaceutically acceptable salt or ester form thereof; {[((1E)-{3,4-bis[(3-bromobenzyl)oxy]phenyl}methylidene)amino]oxy}acetic acid or a pharmaceutically acceptable salt or ester form thereof; {[((1E)-{3,4-bis[(3-methylbenzyl)oxy]phenyl}methylidene)amino]oxy}acetic acid or a pharmaceutically acceptable salt or ester form thereof; ({[(1E)-(3,4-bis{[3-(trifluoromethyl)benzyl]oxy}phenyl)methylidene]amino}oxy)acetic acid or a pharmaceutically acceptable salt or ester form thereof; {[((1E)-{3,4-bis[(4-methylbenzyl)oxy]phenyl}methylidene)amino]oxy}acetic acid or a pharmaceutically acceptable salt or ester form thereof; {[((1E)-{3,4-bis[(3,4-difluorobenzyl)oxy]phenyl}methylidene)amino]oxy}acetic acid or a pharmaceutically acceptable salt or ester form thereof; {[((1E)-{2,4-bis[(4-methylbenzyl)oxy]phenyl}methylidene)amino]oxy}acetic acid or a pharmaceutically acceptable salt or ester form thereof; {[((1E)-{2,4-bis[(4-fluorobenzyl)oxy]phenyl}methylidene)amino]oxy}acetic acid or a pharmaceutically acceptable salt or ester form thereof; ({[(1E)-(2,4-bis{[4-(trifluoromethyl)benzyl]oxy}phenyl)methylidene]amino}oxy)acetic acid or a pharmaceutically acceptable salt or ester form thereof; {[((1E)-{2,4-bis[(4-bromobenzyl)oxy]phenyl}methylidene)amino]oxy}acetic acid or a pharmaceutically acceptable salt or ester form thereof; {[((1E)-{2,4-bis[(4-tert-butylbenzyl)oxy]phenyl}methylidene)amino]oxy}acetic acid or a pharmaceutically acceptable salt or ester form thereof; {[((1E)-{2,4-bis[(3-chlorobenzyl)oxy]phenyl}methylidene)amino]oxy}acetic acid or a pharmaceutically acceptable salt or ester form thereof; {[((1E)-{2,4-bis[(3-bromobenzyl)oxy]phenyl}methylidene)amino]oxy}acetic acid or a pharmaceutically acceptable salt or ester form thereof; {[((1E)-{2,4-bis[(3-methylbenzyl)oxy]phenyl}methylidene)amino]oxy}acetic acid or a pharmaceutically acceptable salt or ester form thereof; ({[(1E)-(2,4-bis{[3-(trifluoromethyl)benzyl]oxy}phenyl)methylidene]amino}oxy)acetic acid or a pharmaceutically acceptable salt or ester form thereof; {[((1E)-{2,4-bis[(3,4-difluorobenzyl)oxy]phenyl}methylidene)amino]oxy}acetic acid or a pharmaceutically acceptable salt or ester form thereof; {[((1E)-{2,3-bis[(4-bromobenzyl)oxy]phenyl}methylidene)amino]oxy}acetic acid or a pharmaceutically acceptable salt or ester form thereof; {[((1E)-{2,3-bis[(4-fluorobenzyl)oxy]phenyl}methylidene)amino]oxy}acetic acid or a pharmaceutically acceptable salt or ester form thereof; ({[(1E)-(2,3-bis{[4-(trifluoromethyl)benzyl]oxy}phenyl)methylidene]amino}oxy)acetic acid or a pharmaceutically acceptable salt or ester form thereof; {[((1E)-{2,3-bis[(4-tert-butylbenzyl)oxy]phenyl}methylidene)amino]oxy}acetic acid or a pharmaceutically acceptable salt or ester form thereof; {[((1E)-{2,3-bis[(3-chlorobenzyl)oxy]phenyl}methylidene)amino]oxy}acetic acid or a pharmaceutically acceptable salt or ester form thereof; {[((1E)-{2,3-bis[(3-bromobenzyl)oxy]phenyl}methylidene)amino]oxy}acetic acid or a pharmaceutically acceptable salt or ester form thereof; {[((1E)-{2,3-bis[(3-methylbenzyl)oxy]phenyl}methylidene)amino]oxy}acetic acid or a pharmaceutically acceptable salt or ester form thereof; ({[(1E)-(2,3-bis{[3-(trifluoromethyl)benzyl]oxy}phenyl)methylidene]amino}oxy)acetic acid or a pharmaceutically acceptable salt or ester form thereof; {[((1E)-{2,3-bis[(4-methylbenzyl)oxy]phenyl}methylidene)amino]oxy}acetic acid or a pharmaceutically acceptable salt or ester form thereof; {[((1E)-{2,3-bis[(3,4-difluorobenzyl)oxy]phenyl}methylidene)amino]oxy}acetic acid or a pharmaceutically acceptable salt or ester form thereof; {[((1E)-{3,5-bis[(3-chlorobenzyl)oxy]phenyl}methylidene)amino]oxy}acetic acid or a pharmaceutically acceptable salt or ester form thereof; {[((1E)-{3,5-bis[(4-fluorobenzyl)oxy]phenyl}methylidene)amino]oxy}acetic acid or a pharmaceutically acceptable salt or ester form thereof; ({[(1E)-(3,5-bis{[4-(trifluoromethyl)benzyl]oxy}phenyl)methylidene]amino}oxy)acetic acid or a pharmaceutically acceptable salt or ester form thereof; {[((1E)-{3,5-bis[(4-bromobenzyl)oxy]phenyl}methylidene)amino]oxy}acetic acid or a pharmaceutically acceptable salt or ester form thereof; {[((1E)-{3,5-bis[(4-tert-butylbenzyl)oxy]phenyl}methylidene)amino]oxy}acetic acid or a pharmaceutically acceptable salt or ester form thereof; {[((1E)-{3,5-bis[(3-bromobenzyl)oxy]phenyl}methylidene)amino]oxy}acetic acid or a pharmaceutically acceptable salt or ester form thereof; {[((1E)-{3,5-bis[(3-methylbenzyl)oxy]phenyl}methylidene)amino]oxy}acetic acid or a pharmaceutically acceptable salt or ester form thereof; ({[(1E)-(3,5-bis{[3-(trifluoromethyl)benzyl]oxy}phenyl)methylidene]amino}oxy)acetic acid or a pharmaceutically acceptable salt or ester form thereof; {[((1E)-{3,5-bis[(4-methylbenzyl)oxy]phenyl}methylidene)amino]oxy}acetic acid or a pharmaceutically acceptable salt or ester form thereof; {[((1E)-{3,5-bis[(3,4-difluorobenzyl)oxy]phenyl}methylidene)amino]oxy}acetic acid or a pharmaceutically acceptable salt or ester form thereof; ({[(1E)-(2,5-bis{[3-(trifluoromethyl)benzyl]oxy}phenyl)methylidene]amino}oxy)acetic acid or a pharmaceutically acceptable salt or ester form thereof; {[((1E)-{2,5-bis[(4-fluorobenzyl)oxy]phenyl}methylidene)amino]oxy}acetic acid or a pharmaceutically acceptable salt or ester form thereof; ({[(1E)-(2,5-bis{[4-(trifluoromethyl)benzyl]oxy}phenyl)methylidene]amino}oxy)acetic acid or a pharmaceutically acceptable salt or ester form thereof; {[((1E)-{2,5-bis[(4-bromobenzyl)oxy]phenyl}methylidene)amino]oxy}acetic acid or a pharmaceutically acceptable salt or ester form thereof; {[((1E)-{2,5-bis[(4-tert-butylbenzyl)oxy]phenyl}methylidene)amino]oxy}acetic acid or a pharmaceutically acceptable salt or ester form thereof; {[((1E)-{2,5-bis[(3-chlorobenzyl)oxy]phenyl}methylidene)amino]oxy}acetic acid or a pharmaceutically acceptable salt or ester form thereof; {[((1E)-{2,5-bis[(3-bromobenzyl)oxy]phenyl}methylidene)amino]oxy}acetic acid or a pharmaceutically acceptable salt or ester form thereof; {[((1E)-{2,5-bis[(3-methylbenzyl)oxy]phenyl}methylidene)amino]oxy}acetic acid or a pharmaceutically acceptable salt or ester form thereof; {[((1E)-{2,5-bis[(4-methylbenzyl)oxy]phenyl}methylidene)amino]oxy}acetic acid or a pharmaceutically acceptable salt or ester form thereof; {[((1E)-{2,5-bis[(3,4-difluorobenzyl)oxy]phenyl}methylidene)amino]oxy}acetic acid or a pharmaceutically acceptable salt or ester form thereof.

In alternative embodiments of the present invention, substituted acetic acid derivatives include substituted acetylenic oximeacetic acid derivatives of the following formula:

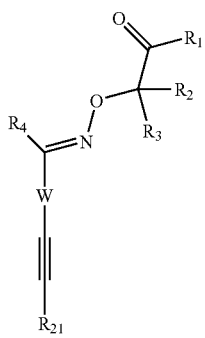

Formula 11 wherein $R_1$, $R_2$, $R_3$, $R_4$, W, $R_{21}$, m, and p are defined as above for Formula 1.

Compounds of the present invention also include prodrugs, stereoisomers, or pharmaceutically acceptable salts or ester forms of Formula 11.

In certain compounds of Formula 11, $R_1$ is —$OC_1$-$C_6$ alkyl or —OH. In certain preferred embodiments, $R_1$ is —OH. In such embodiments, $R_2$, $R_3$, $R_4$, W, $R_{21}$, m, and p are as defined herein for compounds of Formula 11.

In certain compounds of Formula 11, $R_2$ and $R_3$ are, independently, $CH_2$—$C_3$-$C_6$ cycloalkyl, —$CH_2$-pyridinyl, or benzyl wherein the rings of the cycloalkyl, pyridinyl, and benzyl groups are optionally substituted by 1 to 3 groups selected from halogen, $C_1$-$C_3$ alkyl, $C_1$-$C_3$ perfluoroalkyl, —O—$C_1$-$C_3$ perfluoroalkyl, $C_1$-$C_3$ alkoxy, —OH, —$NH_2$, —CN, or —$NO_2$. In other embodiments, $R_2$ and $R_3$ are, independently, alkyl or hydrogen. In certain preferred embodiments, $R_2$ and $R_3$ are hydrogen. In such embodiments, $R_1$, $R_4$, W, $R_{21}$, m, and p are as defined herein for compounds of Formula 11.

In certain compounds of Formula 11, $R_4$ is $C_3$-$C_6$ cycloalkyl, $CH_2$—$C_3$-$C_6$ cycloalkyl, pyridinyl, —$CH_2$-pyridinyl, phenyl or benzyl wherein the rings of the cycloalkyl, pyridinyl, phenyl, and benzyl groups are optionally substituted by 1 to 3 groups selected from halogen, $C_1$-$C_3$ alkyl, $C_1$-$C_3$ perfluoroalkyl, —O—$C_1$-$C_3$ perfluoroalkyl, $C_1$-$C_3$ alkoxy, —OH, —$NH_2$, or —$NO_2$. In other embodiments, $R_4$ is alkyl or hydrogen. In certain preferred embodiments, $R_4$ is hydrogen. In such embodiments, $R_1$, $R_2$, $R_3$, W, $R_{21}$, m, and p are as defined herein for compounds of Formula 11.

$R_{21}$ can be hydrogen, $C_1$-$C_8$ alkyl, $C_1$-$C_8$ alkenyl, $C_1$-$C_8$ alkynyl, —$(CH_2)_p$-aryl, —$(CH_2)_p$-heteroaryl, —$(CH_2)_p$—O-aryl, —$(CH_2)_p$—O-heteroaryl, —$(CH_2)_p$—O—$(CH_2)_m$-aryl, —$(CH_2)_p$—O—$(CH_2)_m$-heteroaryl, aryl, or heteroaryl. In certain embodiments of compounds of Formula 11, $R_{21}$ is —$(CH_2)_n$-aryl, —$(CH_2)_n$-heteroaryl, —$(CH_2)$, —O-aryl, —$(CH_2)$, —O-heteroaryl, —$(CH_2)$, —O—$(CH_2)_m$-aryl, —$(CH_2)_n$—O—$(CH_2)_m$-heteroaryl, aryl, or heteroaryl wherein the rings of the aryl and heteroaryl groups are optionally substituted by 1 to 3 groups selected from halogen, $C_1$-$C_3$ alkyl, $C_1$-$C_3$ perfluoroalkyl, —O—$C_1$-$C_3$ perfluoroalkyl, $C_1$-$C_3$ alkoxy, —OH, —$NH_2$, —CN or —$NO_2$. In certain embodiments, $R_{21}$ is aryl, alkyl, —$(CH_2)$—O-aryl where the aryl group is optionally substituted with one or more groups selected from halogen, perfluoroalkyl, alkyl, or branched alkyl. For example, in some embodiments, $R_{21}$ is —$(CH_2)$—O-phenyl where the phenyl group is optionally substituted with chlorine, bromine, butyl or branched butyl. In such embodiments, $R_1$, $R_2$, $R_3$, $R_4$, W, m, and p are as defined herein for compounds of Formula 11.

W can be aryl or heteroaryl. In certain preferred embodiments, W is phenyl. In such embodiments, $R_1$, $R_2$, $R_3$, $R_4$, $R_{21}$, m, and p are as defined herein for compounds of Formula 11.

In certain embodiments, such substituted acetylenic oximeacetic acid derivatives include the following compounds:

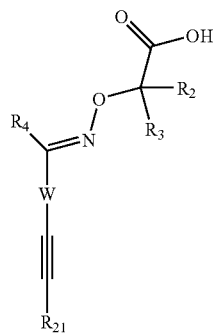

Formula 12

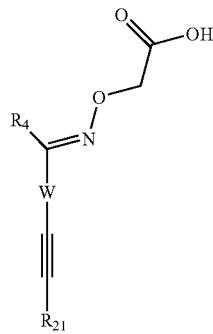

Formula 13 wherein $R_1$, $R_2$, $R_3$, $R_4$, W, $R_{21}$, m, and p are defined as above for Formula 1.

In certain embodiments of the present invention, $R_1$ is —OH, unsubstituted —$OC_1$-$C_8$ alkyl, or $NH_2$;

$R_2$ and $R_3$ are, independently, hydrogen, unsubstituted $C_1$-$C_8$ alkyl, —$CH_2$—$C_3$-$C_6$ cycloalkyl, —$CH_2$-pyridinyl, phenyl, or benzyl wherein the rings of the cycloalkyl, pyridinyl, phenyl or benzyl groups are optionally substituted by 1 to 3 groups selected from halogen, unsubstituted $C_1$-$C_3$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —OH, —CN, —$NH_2$, or —$NO_2$;

$R_4$ is hydrogen, unsubstituted $C_1$-$C_8$ alkyl, $C_3$-$C_6$ cycloalkyl, —$CH_2$—$C_3$-$C_6$ cycloalkyl, phenyl, benzyl, pyridinyl, or —$CH_2$-pyridinyl wherein the rings of the cycloalkyl, phenyl, benzyl, and pyridinyl groups are optionally substituted by 1 to 3 groups selected from halogen, unsubstituted $C_1$-$C_3$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —OH, —$NH_2$, or —$NO_2$;

$R_{21}$ is hydrogen, $C_1$-$C_8$ alkyl, $C_1$-$C_8$ alkenyl, $C_1$-$C_8$ alkynyl, —$(CH_2)_p$-aryl, —$(CH_2)_p$-heteroaryl, —$(CH_2)_p$—O-aryl, —$(CH_2)_p$—O-heteroaryl, —$(CH_2)_p$—O—$(CH_2)_m$-aryl, —$(CH_2)_p$—O—$(CH_2)_m$-heteroaryl, aryl, or heteroaryl wherein the rings of the aryl and heteroaryl groups are optionally substituted by 1 to 3 groups selected from halogen, unsubstituted $C_1$-$C_3$ alkyl, unsubstituted $C_1$-$C_3$ perfluoroalkyl, unsubstituted —O—$C_1$-$C_3$ perfluoroalkyl, unsubstituted $C_1$-$C_3$ alkoxy, —OH, —CN—$NH_2$, or —$NO_2$;

W is unsubstituted aryl or unsubstituted heteroaryl.

Exemplary substituted acetylenic oximeacetic acid derivatives of the present invention include, but are not limited to, {[((1E)-{4-[3-(4-tert-butylphenoxy)prop-1-ynyl]phenyl}methylidene)amino]oxy}acetic acid or a pharmaceutically acceptable salt or ester form thereof; {[((1E)-{4-[3-(4-bromophenoxy)prop-1-ynyl]phenyl}methylidene)amino]oxy}acetic acid or a pharmaceutically acceptable salt or ester form thereof; ({[(1E)-(4-{3-[3,5-bis(trifluoromethyl)phenoxy]prop-1-ynyl}phenyl)methylidene]amino}oxy)acetic acid or a pharmaceutically acceptable salt or ester form thereof; {[((1E)-{4-[3-(3,5-dichlorophenoxy)prop-1-ynyl]phenyl}methylidene)amino]oxy}acetic acid or a pharmaceutically acceptable salt or ester form thereof; {[((1E)-{4-[3-(3-chlorophenoxy)prop-1-ynyl]phenyl}methylidene)amino]oxy}acetic acid or a pharmaceutically acceptable salt or ester form thereof; {[((1E)-{4-[3-(4-isobutylphenoxy)prop-1-ynyl]phenyl}methylidene)amino]oxy}acetic acid or a pharmaceutically acceptable salt or ester form thereof; {[((1E)-{3-[3-(4-tert-butylphenoxy)prop-1-ynyl]phenyl}methylidene)amino]oxy}acetic acid or a pharmaceutically acceptable salt or ester form thereof; {[((1E)-{3-[3-(4-bromophenoxy)prop-1-ynyl]phenyl}methylidene)amino]oxy}acetic acid or a pharmaceutically acceptable salt or ester form thereof; ({[(1E)-(3-{3-[3,5-bis(trifluoromethyl)phenoxy]prop-1-ynyl}phenyl)methylidene]amino}oxy)acetic acid or a pharmaceutically acceptable salt or ester form thereof; {[((1E)-{3-[3-(3,5-dichlorophenoxy)prop-1-ynyl]phenyl}methylidene)amino]oxy}acetic acid or a pharmaceutically acceptable salt or ester form thereof; {[((1E)-{3-[3-(3-chlorophenoxy)prop-1-ynyl]phenyl}methylidene)amino]oxy}acetic acid or a pharmaceutically acceptable salt or ester form thereof; and {[((1E)-{3-[3-(4-isobutylphenoxy)prop-1-ynyl]phenyl}methylidene)amino]oxy}acetic acid.

The present invention also provides compositions comprising substituted acetic acid derivatives, including those compounds of formulas 1-13 or a stereoisomer or pharmaceutically acceptable salt thereof, and one or more pharmaceutically acceptable carriers, excipients, or diluents. Such compositions include pharmaceutical compositions for treating or controlling disease states or conditions associated with increased PAI-1 activity. In certain embodiments, the compositions comprise mixtures of one or more substituted acetic acid derivatives.

Certain of the compounds of formulas 1-13 contain stereogenic carbon atoms or other chiral elements and thus give rise to stereoisomers, including enantiomers and diastereomers. The present invention includes all of the stereoisomers of formulas 1-13, as well as mixtures of the stereoisomers. Throughout this application, the name of the product, where the absolute configuration of an asymmetric center is not indicated, is intended to embrace the individual stereoisomers as well as mixtures of stereoisomers. When it is necessary to distinguish the enantiomers from one another and from the racemate, the sign of the optical rotation [(+), (−) and (±)] is utilized. Furthermore, throughout this application, the designations R* and S* are used to indicate relative stereochemistry, employing the Chemical Abstracts convention which automatically assigns R* to the lowest numbered asymmetric center.

Where an enantiomer is preferred, it can, in some embodiments, be provided substantially free of the corresponding enantiomer. Thus, an enantiomer substantially free of the corresponding enantiomer refers to a compound that is isolated or separated via separation techniques or prepared free of the corresponding enantiomer. "Substantially free," as used herein, means that the compound is made up of a significantly greater proportion of one enantiomer. In preferred embodiments, the compound is made up of at least about 90% by weight of a preferred enantiomer. In other embodiments of the invention, the compound is made up of at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein. Methods for the preparation of preferred enantiomers are described, for example, in Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); and Wilen, S. H. Tables of Resolving Agents and Optical Resolutions p. 268 (E. L. Eliel, Ed., Univ. of Notre Dame Press, Notre Dame, Ind. 1972).

Exemplary salt forms of the compounds herein include, but are not limited to, sodium salts and potassium salts. Other exemplary salt forms of these compounds include, but are not limited to, those formed with pharmaceutically acceptable inorganic and organic bases known in the art. Salt forms prepared using inorganic bases include hydroxides, carbonates or bicarbonates of the therapeutically acceptable alkali metals or alkaline earth metals, such as sodium potassium, magnesium, calcium and the like. Acceptable organic bases include amines, such as benzylzmine, mono-, di- and trialkylamines, preferably those having alkyl groups of from 1 to 6 carbon atoms, more preferably 1 to 3 carbon atoms, such as methylamine, dimethylamine, trimethylamine, ethylamine, diethylamine, triethylamine, mono-, di-, and triethanolamine. Exemplary salts also include alkylene diamines containing up to 6 carbon atoms, such as hexamethylenediamine; cyclic saturated or unsaturated bases containing up to 6 carbon atoms, including pyrrolidine, piperidine, morpholine, piperazine and their N-alkyl and N-hydroxyalkyl derivatives, such as N-methyl-morpholine and N-(2-hydroxyethyl)-piperidine, or pyridine. Quaternary salts can also be formed, such as tetralkyl forms, such as tetramethyl forms, alkyl-alkanol forms, such as methyl-triethanol or trimethyl-monoethanol forms, and cyclic ammonium salt forms, such as N-methylpyridinium, N-methyl-N-(2-hydroxyethyl)-morpholinium, N,N-di-methylmorpholinium, N-methyl-N-(2-hydroxyethyl)-morpholinium, or N,N-dimethyl-piperidinium salt forms. These salt forms can be prepared using the acidic compound(s) of Formulas 1-13 and procedures known in the art.

Exemplary ester forms of the compounds of this invention include, but are not limited to, straight chain alkyl esters having from 1 to 6 carbon atoms or branched chain alkyl groups containing 3 or 6 carbon atoms, including methyl, ethyl, propyl, butyl, 2-methylpropyl and 1,1-dimethylethyl esters. Other exemplary esters include, but are not limited to, those of the formula —$COOR_{31}$ wherein $R_{31}$ is selected from the formula:

(A)

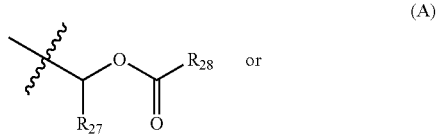

-continued

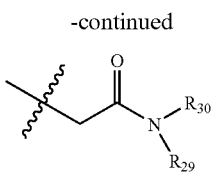

(B)

wherein $R_{27}$, $R_{28}$, $R_{29}$, $R_{30}$ are independently selected from hydrogen, alkyl of from 1 to 10 carbon atoms, aryl of 6 to 12 carbon atoms, arylalkyl of from 6 to 12 carbon atoms; heteroaryl or alkylheteroaryl wherein the heteroaryl ring is bound by an alkyl chain of from 1 to 6 carbon atoms. Ester forms of the compounds herein include but are not limited to $C_1$-$C_6$ alkyl esters, cycloalkyl, cycloalkyl esters, and alkylaryl esters.

Preferred compounds of the present invention inhibit PAI-1 activity. Accordingly, the compounds can be used for the treatment, including prevention, inhibition, and/or amelioration of PAI-1 related disorders in a subject, including, for example, in the treatment of noninsulin dependent diabetes mellitus, in the treatment of cardiovascular disease, and in the treatment of thrombotic events associated with coronary artery and cerebrovascular disease. Using the methods of the present invention, a skilled medical practitioner will know how to administer substituted acetic acid derivatives, including those represented by formulas 1-13, to a subject suffering from any of the diseases associated with increased PAI-1 activity or expression, e.g., diabetes or cardiovascular disease, in order to effect treatment for that disease.

In one exemplary embodiment, substituted acetic acid derivatives are administered to a subject in order to treat disease processes involving thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary thrombosis, cerebral thrombosis, thromboembolic complications of surgery (such as joint or hip replacement), and peripheral arterial occlusion.

Any disease or condition that is associated with increased PAI-1 activity or expression in a subject can be treated using substituted acetic acid derivatives. Exemplary diseases and conditions include stroke, e.g., stroke associated with or resulting from atrial fibrillation; diseases associated with extracellular matrix accumulation including, but not limited to, renal fibrosis, chronic obstructive pulmonary disease, polycystic ovary syndrome, restenosis, renovascular disease, and organ transplant rejection; diseases associated with neoangiogenesis, including, but not limited to, diabetic retinopathy; Alzheimer's disease, e.g., by increasing or normalizing levels of plasmin concentration in a subject; myelofibrosis with myeloid metaplasia, e.g., by regulating stromal cell hyperplasia and increases in extracellular matrix proteins; diabetic nephropathy and renal dialysis associated with nephropathy; malignancies or cancers, including, but not limited to, leukemia, breast cancer and ovarian cancer; tumors, including, but not limited to, liposarcomas and epithelial tumors; septicemia; obesity; insulin resistance; proliferative diseases, including, but not limited to, psoriasis; conditions associated with abnormal coagulation homeostasis; low grade vascular inflammation; cerebrovascular diseases; hypertension; dementia; osteoporosis; arthritis; respiratory diseases, such as asthma; heart failure; arrhythmia; angina, including, but not limited to, angina pectoris; atherosclerosis and sequelae; kidney failure; multiple sclerosis; osteoporosis; osteopenia; dementia; peripheral vascular disease; peripheral arterial disease; acute vascular syndromes; microvascular diseases including, but not limited to, nephropathy, neuropathy, retinopathy and nephrotic syndrome; hypertension; Type I and 2 diabetes and related diseases; hyperglycemia; hyperinsulinemia; malignant lesions; premalignant lesions; gastrointestinal malignancies; coronary heart disease, including, but not limited to, primary and secondary prevention of myocardial infarction, stable and unstable angina, primary prevention of coronary events, and secondary prevention of cardiovascular events; and inflammatory diseases, including, but not limited to, septic shock and the vascular damage associated with infections.

The compounds of the present invention can also be administered to a subject in combination with a second therapeutic agent, including, but not limited to, prothrombolytic, fibrinolytic, and anticoagulant agents, or in conjunction with other therapies, for example, protease inhibitor-containing highly active antiretroviral therapy (HAART) for the treatment of diseases which originate from fibrinolytic impairment and hyper-coagulability of HIV-1 infected patients. In certain embodiments, the compounds of the present invention can be administered in conjunction with and/or following processes or procedures involving maintaining blood vessel patency, including, but not limited to, vascular surgery, vascular graft and stent patency, organ, tissue and cell implantation and transplantation. The compounds of the present invention can also be used for the treatment of blood and blood products used in dialysis, blood storage in the fluid phase, especially ex vivo platelet aggregation. The compounds of the present invention can also be administered to a subject as a hormone replacement agent or to reduce inflammatory markers or C-reactive protein. The compounds can be administered to improve coagulation homeostasis, to improve endothelial function, or as a topical application for wound healing, e.g., the prevention of scarring. The compounds of the present invention can be administered to a subject in order to reduce the risk of undergoing a myocardial revascularization procedure. The present compounds can also be added to human plasma during the analysis of blood chemistry in hospital settings to determine the fibrinolytic capacity thereof. In certain embodiments, the compounds of the present invention can be used as imaging agents for the identification of metastatic cancers.

Synthesis of Substituted Acetic Acid Derivatives

Compounds of the present invention can be prepared by those skilled in the art of organic synthesis employing conventional methods that utilize readily available reagents and starting materials. Representative compounds of the present invention can be prepared using the following synthetic schemes. The skilled practitioner will know how to make use of variants of these process steps, which in themselves are well known in the art.

In certain embodiments of the present invention, representative substituted indolymethylideneaminooxy acetic acid derivatives can be prepared using scheme 1.

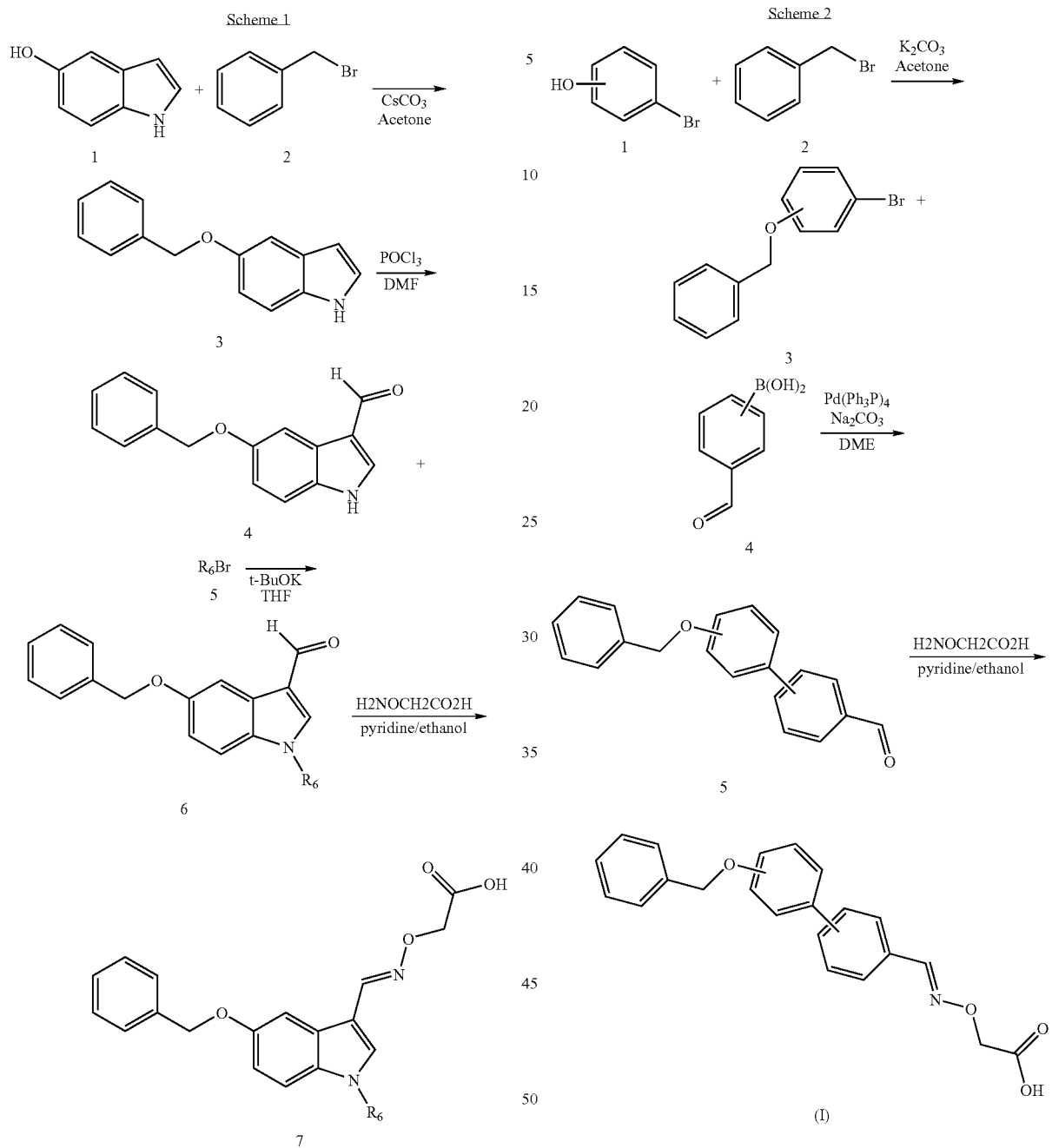

5-Hydroxyindole was reacted with benzyl bromide 2 in the presence of a base like cesium carbonate or potassium carbonate in a solvent like acetone to give benzyl ether 3. Benzyl ether 3 was formylated using phosphorus oxychloride and dimethylformamide to give aldehyde 4. Aldehyde 4 was reacted with bromide 5 in the presence of a base like potassium t-butoxide in a solvent like tetrahydrofuran to give compound 6. The aldehyde 6 was reacted with carboxymethoxylamine hemihydrochloride in a mixture of pyridine and ethanol to yield indole oxime acetic acid (I).

Representative substituted biphenylmethylidene aminooxy acetic acid derivatives can be prepared using scheme 2.

Bromophenol 1 was reacted with benzyl bromide 2 in the presence of a base like cesium carbonate or potassium carbonate in a solvent like acetone to give benzyl ether 3. Benzyl ether 3 was reacted with formylboronic acid 4 using tetrakis (triphenylphosphine) palladium(0) and sodium carbonate in a solvent like ethylene glycol dimethyl ether (DME) to give aldehyde 5. The aldehyde 5 was reacted with carboxymethoxylamine in a mixture of pyridine and ethanol to yield biphenyl oxime acetic acid (I).

Representative substituted bisbenzyloxyphenylmethylidene aminooxy acetic acid derivatives can be prepared using scheme 3.

Scheme 3

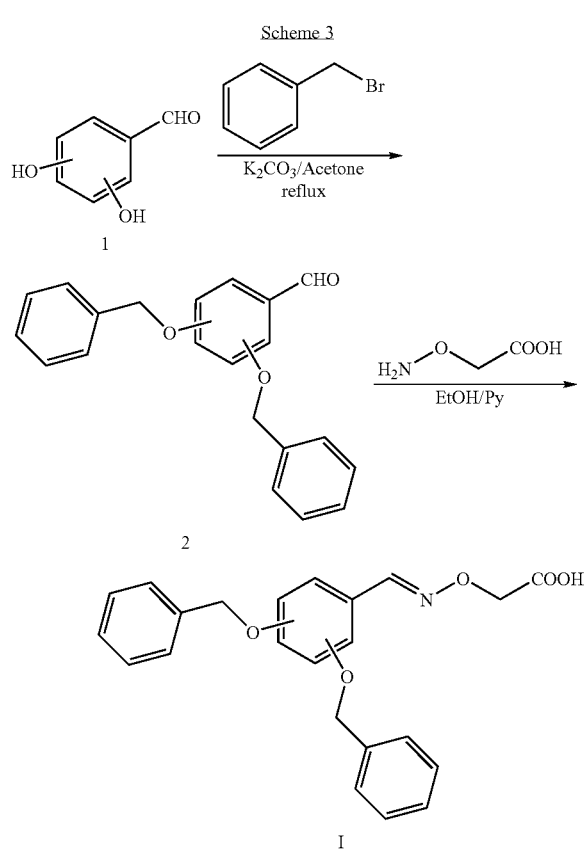

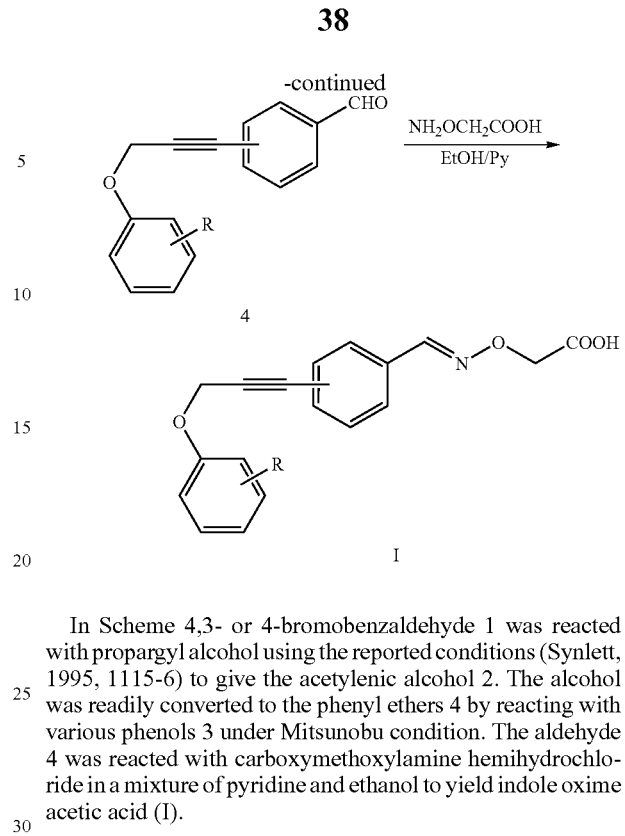

In Scheme 3, dihydroxybenzaldehyde 1 was reacted with benzyl bromide in the presence of a base like potassium carbonate in a solvent like acetone to give benzyl ether 2. Benzyl ether 2 was reacted with carboxymethoxylamine in a mixture of pyridine and ethanol to yield bisbenzloxyphenyl oxime acetic acid (I).

In certain embodiments of the present invention, representative substituted acetylenic oximeacetic acid derivatives can be prepared using scheme 4

Scheme 4

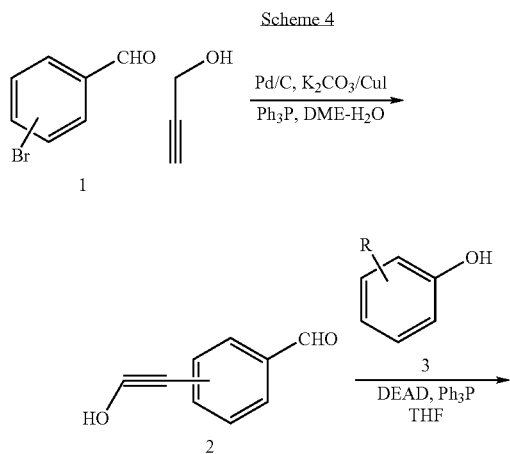

In Scheme 4, 3- or 4-bromobenzaldehyde 1 was reacted with propargyl alcohol using the reported conditions (Synlett, 1995, 1115-6) to give the acetylenic alcohol 2. The alcohol was readily converted to the phenyl ethers 4 by reacting with various phenols 3 under Mitsunobu condition. The aldehyde 4 was reacted with carboxymethoxylamine hemihydrochloride in a mixture of pyridine and ethanol to yield indole oxime acetic acid (I).

C. Substituted Acetic Acid Derivatives as Pharmaceutical Compositions

The present invention provides substituted acetic acid derivatives as pharmaceuticals. In a preferred embodiment, the acetic acid derivatives are formulated as pharmaceuticals to treat diseases associated with increased PAI-1 activity, e.g., by inhibiting PAI-1 activity in a subject.

In general, substituted acetic acid derivatives can be administered as pharmaceutical compositions by any method known in the art for administering therapeutic drugs including oral, buccal, topical, systemic (e.g., transdermal, intranasal, or by suppository), or parenteral (e.g., intramuscular, subcutaneous, or intravenous injection). Compositions can take the form of tablets, pills, capsules, semisolids, powders, sustained release formulations, solutions, suspensions, emulsions, syrups, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, can be found in such standard references as Alfonso AR: Remington's Pharmaceutical Sciences, 17th ed., Mack Publishing Company, Easton Pa., 1985. Suitable liquid carriers, especially for injectable solutions, include water, aqueous saline solution, aqueous dextrose solution, and glycols. In some embodiments of the present invention, substituted acetic acid derivatives suitable for use in the practice of this invention will be administered either singly or in combination with at least one other compound of this invention. Substituted acetic acid derivatives suitable for use in the practice of the present invention can also be administered with at least one other conventional therapeutic agent for the disease being treated.

Aqueous suspensions of the invention can contain a substituted acetic acid derivative in admixture with excipients suitable for the manufacture of aqueous suspensions. Such excipients can include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions can be formulated by suspending a substituted acetic acid derivative in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, well known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of substituted acetic acid derivative in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol. The formulations of commends can be presented in unit-dose or multi-dose sealed containers, such as ampules and vials.

Injection solutions and suspensions can be prepared from sterile powders, granules, and tablets of the kind previously described.

Substituted acetic acid derivatives suitable for use in the practice of this invention can be administered orally. The amount of a compound of the present invention in the composition can vary widely depending on the type of composition, size of a unit dosage, kind of excipients, and other factors well known to those of ordinary skill in the art. In general, the final composition can comprise, for example, from 0.000001 percent by weight (% w) to 10% w of the substituted acetic acid derivative, preferably 0.00001% w to 1% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient. Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropylmethyl-cellulose or sodium carboxymethylcellulose; and gums including arabic and tragacanth; as well as proteins such as gelatin and collagen. If desired, disintegrating or solubilizing agents can be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The substituted acetic acid derivatives of the present invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995).

The substituted acetic acid derivatives of the present invention can be delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present invention and the term "composition" can include the active ingredient in combination with an encapsulating material as a formulation, with or without other carriers. For example, the compounds of the present invention can also be delivered as microspheres for slow release in the body. In one embodiment, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao, Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months. Cachets can also be used in the delivery of the compounds of the present invention, e.g., anti-atherosclerotic medicaments.

In another embodiment, the compounds of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compound into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

In other cases, the preferred preparation can be a lyophilized powder which may contain, for example, any or all of the following: 1 mM-50 mM histidine, 0.1%-2% sucrose, 2%-7% mannitol, at a pH range of 4.5 to 5.5, that is combined with buffer prior to use.

A pharmaceutical composition of the invention can optionally contain, in addition to a substituted acetic acid derivative, at least one other therapeutic agent useful in the treatment of a disease or condition associated with increased PAI-1 activity.

The pharmaceutical compositions are generally formulated as sterile, substantially isotonic and in full compliance with all Good Manufacturing Practice (GMP) regulations of the U.S. Food and Drug Administration

D. Determining Dosage Regimens for Substituted Acetic Acid Derivatives

The present invention provides methods of inhibiting PAI-1 activity in a subject for the treatment of diseases and conditions associated with increased PAI-1 activity using substituted acetic acid derivatives. In an exemplary embodiment of the present invention, a skilled practitioner will treat a subject having a disease associated with elevated PAI-1 levels and/or activity with the compounds of the present invention.

For treatment purposes, the compositions or compounds disclosed herein can be administered to the subject in a single bolus delivery, via continuous delivery (e.g., continuous transdermal, mucosal, or intravenous delivery) over an extended time period, or in a repeated administration protocol (e.g., by an hourly, daily or weekly, repeated administration protocol). The pharmaceutical formulations of the present invention can be administered, for example, one or more times daily, 3 times per week, or weekly. In an exemplary embodiment of the present invention, the pharmaceutical formulations of the present invention are orally administered once or twice daily.

In this context, a therapeutically effective dosage of the biologically active agent(s) can include repeated doses within a prolonged treatment regimen that will yield clinically significant results to alleviate one or more symptoms or detectable conditions associated with increased PAI-1 activity. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response). In alternative embodiments, an "effective amount" or "therapeutically effective dose" of the biologically active agent(s) will simply inhibit or enhance one or more selected biological activity(ies) correlated with a disease or condition, as set forth above, for either therapeutic or diagnostic purposes.

The actual dosage of biologically active agents will of course vary according to factors such as the extent of exposure and particular status of the subject (e.g., the subject's age, size, fitness, extent of symptoms, susceptibility factors, etc), time and route of administration, as well as other drugs or treatments being administered concurrently. Dosage regimens can be adjusted to provide an optimum prophylactic or therapeutic response. By "therapeutically effective dose" herein is meant a dose that produces effects for which it is administered. More specifically, a therapeutically effective dose of the compound(s) of the invention preferably alleviates symptoms, complications, or biochemical indicia of diseases associated with increased PAI-1 activity. The exact dose will depend on the purpose of the treatment, and will be ascertainable by one skilled in the art using known techniques (see, e.g., Lieberman, Pharmaceutical Dosage Forms (Vols. 1-3, 1992); Lloyd, 1999, The Art, Science, and Technology of Pharmaceutical Compounding; and Pickar, 1999, Dosage Calculations). A therapeutically effective dose is also one in which any toxic or detrimental side effects of the active agent is outweighed in clinical terms by therapeutically beneficial effects. It is to be further noted that for each particular subject, specific dosage regimens should be evaluated and adjusted over time according to the individual need and professional judgment of the person administering or supervising the administration of the compounds.

In an exemplary embodiment of the present invention, unit dosage forms of the compounds are prepared for standard administration regimens. In this way, the composition can be subdivided readily into smaller doses at the physicians direction. For example, unit dosages can be made up in packeted powders, vials or ampoules and preferably in capsule or tablet form. The active compound present in these unit dosage forms of the composition can be present in an amount of from about one gram to about fifteen grams or more, for single or multiple daily administration, according to the particular need of the patient. By initiating the treatment regimen with a minimal daily dose of, for example, about one gram, the blood levels of PAI-1 and the patients symptomatic relief analysis can be used to determine whether a larger or smaller dose is indicated. Effective administration of the compounds of this invention can be given at an oral dose of, for example, from about 0.1 mg/kg/day to about 1,000 mg/kg/day. Preferably, administration will be from about 10/mg/kg/day to about 600 mg/kg/day, more preferably from about 25 to about 200 mg/kg/day, and even more preferably from about 50 mg/kg/day to about 100 mg/kg/day.

In certain embodiments, the present invention is directed to prodrugs of compounds of formulas 1-13. The term "prodrug," as used herein, means a compound that is convertible in vivo by metabolic means (e.g. by hydrolysis) to a compound of formula 1-15. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991), Bundgaard, et al., *Journal of Drug Delivery Reviews,* 8:1-38 (1992), Bundgaard, *J. of Pharmaceutical Sciences,* 77:285 et seq. (1988); and Higuchi and Stella (eds.) Prodrugs as Novel Drug Delivery Systems, American Chemical Society (1975).

E. Kits

After a pharmaceutical comprising a substituted acetic acid derivative has been formulated in a suitable carrier, it can be placed in an appropriate container and labeled for treatment of a PAI-1 related disorder, e.g., leukemia. Additionally, another pharmaceutical comprising at least one other therapeutic agent useful in the treatment of the PAI-1 related disorder can be placed in the container as well and labeled for treatment of the indicated disease. Alternatively, a single pharmaceutical comprising a substituted acetic acid derivative and at least one other therapeutic agent useful in the treatment of a PAI-1 related disorder can be placed in an appropriate container and labeled for treatment. For administration of pharmaceuticals comprising substituted acetic acid derivatives and of pharmaceuticals comprising, in a single pharmaceutical, substituted acetic acid derivatives and at least one other therapeutic agent useful in the treatment of a PAI-related disorder, such labeling would include, for example, instructions concerning the amount, frequency and method of administration. Similarly, for administration of multiple pharmaceuticals provided in the container, such labeling would include, for example, instructions concerning the amount, frequency and method of administration of each pharmaceutical.

EXAMPLES

The syntheses of compounds 1-173 are described in examples 1-173 respectively.

Example 1

Synthesis of ({[(1E)-(1-allyl-5-{[4-(trifluoromethyl)benzyl]oxy}-1H-indol-3-yl)methylidene]amino}oxy) acetic acid Step 1. To a solution of 5-hydroxyindole (66.3 mg, 0.5 mmol) in acetone was added cesium carbonate (651.6 mg, 2 mmol) and 4-(trifluoromethyl)benzyl bromide (0.120 ml, 0.5 mmol). The reaction mixture was shaken at 60° C. overnight. The mixture was filtered and washed. The solvent was evaporated in vacuo.

Step 2. To a solution of crude benzyl ether (0.5 mmol) obtained from step one in DMF (0.2 ml) at 6° C. was added a $POCl_3$/DMF solution (0.2 ml) in a 1.1:4 molar ratio. The reaction mixture was allowed to warm to 12° C. for 1 hour. Another 0.1 ml of $POCl_3$/DMF solution was added and the reaction mixture was shaken for one more hour. The mixture was carefully quenched with water and the solid filtered. The solid was dissolved in 1:1 MeOH/THF (5 ml). To this solution was added 0.2 ml concentrated HCl and the reaction was shaken at room temperature for 1 hour. The mixture was neutralized with 4N NaOH and the solvents were removed under reduced pressure. The crude residue was partitioned between EtOAc and water. The organic layer was dried with $MgSO_4$ and concentrated in vacuo.

Step 3. To a solution of aldehyde (0.5 mmol) obtained from step 2 in THF (0.5 ml) was added 1M solution of t-BuOK in THF (0.75 ml, 0.75 mmol) and allyl bromide (0.065 ml, 0.75 mmol). The reaction was shaken at room temperature overnight. The solvent was evaporated in vacuo.

Step 4. To a solution of aldehyde (0.5 mmol) dissolved in pyridine (0.5 ml) and EtOH (4.5 ml) was added carboxymethoxylamine hemihydrochloride (54.6 mg, 0.25 mmol). The reaction was heated to 60° C. for 2 hours. The solvent was evaporated in vacuo. The crude product was purified by RP-HPLC to give example 224. $^1$H NMR (DMSO $d_6$, 300 MHz) δ 4.61 (s, 2H), 4.81 (d, J=5.4 Hz, 2H), 5.02-5.18 (m, 2H), 5.22-5.27 (m, 3H), 5.94-6.03 (m, 1H), 6.97 (dd, J=8.9, 2.4 Hz, 1H), 7.40 (d, J=8.7 Hz, 1H), 7.69-7.79 (m, 5H), 8.38 (s, 1H), 12.72 (s, 1H); MS: (M+H) 433.0

Example 2

Synthesis of ({[(1E)-(1-ethyl-5-{[4-(trifluoromethyl)benzyl]oxy}-1H-indol-3-yl)methylidene]amino}oxy)acetic acid ({[(1E)-(1-ethyl-5-{[4-(trifluoromethyl)benzyl]oxy}-1H-indol-3-yl)methylidene]amino}oxy)acetic acid was synthesized using the procedure outlined for example 1 using 4-(trifluoromethyl)benzyl bromide and the resulting ether was further alkylated using ethyl bromide.

Example 3

Synthesis of ({[(1E)-(1-benzyl-5-{[4-(trifluoromethyl)benzyl]oxy}-1H-indol-3-yl)methylidene]amino}oxy)acetic acid ({[(1E)-(1-benzyl-5-{[4-(trifluoromethyl)benzyl]oxy}-1H-indol-3-yl)methylidene]amino}oxy)acetic acid was synthesized using the procedure outlined for example 1 using 4-(trifluoromethyl)benzyl bromide and the resulting ether was further alkylated using benzyl bromide.

Example 4

Synthesis of {[((1E)-{1-allyl-5-[(4-tert-butylbenzyl)oxy]-1H-indol-3-yl}methylidene)amino]oxy}acetic acid {[((1E)-{1-allyl-5-[(4-tert-butylbenzyl)oxy]-1H-indol-3-yl}methylidene)amino]oxy}acetic acid was synthesized using the procedure outlined for example 1 using 4-t-butylbenzyl bromide and the resulting ether was further alkylated using allyl bromide.

Example 5

Synthesis of {[((1E)-{5-[(4-tert-butylbenzyl)oxy]-1-ethyl-1H-indol-3-yl}methylidene)amino]oxy}acetic acid {[((1E)-{5-[(4-tert-butylbenzyl)oxy]-1-ethyl-1H-indol-3-yl}methylidene)amino]oxy}acetic acid were synthesized using the procedure outlined for example 1 using 4-t-butylbenzyl bromide and the resulting ether was further alkylated using ethyl bromide.

Example 6

Synthesis of {[((1E)-{1-benzyl-5-[(4-tert-butylbenzyl)oxy]-1H-indol-3-yl}methylidene)amino]oxy}acetic acid {[((1E)-{1-benzyl-5-[(4-tert-butylbenzyl)oxy]-1H-indol-3-yl}methylidene)amino]oxy}acetic acid was synthesized using the procedure outlined for example 1 using 4-t-butylbenzyl bromide and the resulting ether was further alkylated using benzyl bromide.

Example 7

Synthesis of {[((1E)-{1-allyl-5-[(4-bromobenzyl)oxy]-1H-indol-3-yl}methylidene)amino]oxy}acetic acid {[((1E)-{1-allyl-5-[(4-bromobenzyl)oxy]-1H-indol-3-yl}methylidene)amino]oxy}acetic acid was synthesized using the procedure outlined for example 1 using 4-bromobenzyl bromide and the resulting ether was further alkylated using allyl bromide.

Example 8

Synthesis of {[((1E)-{5-[(4-bromobenzyl)oxy]-1-ethyl-1H-indol-3-yl}methylidene)amino]oxy}acetic acid {[((1E)-{5-[(4-bromobenzyl)oxy]-1-ethyl-1H-indol-3-yl}methylidene)amino]oxy}acetic acid was synthesized using the procedure outlined for example 1 using 4-bromobenzyl bromide and the resulting ether was further alkylated using ethyl bromide.

Example 9

Synthesis of {[((1E)-{1-benzyl-5-[(4-bromobenzyl)oxy]-1H-indol-3-yl}methylidene)amino]oxy}acetic acid {[((1E)-{1-benzyl-5-[(4-bromobenzyl)oxy]-1H-indol-3-yl}methylidene)amino]oxy}acetic acid was synthesized using the procedure outlined for example 1 using 4-bromobenzyl bromide and the resulting ether was further alkylated using benzyl bromide.

Example 10

Synthesis of ({[(1E)-(1-allyl-5-{[3,5-bis(trifluoromethyl)benzyl]oxy}-1H-indol-3-yl)methylidene]amino}oxy)acetic acid ({[(1E)-(1-allyl-5-{[3,5-bis(trifluoromethyl)benzyl]oxy}-1H-indol-3-yl)methylidene]amino}oxy)acetic acid was synthesized using the procedure outlined for example 1 using 3,5-bis(trifluoromethyl)benzyl bromide and the resulting ether was further alkylated using allyl bromide.

Example 11

Synthesis of ({[(1E)-(5-{[3,5-bis(trifluoromethyl)benzyl]oxy}-1-ethyl-1H-indol-3-yl)methylidene]amino}oxy)acetic acid ({[(1E)-(5-{[3,5-bis(trifluoromethyl)benzyl]oxy}-1-ethyl-1H-indol-3-yl)methylidene]amino}oxy)acetic acid was synthesized using the procedure outlined for example 1 using 3,5-bis(trifluoromethyl)benzyl bromide and the resulting ether was further alkylated using ethyl bromide.

Example 12

Synthesis of ({[(1E)-(1-benzyl-5-{[3,5-bis(trifluoromethyl)benzyl]oxy}-1H-indol-3-yl)methylidene]amino}oxy)acetic acid ({[(1E)-(1-benzyl-5-{[3,5-bis(trifluoromethyl)benzyl]oxy}-1H-indol-3-yl)methylidene]amino}oxy)acetic acid was synthesized using the procedure outlined for example 1 using 3,5-bis(trifluoromethyl)benzyl bromide and the resulting ether was further alkylated using benzyl bromide.

Example 13

Synthesis of {[((1E)-{1-allyl-5-[(3-bromobenzyl)oxy]-1H-indol-3-yl}methylidene)amino]oxy}acetic acid {[((1E)-{1-allyl-5-[(3-bromobenzyl)oxy]-1H-indol-3-yl}methylidene)amino]oxy}acetic acid was synthesized using the procedure outlined for example 1 using 3-bromobenzyl bromide and the resulting ether was further alkylated using allyl bromide.

Example 14

Synthesis of {[((1E)-{5-[(3-bromobenzyl)oxy]-1-ethyl-1H-indol-3-yl}methylidene)amino]oxy}acetic acid {[((1E)-{5-[(3-bromobenzyl)oxy]-1-ethyl-1H-indol-3-yl}methylidene)amino]oxy}acetic acid was synthesized using the procedure outlined for example 1 using 3-bromobenzyl bromide and the resulting ether was further alkylated using ethyl bromide.

Example 15

Synthesis of {[((1E)-{1-benzyl-5-[(3-bromobenzyl)oxy]-1H-indol-3-yl}methylidene)amino]oxy}acetic acid {[((1E)-{1-benzyl-5-[(3-bromobenzyl)oxy]-1H-indol-3-yl}methylidene)amino]oxy}acetic acid was synthesized using the procedure outlined for example 1 using 3-bromobenzyl bromide and the resulting ether was further alkylated using benzyl bromide.

Example 16

Synthesis of {[((1E)-{1-allyl-5-[(3-chlorobenzyl)oxy]-1H-indol-3-yl}methylidene)amino]oxy}acetic acid {[((1E)-{1-allyl-5-[(3-chlorobenzyl)oxy]-1H-indol-3-yl}methylidene)amino]oxy}acetic acid were synthesized using the procedure outlined for example 1 using 3-chlorobenzyl bromide and the resulting ether was further alkylated using allyl bromide.

Example 17

Synthesis of {[((1E)-{5-[(3-chlorobenzyl)oxy]-1-ethyl-1H-indol-3-yl}methylidene)amino]oxy}acetic acid {[((1E)-{5-[(3-chlorobenzyl)oxy]-1-ethyl-1H-indol-3-yl}methylidene)amino]oxy}acetic acid were synthesized using the procedure outlined for example 1 using 3-chlorobenzyl bromide and the resulting ether was further alkylated ethyl bromide.

Example 18

Synthesis of {[((1E)-{1-benzyl-5-[(3-chlorobenzyl)oxy]-1H-indol-3-yl}methylidene)amino]oxy}acetic acid {[((1E)-{1-benzyl-5-[(3-chlorobenzyl)oxy]-1H-indol-3-yl}methylidene)amino]oxy}acetic acid were synthesized using the procedure outlined for example 1 using 3-chlorobenzyl bromide and the resulting ether was further alkylated using benzyl bromide.

Example 19

Synthesis of {[((1E)-{1-allyl-5-[(4-methylbenzyl)oxy]-1H-indol-3-yl}methylidene)amino]oxy}acetic acid {[((1E)-{1-allyl-5-[(4-methylbenzyl)oxy]-1H-indol-3-yl}methylidene)amino]oxy}acetic acid was synthesized using the procedure outlined for example 1 using 4-methylbenzyl bromide and the resulting ether was further alkylated using allyl bromide.

Example 20

Synthesis of {[((1E)-{1-ethyl-5-[(4-methylbenzyl)oxy]-1H-indol-3-yl}methylidene)amino]oxy}acetic acid {[((1E)-{1-ethyl-5-[(4-methylbenzyl)oxy]-1H-indol-3-yl}methylidene)amino]oxy}acetic acid was synthesized using the procedure outlined for example 1 using 4-methylbenzyl bromide and the resulting ether was further alkylated using ethyl bromide.

Example 21

Synthesis of {[((1E)-{1-benzyl-5-[(4-methylbenzyl)oxy]-1H-indol-3-yl}methylidene)amino]oxy}acetic acid {[((1E)-{1-benzyl-5-[(4-methylbenzyl)oxy]-1H-indol-3-yl}methylidene)amino]oxy}acetic acid was synthesized using the procedure outlined for example 1 using 4-methylbenzyl bromide and the resulting ether was further alkylated using benzyl bromide.

Example 22

Synthesis of ({[(1E)-(1-allyl-5-{[3-(trifluoromethyl) benzyl]oxy}-1H-indol-3-yl)methylidene]amino}oxy) acetic acid ({[(1E)-(1-allyl-5-{[3-(trifluoromethyl)benzyl]oxy}-1H-indol-3-yl)methylidene]amino}oxy)acetic acid was synthesized using the procedure outlined for example 1 using 3-(trifluoromethyl)benzyl bromide and the resulting ether was further alkylated using allyl bromide.

Example 23

Synthesis of ({[(1E)-(1-ethyl-5-{[3-(trifluoromethyl) benzyl]oxy}-1H-indol-3-yl)methylidene]amino}oxy) acetic acid ({[(1E)-(1-ethyl-5-{[3-(trifluoromethyl)benzyl]oxy}-1H-indol-3-yl)methylidene]amino}oxy)acetic acid was synthesized using the procedure outlined for example 1 using 3-(trifluoromethyl)benzyl bromide and the resulting ether was further alkylated using ethyl bromide.

Example 24

Synthesis of ({[(1E)-(1-benzyl-5-{[3-(trifluoromethyl)benzyl]oxy}-1H-indol-3-yl)methylidene] amino}oxy)acetic acid ({[(1E)-(1-benzyl-5-{[3-(trifluoromethyl)benzyl]oxy}-1H-indol-3-yl)methylidene]amino}oxy)acetic acid was synthesized using the procedure outlined for example 1 using 3-(trifluoromethyl)benzyl bromide and the resulting ether was further alkylated using benzyl bromide.

Example 25

Synthesis of {[((1E)-{1-allyl-5-[(3-methylbenzyl) oxy]-1H-indol-3-yl}methylidene)amino]oxy}acetic acid {[((1E)-{1-allyl-5-[(3-methylbenzyl)oxy]-1H-indol-3-yl}methylidene)amino]oxy}acetic acid was synthesized using the procedure outlined for example 1 using 3-methylbenzyl bromide and the resulting ether was further alkylated using allyl.

Example 26

Synthesis of {[((1E)-{1-ethyl-5-[(3-methylbenzyl) oxy]-1H-indol-3-yl}methylidene)amino]oxy}acetic acid {[((1E)-{1-ethyl-5-[(3-methylbenzyl)oxy]-1H-indol-3-yl}methylidene)amino]oxy}acetic acid was synthesized using the procedure outlined for example 1 using 3-methylbenzyl bromide and the resulting ether was further alkylated using ethyl bromide.

Example 27

Synthesis of {[((1E)-{1-benzyl-5-[(3-methylbenzyl) oxy]-1H-indol-3-yl}methylidene)amino]oxy}acetic acid {[((1E)-{1-benzyl-5-[(3-methylbenzyl)oxy]-1H-indol-3-yl}methylidene)amino]oxy}acetic acid was synthesized using the procedure outlined for example 1 using 3-methylbenzyl bromide and the resulting ether was further alkylated using benzyl bromide.

Example 28

Synthesis of {[((1E)-{5-[(2-chlorobenzyl)oxy]-1-ethyl-1H-indol-3-yl}methylidene)amino]oxy}acetic acid {[((1E)-{5-[(2-chlorobenzyl)oxy]-1-ethyl-1H-indol-3-yl}methylidene)amino]oxy}acetic acid was synthesized using the procedure outlined for example 1 using 2-chlorobenzyl bromide and the resulting ether was further alkylated using ethyl bromide.

Example 29

Synthesis of {[((1E)-{1-benzyl-5-[(2-chlorobenzyl) oxy]-1H-indol-3-yl}methylidene)amino]oxy}acetic acid {[((1E)-{1-benzyl-5-[(2-chlorobenzyl)oxy]-1H-indol-3-yl}methylidene)amino]oxy}acetic acid was synthesized using the procedure outlined for example 1 using 2-chlorobenzyl bromide and the resulting ether was further alkylated using benzyl bromide.

Example 30

Synthesis of {[((1E)-{5-[(2-chlorobenzyl)oxy]-1H-indol-3-yl}methylidene)amino]oxy}acetic acid {[((1E)-{5-[(2-chlorobenzyl)oxy]-1H-indol-3-yl}methylidene)amino]oxy}acetic acid was synthesized using the procedure outlined for example 1 using 2-chlorobenzyl bromide

Example 31

Synthesis of ({[(1E)-(1-(2-propynyl)-5-{[4-(trifluoromethyl)benzyl]oxy}-1H-indol-3-yl)methylidene] amino}oxy)acetic acid ({[(1E)-(1-(2-propynyl)-5-{[4-(trifluoromethyl)benzyl]oxy}-1H-indol-3-yl)methylidene]amino}oxy)acetic acid was synthesized using the procedure outlined for example 1 using 4-(trifluoromethyl)benzyl bromide and the resulting ether was further alkylated using propargyl bromide.

Example 32

Synthesis of ({[(1E)-(1-methyl-5-{[4-(trifluoromethyl)benzyl]oxy}-1H-indol-3-yl)methylidene] amino}oxy)acetic acid ({[(1E)-(1-methyl-5-{[4-(trifluoromethyl)benzyl]oxy}-1H-indol-3-yl)methylidene]amino}oxy)acetic acid was synthesized using the procedure outlined for example 1 using 4-(trifluoromethyl)benzyl bromide and the resulting ether was further alkylated using methyl iodide.

Example 33

Synthesis of [({(1E)-5-[(4-tert-butylbenzyl)oxy]-1-(2-propynyl)-1H-indol-3-yl]methylidene}amino)oxy]acetic acid

[({(1E)-5-[(4-tert-butylbenzyl)oxy]-1-(2-propynyl)-1H-indol-3-yl]methylidene}amino)oxy]acetic acid was synthesized using the procedure outlined for example 1 using 4-t-butylbenzyl bromide and the resulting ether was further alkylated using propargyl bromide.

Example 34

Synthesis of {[((1E)-{5-[(4-tert-butylbenzyl)oxy]-1-methyl-1H-indol-3-yl}methylidene)amino]oxy}acetic acid {[((1E)-{5-[(4-tert-butylbenzyl)oxy]-1-methyl-1H-indol-3-yl}methylidene)amino]oxy}acetic acid was synthesized using the procedure outlined for example 1 using 4-t-butylbenzyl bromide and the resulting ether was further alkylated using methyl iodide.

Example 35

Synthesis of [({(1E)-5-{[3,5-bis(trifluoromethyl)benzyl]oxy}-1-(2-propynyl)-1H-indol-3-yl]methylidene}amino)oxy]acetic acid

[({(1E)-5-{[3,5-bis(trifluoromethyl)benzyl]oxy}-1-(2-propynyl)-1H-indol-3-yl]methylidene}amino)oxy]acetic acid was synthesized using the procedure outlined for example 1 using 3,5-bis(trifluoromethyl)benzyl bromide and the resulting ether was further alkylated using propargyl bromide.

Example 36

Synthesis of [({(1E)-5-[(3-bromobenzyl)oxy]-1-(2-propynyl)-1H-indol-3-yl]methylidene}amino)oxy]acetic acid

[({(1E)-5-[(3-bromobenzyl)oxy]-1-(2-propynyl)-1H-indol-3-yl]methylidene}amino)oxy]acetic acid was synthesized using the procedure outlined for example 1 using 3-bromobenzyl bromide and the resulting ether was further alkylated using propargyl bromide.

Example 37

Synthesis of {[((1E)-{5-[(3-bromobenzyl)oxy]-1-methyl-1H-indol-3-yl}methylidene)amino]oxy}acetic acid {[((1E)-{5-[(3-bromobenzyl)oxy]-1-methyl-1H-indol-3-yl}methylidene)amino]oxy}acetic acid was synthesized using the procedure outlined for example 1 using 3-bromobenzyl bromide and the resulting ether was further alkylated using methyl iodide.

Example 38

Synthesis of [({(1E)-5-[(3-chlorobenzyl)oxy]-1-(2-propynyl)-1H-indol-3-yl]methylidene}amino)oxy]acetic acid

[({(1E)-5-[(3-chlorobenzyl)oxy]-1-(2-propynyl)-1H-indol-3-yl]methylidene}amino)oxy]acetic acid was synthesized using the procedure outlined for example 1 using 3-chlorobenzyl bromide and the resulting ether was further alkylated using propargyl bromide.

Example 39

Synthesis of {[((1E)-{5-[(3-chlorobenzyl)oxy]-1-methyl-1H-indol-3-yl}methylidene)amino]oxy}acetic acid {[((1E)-{5-[(3-chlorobenzyl)oxy]-1-methyl-1H-indol-3-yl}methylidene)amino]oxy}acetic acid was synthesized using the procedure outlined for example 1 using 3-chlorobenzyl bromide and the resulting ether was further alkylated using methyl iodide.

Example 40

Synthesis of [({(1E)-[1-allyl-5-(benzyloxy)-1H-indol-3-yl]methylidene}amino)oxy]acetic acid

[({(1E)-[1-allyl-5-(benzyloxy)-1H-indol-3-yl]methylidene}amino)oxy]acetic acid was synthesized using the procedure outlined for example 1 using benzyl bromide and the resulting ether was further alkylated using allyl bromide.

Example 41

Synthesis of [({(1E)-[1-benzyl-5-(benzyloxy)-1H-indol-3-yl]methylidene}amino)oxy]acetic acid

[({(1E)-[1-benzyl-5-(benzyloxy)-1H-indol-3-yl]methylidene}amino)oxy]acetic acid was synthesized using the procedure outlined for example 1 using benzyl bromide and the resulting ether was further alkylated using benzyl bromide.

Example 42

Synthesis of ({[(1E)-(1-(2-propynyl)-5-{[3-(trifluoromethyl)benzyl]oxy}-1H-indol-3-yl)methylidene]amino}oxy)acetic acid ({[(1E)-(1-(2-propynyl)-5-{[3-(trifluoromethyl)benzyl]oxy}-1H-indol-3-yl)methylidene]amino}oxy)acetic acid was synthesized using the procedure outlined for example 1 using 3-(trifluoromethyl)benzyl bromide and the resulting ether was further alkylated using propargyl bromide.

Example 43

Synthesis of ({[(1E)-(1-methyl-5-{[3-(trifluoromethyl)benzyl]oxy}-1H-indol-3-yl)methylidene]amino}oxy)acetic acid ({[(1E)-(1-methyl-5-{[3-(trifluoromethyl)benzyl]oxy}-1H-indol-3-yl)methylidene]amino}oxy)acetic acid was synthesized using the procedure outlined for example 1 using 3-(trifluoromethyl)benzyl bromide and the resulting ether was further alkylated using methyl iodide.

Example 44

Synthesis of [({(1E)-[5-[(4-chlorobenzyl)oxy]-1-(2-propynyl)-1H-indol-3-yl]methylidene}amino)oxy] acetic acid

[({(1E)-[5-[(4-chlorobenzyl)oxy]-1-(2-propynyl)-1H-indol-3-yl]methylidene}amino)oxy]acetic acid was synthesized using the procedure outlined for example 1 using 4-chlorobenzyl bromide and the resulting ether was further alkylated using propargyl bromide.

Example 45

Synthesis of {[((1E)-{1-allyl-5-[(4-chlorobenzyl)oxy]-1H-indol-3-yl}methylidene)amino]oxy}acetic acid {[((1E)-{1-allyl-5-[(4-chlorobenzyl)oxy]-1H-indol-3-yl}methylidene)amino]oxy}acetic acid was synthesized using the procedure outlined for example 1 using 4-chlorobenzyl bromide and the resulting ether was further alkylated using allyl bromide.

Example 46

Synthesis of {[((1E)-{1-benzyl-5-[(4-chlorobenzyl)oxy]-1H-indol-3-yl}methylidene)amino]oxy}acetic acid {[((1E)-{1-benzyl-5-[(4-chlorobenzyl)oxy]-1H-indol-3-yl}methylidene)amino]oxy}acetic acid was synthesized using the procedure outlined for example 1 using 4-chlorobenzyl bromide and the resulting ether was further alkylated using benzyl bromide.

Example 47

Synthesis of {[((1E)-{5-[(4-chlorobenzyl)oxy]-1-methyl-1H-indol-3-yl}methylidene)amino]oxy}acetic acid {[((1E)-{5-[(4-chlorobenzyl)oxy]-1-methyl-1H-indol-3-yl}methylidene)amino]oxy}acetic acid was synthesized using the procedure outlined for example 1 using 4-chlorobenzyl bromide and the resulting ether was further alkylated using methyl iodide.

Example 48

Synthesis of [({(1E)-[5-[(2-chlorobenzyl)oxy]-1-(2-propynyl)-1H-indol-3-yl]methylidene}amino)oxy] acetic acid

[({(1E)-[5-[(2-chlorobenzyl)oxy]-1-(2-propynyl)-1H-indol-3-yl]methylidene}amino)oxy]acetic acid was synthesized using the procedure outlined for example 1 using 2-chlorobenzyl bromide and the resulting ether was further alkylated using propargyl bromide.

Example 49

Synthesis of {[((1E)-{1-allyl-5-[(2-chlorobenzyl)oxy]-1H-indol-3-yl}methylidene)amino]oxy}acetic acid {[((1E)-{1-allyl-5-[(2-chlorobenzyl)oxy]-1H-indol-3-yl}methylidene)amino]oxy}acetic acid was synthesized using the procedure outlined for example 1 using 2-chlorobenzyl bromide and the resulting ether was further alkylated using allyl bromide.

Example 50

Synthesis of {[((1E)-{5-[(2-chlorobenzyl)oxy]-1-methyl-1H-indol-3-yl}methylidene)amino] oxy}acetic acid {[((1E)-{5-[(2-chlorobenzyl)oxy]-1-methyl-1H-indol-3-yl}methylidene)amino]oxy}acetic acid was synthesized using the procedure outlined for example 1 using 2-chlorobenzyl bromide and the resulting ether was further alkylated using methyl iodide.

Example 51

Synthesis of [({(1E)-[5-[(3,4-dichlorobenzyl)oxy]-1-(2-propynyl)-1H-indol-3-yl]methylidene}amino) oxy]acetic acid

[({(1E)-[5-[(3,4-dichlorobenzyl)oxy]-1-(2-propynyl)-1H-indol-3-yl]methylidene}amino)oxy]acetic acid was synthesized using the procedure outlined for example 1 using 3,4-dichlorobenzyl bromide and the resulting ether was further alkylated using propargyl bromide.

Example 52

Synthesis of {[((1E)-{1-allyl-5-[(3,4-dichlorobenzyl)oxy]-1H-indol-3-yl}methylidene)amino]oxy}acetic acid {[((1E)-{1-allyl-5-[(3,4-dichlorobenzyl)oxy]-1H-indol-3-yl}methylidene)amino]oxy}acetic acid was synthesized using the procedure outlined for example 1 using 3,4-dichlorobenzyl bromide and the resulting ether was further alkylated using allyl bromide.

Example 53

Synthesis of {[((1E)-{1-benzyl-5-[(3,4-dichlorobenzyl)oxy]-1H-indol-3-yl}methylidene)amino] oxy}acetic acid {[((1E)-{1-benzyl-5-[(3,4-dichlorobenzyl)oxy]-1H-indol-3-yl}methylidene)amino]oxy}acetic acid was synthesized using the procedure outlined for example 1 using 3,4-dichlorobenzyl bromide and the resulting ether was further alkylated using benzyl bromide.

Example 54

Synthesis of {[((1E)-{5-[(3,4-dichlorobenzyl)oxy]-1-methyl-1H-indol-3-yl}methylidene)amino]oxy}acetic acid {[((1E)-{5-[(3,4-dichlorobenzyl)oxy]-1-methyl-1H-indol-3-yl}methylidene)amino]oxy}acetic acid was synthesized using the procedure outlined for example 1 using 3,4-dichlorobenzyl bromide and the resulting ether was further alkylated using methyl iodide.

Example 55

Synthesis of [({(1E)-[1-allyl-5-(2-naphthylmethoxy)-1H-indol-3-yl]methylidene}amino)oxy]acetic acid

[({(1E)-[1-allyl-5-(2-naphthylmethoxy)-1H-indol-3-yl]methylidene}amino)oxy]acetic acid was synthesized using the procedure outlined for example 1 using 2-naphthyl bromide and the resulting ether was further alkylated using allyl bromide.

Example 56

Synthesis of [({(1E)-[1-benzyl-5-(2-naphthylmethoxy)-1H-indol-3-yl]methylidene}amino)oxy]acetic acid

[({(1E)-[1-benzyl-5-(2-naphthylmethoxy)-1H-indol-3-yl]methylidene}amino)oxy]acetic acid was synthesized using the procedure outlined for example 1 using 2-naphthyl bromide and the resulting ether was further alkylated using benzyl bromide.

Example 57

Synthesis of [({(1E)-[1-methyl-5-(2-naphthylmethoxy)-1H-indol-3-yl]methylidene}amino)oxy]acetic acid

[({(1E)-[1-methyl-5-(2-naphthylmethoxy)-1H-indol-3-yl]methylidene}amino)oxy]acetic acid was synthesized using the procedure outlined for example 1 using 2-naphthyl bromide and the resulting ether was further alkylated using methyl iodide.

Example 58

Synthesis of ({[((1E)-(3'-{[4-(trifluoromethyl)benzyl]oxy}-1,1'-biphenyl-3-yl)methylidene]amino}oxy)acetic acid Step 1. To a solution of 3-bromophenol (86.5 mg, 0.5 mmol) in acetone was added cesium carbonate (651.6 mg, 2 mmol) and 4-(trifluoromethyl)benzyl bromide (0.120 ml, 0.5 mmol). The reaction mixture was shaken at 60° C. overnight. The mixture was filtered and washed. The solvent was evaporated in vacuo.

Step 2. To a solution of crude benzyl ether (0.5 mmol) obtained from step 1 in ethylene glycol dimethyl ether (DME) (2 ml) in dry reaction vessel was added 3-formylphenylboronic acid (112.5 mg, 0.75 mmol), tetrakis(triphenylphosphine)palladium(0) (28.9 mg, 0.025 mmol), and 2M sodium carbonate solution (1.25 mmol). The reaction mixture was shaken at 80° C. overnight. The mixture was filtered and washed. The solvent was evaporated in vacuo.

Step 3. To a solution of aldehyde (0.25 mmol) from step 2 dissolved in pyridine (0.5 ml) and EtOH (4.5 ml) was added carboxymethoxylamine hemihydrochloride (54.6 mg, 0.25 mmol). The reaction was heated to 60° C. for 2 hours. The solvent was evaporated in vacuo. The crude product was purified by RP-HPLC. $^1$H NMR (DMSO $d_6$, 300 MHz) δ 4.69 (s, 2H), 5.33 (s, 2H), 7.06 (dd, J=8.1, 1.9 Hz, 1H), 7.28 (d, J=7.8 Hz, 2H), 7.33 (s, 1H), 7.42 (t, J=7.9 Hz, 1H), 7.54 (t, J=7.7 Hz, 1H), 7.64 (d, J=6.8 Hz, 1H), 7.67-7.82 (m, 5H), 7.89 (s, 1H), 8.42 (s, 1H), 12.86 (s, 1H); MS: (M+H) 430.1

Example 59

Synthesis of {[((1E)-{3'-[(4-tert-butylbenzyl)oxy]-1,1'-biphenyl-3-yl}methylidene)amino]oxy}acetic acid {[((1E)-{3'-[(4-tert-butylbenzyl)oxy]-1,1'-biphenyl-3-yl}methylidene)amino]oxy}acetic acid was synthesized using the procedure outlined for example 58 using 4-t-butylbenzyl bromide in step 1.

Example 60

Synthesis of {[((1E)-{3'-[(4-bromobenzyl)oxy]-1,1'-biphenyl-3-yl}methylidene)amino]oxy}acetic acid {[((1E)-{3'-[(4-bromobenzyl)oxy]-1,1'-biphenyl-3-yl}methylidene)amino]oxy}acetic acid was synthesized using the procedure outlined for example 58 using 4-bromobenzyl bromide in step 1.

Example 61

Synthesis of ({[(1E)-(3'-{[3,5-bis(trifluoromethyl)benzyl]oxy}-1,1'-biphenyl-3-yl)methylidene]amino}oxy)acetic acid ({[(1E)-(3'-{[3,5-bis(trifluoromethyl)benzyl]oxy}-1,1'-biphenyl-3-yl)methylidene]amino}oxy)acetic was synthesized using the procedure outlined for example 58 using 3,5-bis(trifluoromethyl)benzyl bromide in step 1.

Example 62

Synthesis of {[((1E)-{3'-[(3-bromobenzyl)oxy]-1,1'-biphenyl-3-yl}methylidene)amino]oxy}acetic acid {[((1E)-{3'-[(3-bromobenzyl)oxy]-1,1'-biphenyl-3-yl}methylidene)amino]oxy}acetic acid was synthesized using the procedure outlined for example 58 using 3-bromobenzyl bromide in step 1.

Example 63

Synthesis of {[((1E)-{3'-[(3-chlorobenzyl)oxy]-1,1'-biphenyl-3-yl}methylidene)amino]oxy}acetic acid {[((1E)-{3'-[(3-chlorobenzyl)oxy]-1,1'-biphenyl-3-yl}methylidene)amino]oxy}acetic acid was synthesized using the procedure outlined for example 58 using 3-chlorobenzyl bromide in step 1.

Example 64

Synthesis of [({(1E)-[3'-(benzyloxy)-1,1'-biphenyl-3-yl]methylidene}amino)oxy]acetic acid

[({(1E)-[3'-(benzyloxy)-1,1'-biphenyl-3-yl]methylidene}amino)oxy]acetic acid was synthesized using the procedure outlined for example 58 using benzyl bromide in step 1.

Example 65

Synthesis of ({[(1E)-(3'-{[3-(trifluoromethyl)benzyl]oxy}-1,1'-biphenyl-3-yl)methylidene]amino}oxy)acetic acid ({[(1E)-(3'-{[3-(trifluoromethyl)benzyl]oxy}-1,1'-biphenyl-3-yl)methylidene]amino}oxy)acetic acid was synthesized using the procedure outlined for example 58 using 3-(trifluoromethyl)benzyl bromide in step 1.

Example 66

Synthesis of {[((1E)-{3'-[(4-chlorobenzyl)oxy]-1,1'-biphenyl-3-yl}methylidene)amino]oxy}acetic acid {[((1E)-{3'-[(4-chlorobenzyl)oxy]-1,1'-biphenyl-3-yl}methylidene)amino]oxy}acetic acid was synthesized using the procedure outlined for example 58 using 4-chlorobenzyl bromide in step 1.

Example 67

Synthesis of {[((1E)-{3'-[(2-chlorobenzyl)oxy]-1,1'-biphenyl-3-yl}methylidene)amino]oxy}acetic acid {[((1E)-{3'-[(2-chlorobenzyl)oxy]-1,1'-biphenyl-3-yl}methylidene)amino]oxy}acetic acid was synthesized using the procedure outlined for example 58 using 2-chlorobenzyl bromide in step 1.

Example 68

Synthesis of {[((1E)-{3'-[(3,4-dichlorobenzyl)oxy]-1,1'-biphenyl-3-yl}methylidene)amino]oxy}acetic acid {[((1E)-{3'-[(3,4-dichlorobenzyl)oxy]-1,1'-biphenyl-3-yl}methylidene)amino]oxy}acetic acid was synthesized using the procedure outlined for example 58 using 3,4-dichlorobenzyl bromide in step 1.

Example 69

Synthesis of [({(1E)-[3'-(2-naphthylmethoxy)-1,1'-biphenyl-3-yl]methylidene}amino)oxy]acetic acid

[({(1E)-[3'-(2-naphthylmethoxy)-1,1'-biphenyl-3-yl]methylidene}amino)oxy]acetic acid was synthesized using the procedure outlined for example 58 using 2-naphthylbenzyl bromide in step 1.

Example 70

Synthesis of {[((1E)-{3'-[(4-methylbenzyl)oxy]-1,1'-biphenyl-3-yl}methylidene)amino]oxy}acetic acid {[((1E)-{3'-[(4-methylbenzyl)oxy]-1,1'-biphenyl-3-yl}methylidene)amino]oxy}acetic acid was synthesized using the procedure outlined for example 58 using 4-methylbenzyl bromide in step 1.

Example 71

Synthesis of {[((1E)-{3'-[(3-methylbenzyl)oxy]-1,1'-biphenyl-3-yl}methylidene)amino]oxy}acetic acid {[((1E)-{3'-[(3-methylbenzyl)oxy]-1,1'-biphenyl-3-yl}methylidene)amino]oxy}acetic acid was synthesized using the procedure outlined for example 58 using 3-methylbenzyl bromide in step 1.

Example 72

Synthesis of {[((1E)-{3'-[(2,6-dichlorobenzyl)oxy]-1,1'-biphenyl-3-yl}methylidene)amino]oxy}acetic acid {[((1E)-{3'-[(2,6-dichlorobenzyl)oxy]-1,1'-biphenyl-3-yl}methylidene)amino]oxy}acetic acid was synthesized using the procedure outlined for example 58 using 2,6-dichlorobenzyl bromide in step 1.

Example 73

Synthesis of ({[(1E)-(4'-{[4-(trifluoromethyl)benzyl]oxy}-1,1'-biphenyl-3-yl)methylidene]amino}oxy)acetic acid ({[(1E)-(4'-{[4-(trifluoromethyl)benzyl]oxy}-1,1'-biphenyl-3-yl)methylidene]amino}oxy)acetic acid was synthesized using the procedure outlined for example 58 where 4-bromophenol was used in the step 1.

1H NMR (DMSO d6, 300 MHz) δ 4.68 (s, 2H), 5.30 (s, 2H), 7.14 (d, J=8.8 Hz, 2H), 7.44 (d, J=9.2 Hz, 1H), 7.56-7.71 (m, 6H), 7.78 (d, J=8.3 Hz, 2H), 7.83 (s, 1H), 8.40 (s, 1H), 12.82 (s, 1H); MS: (M+H) 430.0

Example 74

Synthesis of {[((1E)-{4'-[(4-tert-butylbenzyl)oxy]-1,1'-biphenyl-3-yl}methylidene)amino]oxy}acetic acid {[((1E)-{4'-[(4-tert-butylbenzyl)oxy]-1,1'-biphenyl-3-yl}methylidene)amino]oxy}acetic acid was synthesized using the procedure outlined for example 73 using 4-t-butylbenzyl bromide in step 1.

Example 75

Synthesis of {[((1E)-{4'-[(4-bromobenzyl)oxy]-1,1'-biphenyl-3-yl}methylidene)amino]oxy}acetic acid {[((1E)-{4'-[(4-bromobenzyl)oxy]-1,1'-biphenyl-3-yl}methylidene)amino]oxy}acetic acid was synthesized using the procedure outlined for example 73 using 4-bromobenzyl bromide in step 1.

Example 76

Synthesis of ({[(1E)-(4'-{[3,5-bis(trifluoromethyl) benzyl]oxy}-1,1'-biphenyl-3-yl)methylidene] amino}oxy)acetic acid ({[(1E)-(4'-{[3,5-bis(trifluoromethyl)benzyl]oxy}-1,1'-biphenyl-3-yl)methylidene]amino}oxy)acetic acid was synthesized using the procedure outlined for example 73 using 3,5-bis(trifluoromethyl)benzyl bromide in step 1.

Example 77

Synthesis of {[((1E)-{4'-[(3-bromobenzyl)oxy]-1,1'-biphenyl-3-yl}methylidene)amino]oxy}acetic acid {[((1E)-{4'-[(3-bromobenzyl)oxy]-1,1'-biphenyl-3-yl}methylidene)amino]oxy}acetic acid was synthesized using the procedure outlined for example 73 using 3-bromobenzyl bromide in step 1.

Example 78

Synthesis of {[((1E)-{4'-[(3-chlorobenzyl)oxy]-1,1'-biphenyl-3-yl}methylidene)amino]oxy}acetic acid {[((1E)-{4'-[(3-chlorobenzyl)oxy]-1,1'-biphenyl-3-yl}methylidene)amino]oxy}acetic acid was synthesized using the procedure outlined for example 73 using 3-chlorobenzyl bromide in step 1.

Example 79

Synthesis of [({(1E)-[4'-(benzyloxy)-1,1'-biphenyl-3-yl]methylidene}amino)oxy]acetic acid

[({(1E)-[4'-(benzyloxy)-1,1'-biphenyl-3-yl]methylidene}amino)oxy]acetic acid was synthesized using the procedure outlined for example 73 using benzyl bromide in step 1.

Example 80

Synthesis of ({[(1E)-(4'-{[3-(trifluoromethyl)benzyl] oxy}-1,1'-biphenyl-3-yl)methylidene]amino}oxy) acetic acid ({[(1E)-(4'-{[3-(trifluoromethyl)benzyl]oxy}-1,1'-biphenyl-3-yl)methylidene]amino}oxy)acetic acid was synthesized using the procedure outlined for example 73 using 3-(trifluoromethyl)benzyl bromide in step 1.

Example 81

Synthesis of {[((1E)-{4'-[(4-chlorobenzyl)oxy]-1,1'-biphenyl-3-yl}methylidene)amino]oxy}acetic acid {[((1E)-{4'-[(4-chlorobenzyl)oxy]-1,1'-biphenyl-3-yl}methylidene)amino]oxy}acetic was synthesized using the procedure outlined for example 73 using 4-chlorobenzyl bromide in step 1 acid

Example 82

Synthesis of {[((1E)-{4'-[(2-chlorobenzyl)oxy]-1,1'-biphenyl-3-yl}methylidene)amino]oxy}acetic acid {[((1E)-{4'-[(2-chlorobenzyl)oxy]-1,1'-biphenyl-3-yl}methylidene)amino]oxy}acetic acid was synthesized using the procedure outlined for example 73 using 2-chlorobenzyl bromide in step 1.

Example 83

Synthesis of {[((1E)-{4'-[(3,4-dichlorobenzyl)oxy]-1,1'-biphenyl-3-yl}methylidene)amino]oxy}acetic acid {[((1E)-{4'-[(3,4-dichlorobenzyl)oxy]-1,1'-biphenyl-3-yl}methylidene)amino]oxy}acetic acid was synthesized using the procedure outlined for example 73 using 3,4-dichlorobenzyl bromide in step 1.

Example 84

Synthesis of [({(1E)-[4'-(2-naphthylmethoxy)-1,1'-biphenyl-3-yl]methylidene}amino)oxy]acetic acid

[({(1E)-[4'-(2-naphthylmethoxy)-1,1'-biphenyl-3-yl] methylidene}amino)oxy]acetic acid was synthesized using the procedure outlined for example 73 using 2-naphthylbenzyl bromide in step 1.

Example 85

Synthesis of {[((1E)-{4'-[(4-methylbenzyl)oxy]-1,1'-biphenyl-3-yl}methylidene)amino]oxy}acetic acid {[((1E)-{4'-[(4-methylbenzyl)oxy]-1,1'-biphenyl-3-yl}methylidene)amino]oxy}acetic acid was synthesized using the procedure outlined for example 73 using 4-methylbenzyl bromide in step 1.

Example 86

Synthesis of {[((1E)-{4'-[(3-methylbenzyl)oxy]-1,1'-biphenyl-3-yl}methylidene)amino]oxy}acetic acid {[((1E)-{4'-[(3-methylbenzyl)oxy]-1,1'-biphenyl-3-yl}methylidene)amino]oxy}acetic acid was synthesized using the procedure outlined for example 73 using 3-methylbenzyl bromide in step 1.

Example 87

Synthesis of {[((1E)-{4'-[(2,6-dichlorobenzyl)oxy]-1,1'-biphenyl-3-yl}methylidene)amino]oxy}acetic acid {[((1E)-{4'-[(2,6-dichlorobenzyl)oxy]-1,1'-biphenyl-3-yl}methylidene)amino]oxy}acetic acid was synthesized using the procedure outlined for example 73 using 2,6-dichlorobenzyl bromide in step 1.

Example 88

Synthesis of ({[(1E)-(3'-{[4-(trifluoromethyl)benzyl] oxy}-1,1'-biphenyl-4-yl)methylidene]amino}oxy) acetic acid ({[(1E)-(3'-{[4-(trifluoromethyl)benzyl]oxy}-1,1'-biphenyl-4-yl)methylidene]amino}oxy)acetic acid was synthesized using the procedure outlined for example 58 where added 4-formylphenyl boronic acid was used in the step 2. 1H NMR (DMSO d$_6$, 300 MHz) δ 4.68 (s, 2H), 5.33 (s, 2H), 7.06 (d, J=8.0 Hz, 1H), 7.29-7.44 (m, 3H), 7.68-7.79 (m, 8H), 8.39 (s, 1H), 12.80 (s, 1H); MS: (M+H) 430.2

Example 89

Synthesis of {[((1E)-{3'-[(4-tert-butylbenzyl)oxy]-1,1'-biphenyl-4-yl}methylidene)amino]oxy}acetic acid {[((1E)-{3'-[(4-tert-butylbenzyl)oxy]-1,1'-biphenyl-4-yl}methylidene)amino]oxy}acetic acid was synthesized using the procedure outlined for example 88 using 4-t-butylbenzyl bromide in step 1.

Example 90

Synthesis of ({[(1E)-(3'-{[3,5-bis(trifluoromethyl) benzyl]oxy}-1,1'-biphenyl-4-yl)methylidene] amino}oxy)acetic acid ({[(1E)-(3'-{[3,5-bis(trifluoromethyl)benzyl]oxy}-1,1'-biphenyl-4-yl)methylidene]amino}oxy)acetic acid was synthesized using the procedure outlined for example 88 using 3,5-bis(trifluoromethyl)benzyl bromide in step 1.

Example 91

Synthesis of {[((1E)-{3'-[(3-bromobenzyl)oxy]-1,1'-biphenyl-4-yl}methylidene)amino]oxy}acetic acid {[((1E)-{3'-[(3-bromobenzyl)oxy]-1,1'-biphenyl-4-yl}methylidene)amino]oxy}acetic acid was synthesized using the procedure outlined for example 88 using 3-bromobenzyl bromide in step 1.

Example 92

Synthesis of {[((1E)-{3'-[(3-chlorobenzyl)oxy]-1,1'-biphenyl-4-yl}methylidene)amino]oxy}acetic acid {[((1E)-{3'-[(3-chlorobenzyl)oxy]-1,1'-biphenyl-4-yl}methylidene)amino]oxy}acetic acid was synthesized using the procedure outlined for example 88 using 3-chlorobenzyl bromide in step 1.

Example 93

Synthesis of [({(1E)-[3'-(benzyloxy)-1,1'-biphenyl-4-yl]methylidene}amino)oxy]acetic acid

[({(1E)-[3'-(benzyloxy)-1,1'-biphenyl-4-yl] methylidene}amino)oxy]acetic acid was synthesized using the procedure outlined for example 88 using benzyl bromide in step 1.

Example 94

Synthesis of ({[(1E)-(3'-{[3-(trifluoromethyl)benzyl] oxy}-1,1'-biphenyl-4-yl)methylidene]amino}oxy) acetic acid ({[(1E)-(3'-{[3-(trifluoromethyl)benzyl]oxy}-1,1'-biphenyl-4-yl)methylidene]amino}oxy)acetic acid was synthesized using the procedure outlined for example 88 using 3-(trifluoromethyl)benzyl bromide in step 1.

Example 95

Synthesis of {[((1E)-{3'-[(4-chlorobenzyl)oxy]-1,1'-biphenyl-4-yl}methylidene)amino]oxy}acetic acid {[((1E)-{3'-[(4-chlorobenzyl)oxy]-1,1'-biphenyl-4-yl}methylidene)amino]oxy}acetic acid was synthesized using the procedure outlined for example 88 using 4-chlorobenzyl bromide in step 1.

Example 96

Synthesis of {[((1E)-{3'-[(2-chlorobenzyl)oxy]-1,1'-biphenyl-4-yl}methylidene)amino]oxy}acetic acid {[((1E)-{3'-[(2-chlorobenzyl)oxy]-1,1'-biphenyl-4-yl}methylidene)amino]oxy}acetic acid was synthesized using the procedure outlined for example 88 using 2-chlorobenzyl bromide in step 1.

Example 97

Synthesis of {[((1E)-{3'-[(3,4-dichlorobenzyl)oxy]-1,1'-biphenyl-4-yl}methylidene)amino]oxy}acetic acid {[((1E)-{3'-[(3,4-dichlorobenzyl)oxy]-1,1'-biphenyl-4-yl}methylidene)amino]oxy}acetic acid was synthesized using the procedure outlined for example 88 using 3,4-dichlorobenzyl bromide in step 1.

Example 98

Synthesis of [({(1E)-[3'-(2-naphthylmethoxy)-1,1'-biphenyl-4-yl]methylidene}amino)oxy]acetic acid

[({(1E)-[3'-(2-naphthylmethoxy)-1,1'-biphenyl-4-yl] methylidene}amino)oxy]acetic acid was synthesized using the procedure outlined for example 88 using 2-naphthylbenzyl bromide in step 1.

Example 99

Synthesis of {[((1E)-{3'-[(4-methylbenzyl)oxy]-1,1'-biphenyl-4-yl}methylidene)amino]oxy}acetic acid {[((1E)-{3'-[(4-methylbenzyl)oxy]-1,1'-biphenyl-4-yl}methylidene)amino]oxy}acetic acid was synthesized using the procedure outlined for example 88 using 4-methylbenzyl bromide in step 1.

Example 100

Synthesis of {[((1E)-{3'-[(3-methylbenzyl)oxy]-1,1'-biphenyl-4-yl}methylidene)amino]oxy}acetic acid {[((1E)-{3'-[(3-methylbenzyl)oxy]-1,1'-biphenyl-4-yl}methylidene)amino]oxy}acetic acid was synthesized using the procedure outlined for example 88 using 3-methylbenzyl bromide in step 1.

Example 101

Synthesis of {[((1E)-{3'-[(2,6-dichlorobenzyl)oxy]-1,1'-biphenyl-4-yl}methylidene)amino]oxy}acetic acid {[((1E)-{3'-[(2,6-dichlorobenzyl)oxy]-1,1'-biphenyl-4-yl}methylidene)amino]oxy}acetic acid was synthesized using the procedure outlined for example 88 using 2,6-dichlorobenzyl bromide in step 1.

Example 102

Synthesis of {[((1E)-{4'-[(4-tert-butylbenzyl)oxy]-1,1'-biphenyl-4-yl}methylidene)amino]oxy}acetic acid {[((1E)-{4'-[(4-tert-butylbenzyl)oxy]-1,1'-biphenyl-4-yl}methylidene)amino]oxy}acetic acid was synthesized using the procedure outlined for example 58 where 4-bromophenol was used in step 1 and 4-formylphenyl boronic acid was used in the step 2. 1H NMR (DMSO $d_6$, 300 MHz) δ 4.66 (s, 2H), 5.12 (s, 2H), 7.10 (d, J=8.8 Hz, 2H), 7.37-7.44 (m, 4H), 7.64-7.75 (m, 6H), 8.36 (s, 1H), 12.78 (s, 1H); MS: (M+H) 418.2

Example 103

Synthesis of {[((1E)-{4'-[(3-bromobenzyl)oxy]-1,1'-biphenyl-4-yl}methylidene)amino]oxy}acetic acid {[((1E)-{4'-[(3-bromobenzyl)oxy]-1,1'-biphenyl-4-yl}methylidene)amino]oxy}acetic acid was synthesized using the procedure outlined for example 102 using 3-bromobenzyl bromide in step 1.

Example 104

Synthesis of {[((1E)-{4'-[(3-chlorobenzyl)oxy]-1,1'-biphenyl-4-yl}methylidene)amino]oxy}acetic acid {[((1E)-{4'-[(3-chlorobenzyl)oxy]-1,1'-biphenyl-4-yl}methylidene)amino]oxy}acetic acid was synthesized using the procedure outlined for example 102 using 3-chlorobenzyl bromide in step 1.

Example 105

Synthesis of [({(1E)-[4'-(benzyloxy)-1,1'-biphenyl-4-yl]methylidene}amino)oxy]acetic acid

[({(1E)-[4'-(benzyloxy)-1,1'-biphenyl-4-yl]methylidene}amino)oxy]acetic acid was synthesized using the procedure outlined for example 102 using benzyl bromide in step 1.

Example 106

Synthesis of ({[((1E)-(4'-{[3-(trifluoromethyl)benzyl]oxy}-1,1'-biphenyl-4-yl)methylidene]amino}oxy) acetic acid ({[((1E)-(4'-{[3-(trifluoromethyl)benzyl]oxy}-1,1'-biphenyl-4-yl)methylidene]amino}oxy)acetic acid was synthesized using the procedure outlined for example 102 using 3-(trifluoromethyl)benzyl bromide in step 1.

Example 107

Synthesis of {[((1E)-{4'-[(2-chlorobenzyl)oxy]-1,1'-biphenyl-4-yl}methylidene)amino]oxy}acetic acid {[((1E)-{4'-[(2-chlorobenzyl)oxy]-1,1'-biphenyl-4-yl}methylidene)amino]oxy}acetic acid was synthesized using the procedure outlined for example 102 using 2-chlorobenzyl bromide in step 1.

Example 108

Synthesis of {[((1E)-{4'-[(3,4-dichlorobenzyl)oxy]-1,1'-biphenyl-4-yl}methylidene)amino]oxy}acetic acid {[((1E)-{4'-[(3,4-dichlorobenzyl)oxy]-1,1'-biphenyl-4-yl}methylidene)amino]oxy}acetic acid was synthesized using the procedure outlined for example 102 using 3,4-dichlorobenzyl bromide in step 1.

Example 109

Synthesis of {[((1E)-{4'-[(4-methylbenzyl)oxy]-1,1'-biphenyl-4-yl}methylidene)amino]oxy}acetic acid {[((1E)-{4'-[(4-methylbenzyl)oxy]-1,1'-biphenyl-4-yl}methylidene)amino]oxy}acetic acid was synthesized using the procedure outlined for example 102 using 4-methylbenzyl bromide in step 1.

Example 110

Synthesis of {[((1E)-{4'-[(3-methylbenzyl)oxy]-1,1'-biphenyl-4-yl}methylidene)amino]oxy}acetic acid {[((1E)-{4'-[(3-methylbenzyl)oxy]-1,1'-biphenyl-4-yl}methylidene)amino]oxy}acetic acid was synthesized using the procedure outlined for example 102 using 3-methylbenzyl bromide in step 1.

Example 111

Synthesis of {[((1E)-{4'-[(2,6-dichlorobenzyl)oxy]-1,1'-biphenyl-4-yl}methylidene)amino]oxy}acetic acid {[((1E)-{4'-[(2,6-dichlorobenzyl)oxy]-1,1'-biphenyl-4-yl}methylidene)amino]oxy}acetic acid was synthesized using the procedure outlined for example 102 using 2,6-dichlorobenzyl bromide in step 1.

Example 112

Synthesis of {[((1E)-{3,4-bis[(4-tert-butylbenzyl)oxy]phenyl}methylidene)amino]oxy}acetic acid Step 1. To a solution of 3,4-dihydroxybenzaldehyde (69 mg, 0.5 mmol) in acetone was added potassium carbonate (276 mg, 2 mmol) and 4-t-butylbenzyl bromide (0.227 mg, 1.0 mmol). The reaction mixture was shaken at 60° C. overnight. The mixture was filtered and washed. The solvent was evaporated in vacuo.

Step 2. To a solution of crude bisbenzyl ether (0.5 mmol) obtained from step 1 dissolved in pyridine (0.5 ml) and EtOH (4.5 ml) was added carboxymethoxylamine hemihydrochloride (109.2 mg, 0.5 mmol). The reaction was heated to 60° C. for 2 hours. The solvent was evaporated in vacuo. The crude product was purified by RP-HPLC. $^1$H NMR (DMSO d$_6$, 300 MHz) δ 1.28 (s, 18H), 4.61 (s, 2H), 5.07 (s, 2H), 5.12 (s, 2H), 7.13 (m, 2H), 7.32-7.41 (m, 10H), 8.21 (s, 1H); MS: (M+H) 504.

Example 113

Synthesis of {[((1E)-{3,4-bis[(4-fluorobenzyl)oxy]phenyl}methylidene)amino]oxy}acetic acid {[((1E)-{3,4-bis[(4-fluorobenzyl)oxy]phenyl}methylidene)amino]oxy}acetic acid was synthesized using the procedure outlined for example 112 using 4-fluorobenzyl bromide in step 1.

Example 114

Synthesis of ({[(1E)-(3,4-bis{[4-(trifluoromethyl)benzyl]oxy}phenyl)methylidene]amino}oxy)acetic acid ({[(1E)-(3,4-bis{[4-(trifluoromethyl)benzyl]oxy}phenyl)methylidene]amino}oxy)acetic acid was synthesized using the procedure outlined for example 112 using 4-(trifluoromethyl)benzyl bromide in step 1.

Example 115

Synthesis of {[((1E)-{3,4-bis[(4-bromobenzyl)oxy]phenyl}methylidene)amino]oxy}acetic acid {[((1E)-{3,4-bis[(4-bromobenzyl)oxy]phenyl}methylidene)amino]oxy}acetic acid was synthesized using the procedure outlined for example 112 using 4-bromobenzyl bromide in step 1.

Example 116

Synthesis of {[((1E)-{3,4-bis[(3-chlorobenzyl)oxy]phenyl}methylidene)amino]oxy}acetic acid {[((1E)-{3,4-bis[(3-chlorobenzyl)oxy]phenyl}methylidene)amino]oxy}acetic acid was synthesized using the procedure outlined for example 112 using 3-chlorobenzyl in step 1.

Example 117

Synthesis of {[((1E)-{3,4-bis[(3-bromobenzyl)oxy]phenyl}methylidene)amino]oxy}acetic acid {[((1E)-{3,4-bis[(3-bromobenzyl)oxy]phenyl}methylidene)amino]oxy}acetic acid was synthesized using the procedure outlined for example 112 using 3-bromobenzyl bromide in step 1.

Example 118

Synthesis of {[((1E)-{3,4-bis[(3-methylbenzyl)oxy]phenyl}methylidene)amino]oxy}acetic acid {[((1E)-{3,4-bis[(3-methylbenzyl)oxy]phenyl}methylidene)amino]oxy}acetic acid was synthesized using the procedure outlined for example 112 using 3-methylbenzyl bromide in step 1.

Example 119

Synthesis of ({[(1E)-(3,4-bis{[3-(trifluoromethyl)benzyl]oxy}phenyl)methylidene]amino}oxy)acetic acid ({[(1E)-(3,4-bis{[3-(trifluoromethyl)benzyl]oxy}phenyl)methylidene]amino}oxy)acetic acid was synthesized using the procedure outlined for example 112 using 3-(trifluoromethyl)benzyl bromide in step 1.

Example 120

Synthesis of {[((1E)-{3,4-bis[(4-methylbenzyl)oxy]phenyl}methylidene)amino]oxy}acetic acid {[((1E)-{3,4-bis[(4-methylbenzyl)oxy]phenyl}methylidene)amino]oxy}acetic acid was synthesized using the procedure outlined for example 112 using 4-methylbenzyl bromide in step 1.

Example 121

Synthesis of {[((1E)-{3,4-bis[(3,4-difluorobenzyl)oxy]phenyl}methylidene)amino]oxy}acetic acid {[((1E)-{3,4-bis[(3,4-difluorobenzyl)oxy]phenyl}methylidene)amino]oxy}acetic acid was synthesized using the procedure outlined for example 112 using 3,4-difluorobenzyl bromide in step 1.

Example 122

Synthesis of {[((1E)-{2,4-bis[(4-methylbenzyl)oxy]phenyl}methylidene)amino]oxy}acetic acid Step 1. To a solution of 2,4-dihydroxybenzaldehyde (69 mg, 0.5 mmol) in acetone was added potassium carbonate (276 mg, 2 mmol) and 4-methylbenzyl bromide (0.184 mg, 1.0 mmol). The reaction mixture was shaken at 60° C. overnight. The mixture was filtered and washed. The solvent was evaporated in vacuo.

Step 2. To a solution of crude bisbenzyl ether (0.5 mmol) obtained from step 1 dissolved in pyridine (0.5 ml) and EtOH (4.5 ml) was added carboxymethoxylamine hemihydrochloride (109.2 mg, 0.5 mmol). The reaction was heated to 60° C. for 2 hours. The solvent was evaporated in vacuo. The crude product was purified by RP-HPLC. $^1$H NMR (DMSO d$_6$, 300 MHz) δ 2.31 (s, 6H), 4.58 (s, 2H), 5.09 (s, 2H), 5.12 (s, 2H), 6.64 (d, 1H), 6.82 (s, 1H) 7.2 (d, 4H), 7.41 (d, 4H), 7.54 (d, 1H), 8.32 (s, 1H); MS: (M+H) 420.

Example 123

Synthesis of {[((1E)-{2,4-bis[(4-fluorobenzyl)oxy]
phenyl}methylidene)amino]oxy}acetic acid {[((1E)-{2,4-bis[(4-fluorobenzyl)oxy]
phenyl}methylidene)amino]oxy}acetic acid was synthesized using the procedure outlined for example 122 using 4-fluorobenzyl bromide in step 1.

Example 124

Synthesis of ({[((1E)-(2,4-bis{[4-(trifluoromethyl)
benzyl]oxy}phenyl)methylidene]amino}oxy)acetic
acid ({[((1E)-(2,4-bis{[4-(trifluoromethyl)benzyl]oxy}phenyl)
methylidene]amino}oxy)acetic acid was synthesized using the procedure outlined for example 122 using 4-(trifluoromethyl)benzyl bromide in step 1.

Example 125

Synthesis of {[((1E)-{2,4-bis[(4-bromobenzyl)oxy]
phenyl}methylidene)amino]oxy}acetic acid {[((1E)-{2,4-bis[(4-bromobenzyl)oxy]
phenyl}methylidene)amino]oxy}acetic acid was synthesized using the procedure outlined for example 122 using 4-bromobenzyl bromide in step 1.

Example 126

Synthesis of {[((1E)-{2,4-bis[(4-tert-butylbenzyl)
oxy]phenyl}methylidene)amino]oxy}acetic acid {[((1E)-{2,4-bis[(4-tert-butylbenzyl)oxy]
phenyl}methylidene)amino]oxy}acetic acid was synthesized using the procedure outlined for example 122 using 4-t-butylbenzyl bromide in step 1.

Example 127

Synthesis of {[((1E)-{2,4-bis[(3-chlorobenzyl)oxy]
phenyl}methylidene)amino]oxy}acetic acid {[((1E)-{2,4-bis[(3-chlorobenzyl)oxy]
phenyl}methylidene)amino]oxy}acetic acid was synthesized using the procedure outlined for example 122 using 3-chlorobenzyl bromide in step 1.

Example 128

Synthesis of {[((1E)-{2,4-bis[(3-bromobenzyl)oxy]
phenyl}methylidene)amino]oxy}acetic acid {[((1E)-{2,4-bis[(3-bromobenzyl)oxy]
phenyl}methylidene)amino]oxy}acetic acid was synthesized using the procedure outlined for example 122 using 3-bromobenzyl bromide in step 1.

Example 129

Synthesis of {[((1E)-{2,4-bis[(3-methylbenzyl)oxy]
phenyl}methylidene)amino]oxy}acetic acid {[((1E)-{2,4-bis[(3-methylbenzyl)oxy]
phenyl}methylidene)amino]oxy}acetic acid was synthesized using the procedure outlined for example 122 using 3-methylbenzyl bromide in step 1.

Example 130

Synthesis of ({[((1E)-(2,4-bis{[3-(trifluoromethyl)
benzyl]oxy}phenyl)methylidene]amino}oxy)acetic
acid ({[((1E)-(2,4-bis{[3-(trifluoromethyl)benzyl]oxy}phenyl)
methylidene]amino}oxy)acetic acid was synthesized using the procedure outlined for example 122 using 3-(trifluoromethyl)benzyl bromide in step 1.

Example 131

Synthesis of {[((1E)-{2,4-bis[(3,4-difluorobenzyl)
oxy]phenyl}methylidene)amino]oxy}acetic acid {[((1E)-{2,4-bis[(3,4-difluorobenzyl)oxy]
phenyl}methylidene)amino]oxy}acetic acid was synthesized using the procedure outlined for example 122 using 3,4-difluorobenzyl bromide in step 1.

Example 132

Synthesis of {[((1E)-{2,3-bis[(4-bromobenzyl)oxy]
phenyl}methylidene)amino]oxy}acetic acid Step 1. To a solution of 2,3-dihydroxybenzaldehyde (69 mg, 0.5 mmol) in acetone was added potassium carbonate (276 mg, 2 mmol) and 4-bromobenzyl bromide (0.248 mg, 1.0 mmol). The reaction mixture was shaken at 60° C. overnight. The mixture was filtered and washed. The solvent was evaporated in vacuo.

Step 2. To a solution of crude bisbenzyl ether (0.5 mmol) obtained from step 1 dissolved in pyridine (0.5 ml) and EtOH (4.5 ml) was added carboxymethoxylamine hemihydrochloride (109.2 mg, 0.5 mmol). The reaction was heated to 60° C. for 2 hours. The solvent was evaporated in vacuo. The crude product was purified by RP-HPLC. $^1$H NMR (DMSO $d_6$, 300 MHz) δ 4.62 (s, 2H), 4.99 (s, 2H), 5.18 (s, 2H), 7.10 (m, 1H), 7.25 (m, 2H) 7.31 (d, 2H), 7.44 (d, 2H), 7.52 (d, 2H), 7. (d, 2H), 8.29 (s, 1H); MS: (M+H) 550.

Example 133

Synthesis of {[((1E)-{2,3-bis[(4-fluorobenzyl)oxy]
phenyl}methylidene)amino]oxy}acetic acid {[((1E)-{2,3-bis[(4-fluorobenzyl)oxy]
phenyl}methylidene)amino]oxy}acetic acid was synthesized using the procedure outlined for example 132 using 4-fluorobenzyl bromide in step 1.

Example 134

Synthesis of ({[(1E)-(2,3-bis{[4-(trifluoromethyl) benzyl]oxy}phenyl)methylidene]amino}oxy)acetic acid ({[(1E)-(2,3-bis{[4-(trifluoromethyl)benzyl]oxy}phenyl) methylidene]amino}oxy)acetic acid was synthesized using the procedure outlined for example 132 using 4-(trifluoromethyl)benzyl bromide in step 1.

Example 135

Synthesis of {[((1E)-{2,3-bis[(4-tert-butylbenzyl) oxy]phenyl}methylidene)amino]oxy}acetic acid {[((1E)-{2,3-bis[(4-tert-butylbenzyl)oxy] phenyl}methylidene)amino]oxy}acetic acid was synthesized using the procedure outlined for example 132 using 4-t-butylbenzyl bromide step 1.

Example 136

Synthesis of {[((1E)-{2,3-bis[(3-chlorobenzyl)oxy] phenyl}methylidene)amino]oxy}acetic acid {[((1E)-{2,3-bis[(3-chlorobenzyl)oxy] phenyl}methylidene)amino]oxy}acetic acid was synthesized using the procedure outlined for example 132 using 3-chlorobenzyl bromide in step 1.

Example 137

Synthesis of {[((1E)-{2,3-bis[(3-bromobenzyl)oxy] phenyl}methylidene)amino]oxy}acetic acid {[((1E)-{2,3-bis[(3-bromobenzyl)oxy] phenyl}methylidene)amino]oxy}acetic acid was synthesized using the procedure outlined for example 132 using 3-bromobenzyl bromide in step 1.

Example 138

Synthesis of {[((1E)-{2,3-bis[(3-methylbenzyl)oxy] phenyl}methylidene)amino]oxy}acetic acid {[((1E)-{2,3-bis[(3-methylbenzyl)oxy] phenyl}methylidene)amino]oxy}acetic acid was synthesized using the procedure outlined for example 132 using 3-methylbenzyl bromide in step 1.

Example 139

Synthesis of ({[(1E)-(2,3-bis{[3-(trifluoromethyl) benzyl]oxy}phenyl)methylidene]amino}oxy)acetic acid ({[(1E)-(2,3-bis{[3-(trifluoromethyl)benzyl]oxy}phenyl) methylidene]amino}oxy)acetic acid was synthesized using the procedure outlined for example 132 using 3-(trifluoromethyl)benzyl bromide in step 1.

Example 140

Synthesis of {[((1E)-{2,3-bis[(4-methylbenzyl)oxy] phenyl}methylidene)amino]oxy}acetic acid {[((1E)-{2,3-bis[(4-methylbenzyl)oxy] phenyl}methylidene)amino]oxy}acetic acid was synthesized using the procedure outlined for example 132 using 4-methylbenzyl bromide in step 1.

Example 141

Synthesis of {[((1E)-{2,3-bis[(3,4-difluorobenzyl) oxy]phenyl}methylidene)amino]oxy}acetic acid {[((1E)-{2,3-bis[(3,4-difluorobenzyl)oxy] phenyl}methylidene)amino]oxy}acetic acid was synthesized using the procedure outlined for example 132 using 3,4-difluorobenzyl bromide in step 1.

Example 142

Synthesis of {[((1E)-{3,5-bis[(3-chlorobenzyl)oxy] phenyl}methylidene)amino]oxy}acetic acid Step 1. To a solution of 3,5-dihydroxybenzaldehyde (69 mg, 0.5 mmol) in acetone was added potassium carbonate (276 mg, 2 mmol) and 3-chlorobenzyl bromide (0.204 mg, 1.0 mmol). The reaction mixture was shaken at 60° C. overnight. The mixture was filtered and washed. The solvent was evaporated in vacuo.

Step 2. To a solution of crude bisbenzyl ether (0.5 mmol) obtained from step 1 dissolved in pyridine (0.5 ml) and EtOH (4.5 ml) was added carboxymethoxylamine hemihydrochloride (109.2 mg, 0.5 mmol). The reaction was heated to 60° C. for 2 hours. The solvent was evaporated in vacuo. The crude product was purified by RP-HPLC. $^1$H NMR (DMSO $d_6$, 300 MHz) δ 4.64 (s, 2H), 5.13 (s, 4H), 6.77 (s, 1H), 6.91 (s, 2H) 7.40 (s, 6H), 7.45 (s, 2H), 8.26 (s, 1H); MS: (M+H) 460.

Example 143

Synthesis of {[((1E)-{3,5-bis[(4-fluorobenzyl)oxy] phenyl}methylidene)amino]oxy}acetic acid {[((1E)-{3,5-bis[(4-fluorobenzyl)oxy] phenyl}methylidene)amino]oxy}acetic acid was synthesized using the procedure outlined for example 142 using 4-fluorobenzyl bromide in step 1.

Example 144

Synthesis of ({[(1E)-(3,5-bis{[4-(trifluoromethyl) benzyl]oxy}phenyl)methylidene]amino}oxy)acetic acid {[(1E)-(3,5-bis{[4-(trifluoromethyl)benzyl]oxy}phenyl) methylidene]amino}oxy)acetic acid was synthesized using the procedure outlined for example 142 using 4-(trifluoromethyl)benzyl bromide in step 1.

Example 145

Synthesis of {[((1E)-{3,5-bis[(4-bromobenzyl)oxy] phenyl}methylidene)amino]oxy}acetic acid {[((1E)-{3,5-bis[(4-bromobenzyl)oxy] phenyl}methylidene)amino]oxy}acetic acid was synthesized using the procedure outlined for example 142 using 4-bromobenzyl bromide in step 1.

Example 146

Synthesis of {[((1E)-{3,5-bis[(4-tert-butylbenzyl) oxy]phenyl}methylidene)amino]oxy}acetic acid {[((1E)-{3,5-bis[(4-tert-butylbenzyl)oxy] phenyl}methylidene)amino]oxy}acetic acid was synthesized using the procedure outlined for example 142 using 4-t-butylbenzyl bromide in step 1.

Example 147

Synthesis of {[((1E)-{3,5-bis[(3-bromobenzyl)oxy] phenyl}methylidene)amino]oxy}acetic acid {[((1E)-{3,5-bis[(3-bromobenzyl)oxy] phenyl}methylidene)amino]oxy}acetic acid was synthesized using the procedure outlined for example 142 using 3-bromobenzyl bromide in step 1.

Example 148

Synthesis of {[((1E)-{3,5-bis[(3-methylbenzyl)oxy] phenyl}methylidene)amino]oxy}acetic acid {[((1E)-{3,5-bis[(3-methylbenzyl)oxy] phenyl}methylidene)amino]oxy}acetic acid was synthesized using the procedure outlined for example 142 using 3-methylbenzyl bromide in step 1.

Example 149

Synthesis of ({[(1E)-(3,5-bis{[3-(trifluoromethyl) benzyl]oxy}phenyl)methylidene]amino}oxy)acetic acid ({[(1E)-(3,5-bis{[3-(trifluoromethyl)benzyl]oxy}phenyl) methylidene]amino}oxy)acetic acid was synthesized using the procedure outlined for example 142 using 3-(trifluoromethyl)benzyl bromide in step 1.

Example 150

Synthesis of {[((1E)-{3,5-bis[(4-methylbenzyl)oxy] phenyl}methylidene)amino]oxy}acetic acid {[((1E)-{3,5-bis[(4-methylbenzyl)oxy] phenyl}methylidene)amino]oxy}acetic acid was synthesized using the procedure outlined for example 142 using 4-methylbenzyl bromide in step 1.

Example 151

Synthesis of {[((1E)-{3,5-bis[(3,4-difluorobenzyl) oxy]phenyl}methylidene)amino]oxy}acetic acid {[((1E)-{3,5-bis[(3,4-difluorobenzyl)oxy] phenyl}methylidene)amino]oxy}acetic acid was synthesized using the procedure outlined for example 142 using 3,4-difluorobenzyl bromide in step 1.

Example 152

Synthesis of ({[(1E)-(2,5-bis{[3-(trifluoromethyl) benzyl]oxy}phenyl)methylidene]amino}oxy)acetic acid Step 1. To a solution of 2,5-dihydroxybenzaldehyde (69 mg, 0.5 mmol) in acetone was added potassium carbonate (276 mg, 2 mmol) and 3-trifluoromethylbenzyl bromide (0.240 mg, 1.0 mmol). The reaction mixture was shaken at 60° C. overnight. The mixture was filtered Step 2. To a solution of crude bisbenzyl ether (0.5 mmol) obtained from step 1 dissolved in pyridine (0.5 ml) and EtOH (4.5 ml) was added carboxymethoxylamine hemihydrochloride (109.2 mg, 0.5 mmol). The reaction was heated to 60° C. for 2 hours. The solvent was evaporated in vacuo. The crude product was purified by RP-HPLC. $^1$H NMR (DMSO d$_6$, 300 MHz) δ 4.64 (s, 2H), 5.18 (s, 2H), 5.25 (s, 2H), 7.12-7.19 (m, 2H), 7.27 (s, 1H) 7.64-7.82 (m, 8H), 8.44 (s, 1H); MS: (M+H) 528.

Example 153

Synthesis of {[((1E)-{2,5-bis[(4-fluorobenzyl)oxy] phenyl}methylidene)amino]oxy}acetic acid {[((1E)-{2,5-bis[(4-fluorobenzyl)oxy] phenyl}methylidene)amino]oxy}acetic acid was synthesized using the procedure outlined for example 152 using 4-fluorobenzyl bromide in step 1.

Example 154

Synthesis of ({[(1E)-(2,5-bis{[4-(trifluoromethyl) benzyl]oxy}phenyl)methylidene]amino}oxy)acetic acid ({[(1E)-(2,5-bis{[4-(trifluoromethyl)benzyl]oxy}phenyl) methylidene]amino}oxy)acetic acid was synthesized using the procedure outlined for example 152 using 4-(trifluoromethyl)benzyl bromide in step 1.

Example 155

Synthesis of {[((1E)-{2,5-bis[(4-bromobenzyl)oxy] phenyl}methylidene)amino]oxy}acetic acid {[((1E)-{2,5-bis[(4-bromobenzyl)oxy] phenyl}methylidene)amino]oxy}acetic acid was synthesized using the procedure outlined for example 152 using 4-bromobenzyl bromide in step 1.

Example 156

Synthesis of {[((1E)-{2,5-bis[(4-tert-butylbenzyl) oxy]phenyl}methylidene)amino]oxy}acetic acid {[((1E)-{2,5-bis[(4-tert-butylbenzyl)oxy] phenyl}methylidene)amino]oxy}acetic acid was synthesized using the procedure outlined for example 152 using 4-t-butylbenzyl bromide in step 1.

Example 157

Synthesis of {[((1E)-{2,5-bis[(3-chlorobenzyl)oxy] phenyl}methylidene)amino]oxy}acetic acid {[((1E)-{2,5-bis[(3-chlorobenzyl)oxy] phenyl}methylidene)amino]oxy}acetic acid was synthesized using the procedure outlined for example 152 using 3-chlorobenzyl bromide in step 1.

Example 158

Synthesis of {[((1E)-{2,5-bis[(3-bromobenzyl)oxy] phenyl}methylidene)amino]oxy}acetic acid {[((1E)-{2,5-bis[(3-bromobenzyl)oxy] phenyl}methylidene)amino]oxy}acetic acid was synthesized using the procedure outlined for example 152 using 3-bromobenzyl bromide in step 1.

Example 159

Synthesis of {[((1E)-{2,5-bis[(3-methylbenzyl)oxy] phenyl}methylidene)amino]oxy}acetic acid {[((1E)-{2,5-bis[(3-methylbenzyl)oxy] phenyl}methylidene)amino]oxy}acetic acid was synthesized using the procedure outlined for example 152 using 3-methylbenzyl bromide in step 1.

Example 160

Synthesis of {[((1E)-{2,5-bis[(4-methylbenzyl)oxy] phenyl}methylidene)amino]oxy}acetic acid {[((1E)-{2,5-bis[(4-methylbenzyl)oxy] phenyl}methylidene)amino]oxy}acetic acid was synthesized using the procedure outlined for example 152 using 4-methylbenzyl bromide in step 1.

Example 161

Synthesis of {[((1E)-{2,5-bis[(3,4-difluorobenzyl) oxy]phenyl}methylidene)amino]oxy}acetic acid {[((1E)-{2,5-bis[(3,4-difluorobenzyl)oxy] phenyl}methylidene)amino]oxy}acetic acid was synthesized using the procedure outlined for example 152 using 3,4-difluorobenzyl bromide in step 1.

Example 162

Synthesis of {[((1E)-{4-[3-(4-tert-butylphenoxy) prop-1-ynyl]phenyl}methylidene)amino]oxy}acetic acid Step 1. 4-bromobenzaldehyde (20 mmole) was taken in 1:1 diemthoxyethane and water (50 Ml). To it was added 50 mmole of potassium carbonate was added followed by triphenyl phosphine (1.6 mmole), 0.4 mmole of 10% Palladium on Carbon and 0.8 mmole of copper (I) iodide at room temperature. The mixture was stirred at room temperature for 1 hour. To it was added propargyl alcohol (50 mmole) and the reaction mixture was heated overnight. The reaction mixture was cooled to room temperature and filtered through a pad of celite anc concentrated. The residual oil was purified by flash column chromatography using 10% EtOAc in hexane.

Step 2. The alcohol (1 mmole) from step 1 was dissolved in THF and treated with triphenyl phosphine (1 mmole), diethylazodicarboxylate (1 mmole) and 4-t-butylphenol and stirred at room temperature overnight. The reaction mixture was concentrated and purified by flash column chromatography (20% EtOAc in hexane).

Step 3. To a solution of the aldehyde from step 2 (0.5 mmol) dissolved in pyridine (0.5 ml) and EtOH (4.5 ml) was added carboxymethoxylamine hemihydrochloride (54.6 mg, 0.25 mmol). The reaction was heated to 60° C. for 2 hours. The solvent was evaporated in vacuo. The crude product was purified by RP-HPLC.

Examples 163

Synthesis of {[((1E)-{4-[3-(4-bromophenoxy)prop-1-ynyl]phenyl}methylidene)amino]oxy}acetic acid {[((1E)-{4-[3-(4-bromophenoxy)prop-1-ynyl] phenyl}methylidene)amino]oxy}acetic acid was synthesized using the procedure outlined for example 162, but using 4-bromophenol for the Mitsunobu reaction in step 2.

Examples 164

Synthesis of ({[(1E)-(4-{3-[3,5-bis(trifluoromethyl) phenoxy]prop-1-ynyl}phenyl)methylidene] amino}oxy)acetic acid ({[(1E)-(4-{3-[3,5-bis(trifluoromethyl)phenoxy]prop-1-ynyl}phenyl)methylidene]amino}oxy)acetic acid was synthesized using the procedure outlined for example 162, but using 3,5-bistrifluoromethyl phenol for the Mitsunobu reaction in step 2.

Examples 165

Synthesis of {[((1E)-{4-[3-(3,5-dichlorophenoxy) prop-1-ynyl]phenyl}methylidene)amino]oxy}acetic acid {[((1E)-{4-[3-(3,5-dichlorophenoxy)prop-1-ynyl] phenyl}methylidene)amino]oxy}acetic acid was synthesized using the procedure outlined for example 162, but using 3,5-dichlorophenol for the Mitsunobu reaction in step 2.

Examples 166

Synthesis of {[((1E)-{4-[3-(3-chlorophenoxy)prop-1-ynyl]phenyl}methylidene)amino]oxy}acetic acid {[((1E)-{4-[3-(3-chlorophenoxy)prop-1-ynyl]phenyl}methylidene)amino]oxy}acetic acid was synthesized using the procedure outlined for example 162, but using 3-chlorophenol for the Mitsunobu reaction in step 2.

Examples 167

Synthesis of {[((1E)-{4-[3-(4-isobutylphenoxy)prop-1-ynyl]phenyl}methylidene)amino]oxy}acetic acid {[((1E)-{4-[3-(4-isobutylphenoxy)prop-1-ynyl]phenyl}methylidene)amino]oxy}acetic acid was synthesized using the procedure outlined for example 162, but using 4 4-sec-butyl phenol for the Mitsunobu reaction in step 2.

Examples 168

Synthesis of {[((1E)-{3-[3-(4-tert-butylphenoxy)prop-1-ynyl]phenyl}methylidene)amino]oxy}acetic acid {[((1E)-{3-[3-(4-tert-butylphenoxy)prop-1-ynyl]phenyl}methylidene)amino]oxy}acetic acid was synthesized using the procedure outlined for example 162, but using 3-bromobenzaldehyde in step 1 and using 4-t-butylphenol for the Mitsunobu reaction in step 2.

Examples 169

Synthesis of {[((1E)-{3-[3-(4-bromophenoxy)prop-1-ynyl]phenyl}methylidene)amino]oxy}acetic acid {[((1E)-{3-[3-(4-bromophenoxy)prop-1-ynyl]phenyl}methylidene)amino]oxy}acetic acid was synthesized using the procedure outlined for example 162, but using 3-bromobenzaldehyde in step 1 and 4-bromophenol for the Mitsunobu reaction in step 2.

Examples 170

Synthesis of ({[(1E)-(3-{3-[3,5-bis(trifluoromethyl)phenoxy]prop-1-ynyl}phenyl)methylidene]amino}oxy)acetic acid ({[(1E)-(3-{3-[3,5-bis(trifluoromethyl)phenoxy]prop-1-ynyl}phenyl)methylidene]amino}oxy)acetic acid was synthesized using the procedure outlined for example 162, but using 3-bromobenzaldehyde in step 1 and using 3,5-bistrifluoromethyl phenol for the Mitsunobu reaction in step 2.

Examples 171

Synthesis of {[((1E)-{3-[3-(3,5-dichlorophenoxy)prop-1-ynyl]phenyl}methylidene)amino]oxy}acetic acid {[((1E)-{3-[3-(3,5-dichlorophenoxy)prop-1-ynyl]phenyl}methylidene)amino]oxy}acetic acid was synthesized using the procedure outlined for example 162, but using 3-bromobenzaldehyde in step 1 and using 3,5-dichlorophenol for the Mitsunobu reaction in step 2.

Examples 172

Synthesis of {[((1E)-{3-[3-(3-chlorophenoxy)prop-1-ynyl]phenyl}methylidene)amino]oxy}acetic acid {[((1E)-{3-[3-(3-chlorophenoxy)prop-1-ynyl]phenyl}methylidene)amino]oxy}acetic acid was synthesized using the procedure outlined for example 162, but using 3-chlorophenol for the Mitsunobu reaction in step 2.

Examples 173

Synthesis of {[((1E)-{3-[3-(4-isobutylphenoxy)prop-1-ynyl]phenyl}methylidene)amino]oxy}acetic acid {[((1E)-{3-[3-(4-isobutylphenoxy)prop-1-ynyl]phenyl}methylidene)amino]oxy}acetic acid was synthesized using the procedure outlined for example 162, but using 3-bromobenzaldehyde in step 1 and using 4-sec-butyl phenol for the Mitsunobu reaction in step 2.

Example 174

Screening for PAI-1 inhibition. Test compounds are dissolved in DMSO at a final concentration of 10 Mm, then diluted 100× in physiologic buffer. The inhibitory assay is initiated by the addition of the test compound (1-100 µM final concentration, maximum DMSO concentration of 0.2%) in a Ph 6.6 buffer containing 140 Nm recombinant human plasminogen activator inhibitor-1 (PAI-1; Molecular Innovations, Royal Oak, Mich.). Following a 1 hour incubation at room temperature, 70 Nm of recombinant human tissue plasminogen activator (Tpa) is added, and the combination of the test compound, PAI-1 and Tpa is incubated for an additional 30 minutes. Following the second incubation, Spectrozyme-Tpa (American Diagnostica, Greenwich, Conn.), a chromogenic substrate for Tpa, is added and absorbance read at 405 nm at 0 and 60 minutes. Relative PAI-1 inhibition is equal to the residual Tpa activity in the presence of the test compounds and PAI-1. Control treatments include the complete inhibition of Tpa by PAI-1 at the molar ratio employed (2:1), and the absence of any effect of the test compound on Tpa alone.

Example 175

Assay for determining the $IC_{50}$ of inhibition of PAI-1. This assay is based upon the non-SDS dissociable interaction between Tpa and active PAI-1. Assay plates are initially coated with human Tpa (10 µg/ml). Test compounds are dissolved in DMSO at 10 Mm, then diluted with physiologic buffer (Ph 7.5) to a final concentration of 1-50 µM. The test compounds are incubated with human PAI-1 (50 ng/ml) for 15 minutes at room temperature. The Tpa-coated plate is washed with a solution of 0.05% Tween 20 and 0.1% BSA, then the plate is blocked with a solution of 3% BSA. An aliquot of the test compound/PAI-1 solution is then added to the Tpa-coated plate, incubated at room temperature for 1 hour, and washed. Active PAI-1 bound to the plate is assessed by adding an aliquot of a 1:1000 dilution of the 33B8 monoclonal antibody against human PAI-1, and incubating the plate at room temperature for 1 hour (Molecular Innovations, Royal Oak, Mich.). The plate is again washed, and a solution of goat anti-mouse IgG-alkaline phosphatase conjugate is added at a 1:50,000 dilution in goat serum. The plate is incubated 30 minutes at room temperature, washed, and a solution of alkaline phosphatase substrate is added. The plate is incubated 45 minutes at room temperature, and color development is determined at OD405 nm. The quantitation of active PAI-1 bound to Tpa at varying concentrations of the test compound is used to determine the $IC_{50}$. Results are analyzed using a logarithmic best-fit equation. The assay sensitivity is 5 ng/ml of human PAI-1 as determined from a standard curve ranging from 0-100 ng/ml.

Representative compounds of the present invention inhibited Plasminogen Activator Inhibitor-1 as summarized in Table I.

TABLE 1

| COMPOUND | % INHIBITION @ 100 Um | $IC_{50}$ |
| --- | --- | --- |
| 1 | 86 | |
| 2 | 83 | |
| 3 | 82 | 1.85 (K) |
| 4 | 83 | |
| 5 | 93 | |
| 6 | 68 | |
| 7 | 83 | |
| 8 | 63 | |
| 9 | 85 | 16.9 (K) |
| 10 | 86 | |
| 11 | 71 | |
| 12 | 57 | |
| 13 | 95 | |
| 14 | 80 | |
| 15 | 71 | |
| 16 | 58 | |
| 17 | 68 | |
| 18 | 84 | |
| 19 | 73 | |
| 20 | 44 | |
| 21 | 80 | |
| 22 | 80 | |
| 23 | 56 | |
| 24 | 79 | |
| 25 | 68 | |
| 26 | 26 | |
| 27 | 99 | |
| 28 | 70 | |
| 29 | 82 | |
| 30 | 11 | |
| 31 | 90 | |
| 32 | 82 | 9.36 (K) |
| 33 | 91 | |
| 34 | 88 | |
| 35 | 44 | |
| 36 | 92 | |
| 37 | 70 | |
| 38 | 62 | |
| 39 | 48 | |
| 40 | 50 | |
| 41 | 96 | |
| 42 | 96 | |
| 43 | 81 | |
| 44 | 83 | |
| 45 | 96 | |
| 46 | 86 | |
| 47 | 31 | |
| 48 | 79 | |
| 49 | 93 | |
| 50 | 31 | |
| 51 | 86 | |
| 52 | 72 | |
| 53 | 76 | |
| 54 | 91 | |
| 55 | 81 | |
| 56 | 62 | |
| 57 | 64 | |
| 58 | 84 | |
| 59 | 63 | |
| 60 | 88 | |
| 61 | 74 | |
| 62 | 84 | |
| 63 | 91 | |
| 64 | 92 | |

TABLE 1-continued

| COMPOUND | % INHIBITION @ 100 Um | $IC_{50}$ |
| --- | --- | --- |
| 65 | 84 | |
| 66 | 84 | |
| 67 | 87 | |
| 68 | 83 | |
| 69 | 53 | |
| 70 | 83 | |
| 71 | 85 | |
| 72 | 88 | |
| 73 | 59 | |
| 74 | 34 | |
| 75 | 75 | |
| 76 | 73 | |
| 77 | 85 | |
| 78 | 23 | |
| 79 | 53 | |
| 80 | 78 | |
| 81 | 28 | |
| 82 | 89 | |
| 83 | 57 | |
| 84 | 30 | |
| 85 | 34 | |
| 86 | 22 | |
| 87 | 85 | |
| 88 | 34 | |
| 89 | 57 | |
| 90 | 30 | |
| 91 | 77 | |
| 92 | 76 | |
| 93 | 85 | |
| 94 | 74 | |
| 95 | 27 | |
| 96 | 61 | |
| 97 | 65 | |
| 98 | 46 | |
| 99 | 84 | |
| 100 | 63 | |
| 101 | 10 | |
| 102 | 26 | |
| 103 | 62 | |
| 104 | 5 | |
| 105 | 5 | |
| 106 | 8 | |
| 107 | 30 | |
| 108 | 58 | |
| 109 | 7 | |
| 110 | 6 | |
| 111 | 38 | |
| 112 | 65 | |
| 113 | 91 | |
| 114 | 93 | |
| 115 | 87 | |
| 116 | 92 | |
| 117 | 88 | |
| 118 | 92 | |
| 119 | 93 | |
| 120 | 78 | |
| 121 | 72 | |
| 122 | 87 | |
| 123 | 72 | |
| 124 | 95 | |
| 125 | 90 | |
| 126 | 77 | |
| 127 | 88 | |
| 128 | 91 | |
| 129 | 90 | |
| 130 | 91 | |
| 131 | 88 | |
| 132 | 65 | |
| 133 | 20 | |
| 134 | 100 | |
| 135 | 58 | |
| 136 | 80 | |
| 137 | 79 | |
| 138 | 88 | |
| 139 | 90 | |
| 140 | 94 | |

TABLE 1-continued

| COMPOUND | % INHIBITION @ 100 Um | IC$_{50}$ |
|---|---|---|
| 141 | 48 | |
| 142 | 86 | |
| 143 | 95 | |
| 144 | 93 | |
| 145 | 100 | |
| 146 | 49 | |
| 147 | 87 | |
| 148 | 88 | |
| 149 | 91 | |
| 150 | 90 | |
| 151 | 88 | |
| 152 | 100 | |
| 153 | 96 | |
| 154 | 91 | |
| 155 | 85 | |
| 156 | 99 | |
| 157 | 85 | |
| 158 | 69 | |
| 159 | 69 | |
| 160 | 76 | |
| 161 | 92 | |
| 162 | 51 | |
| 163 | 65 | |
| 164 | 73 | |
| 165 | 68 | |
| 166 | 42 | |
| 167 | 53 | |
| 168 | 52 | |
| 169 | 60 | |
| 170 | 73 | |
| 171 | 69 | |
| 172 | 44 | |
| 173 | 56 | |

Example 176

Representative Substituted Indolymethyl Acetic Acid Derivatives

TABLE 2

| Compound | R$_6$ | R$_{24}$ | LC$^1$ @ 254 (min) | MS (M + H) |
|---|---|---|---|---|
| 1 | allyl | 4-CF3 | 3.645 | 433.0 |
| 2 | Ethyl | 4-CF3 | 3.579 | 421.0 |
| 3 | benzyl | 4-CF3 | 3.830 | 483.1 |
| 4 | allyl | 4-t-Bu | 3.884 | 421.1 |
| 5 | Ethyl | 4-t-Bu | 3.827 | 409.1 |
| 6 | benzyl | 4-t-Bu | 4.068 | 471.1 |
| 7 | allyl | 4-Br | 3.062 | 445.0 |
| 8 | Ethyl | 4-Br | 3.535 | 433.0 |
| 9 | benzyl | 4-Br | 3.811 | 495.0 |
| 10 | allyl | 3,5-bis CF3 | 3.893 | 501.0 |
| 11 | Ethyl | 3,5-bis CF3 | 3.837 | 489.0 |
| 12 | benzyl | 3,5-bis CF3 | 4.058 | 551.2 |
| 13 | allyl | 3-Br | 3.585 | 445.0 |
| 14 | Ethyl | 3-Br | 3.518 | 433.0 |
| 15 | benzyl | 3-Br | 3.795 | 495.0 |
| 16 | allyl | 3-Cl | 3.537 | 399.0 |
| 17 | Ethyl | 3-Cl | 3.468 | 387.0 |
| 18 | benzyl | 3-Cl | 3.750 | 449.0 |
| 19 | allyl | 4-Me | 3.470 | 379.1 |
| 20 | Ethyl | 4-Me | 3.398 | 367.1 |
| 21 | benzyl | 4-Me | 3.686 | 429.1 |
| 22 | allyl | 3-CF3 | 3.736 | 433.0 |
| 23 | Ethyl | 3-CF3 | 3.544 | 421.0 |
| 24 | benzyl | 3-CF3 | 3.795 | 483.1 |
| 25 | allyl | 3-Me | 3.477 | 379.1 |
| 26 | Ethyl | 3-Me | 3.403 | 367.1 |
| 27 | benzyl | 3-Me | 3.692 | 438.1 |
| 28 | Ethyl | 2-Cl | 3.420 | 387.0 |
| 29 | benzyl | 2-Cl | 3.710 | 449.0 |
| 30 | H | 2-Cl | 3.016 | 359.0 |
| 31 | Propargyl | 4-CF3 | 3.463 | 431.3 |
| 32 | Me | 4-CF3 | 3.403 | 407.1 |
| 33 | Propargyl | 4-t-Bu | 3.737 | 419.1 |
| 34 | Me | 4-t-Bu | 3.651 | 395.1 |
| 35 | Propargyl | 3,5-bis CF3 | 3.720 | 499.0 |
| 36 | Propargyl | 3-Br | 3.398 | 441.1 |
| 37 | Me | 3-Br | 3.339 | 417.3 |
| 38 | Propargyl | 3-Cl | 3.359 | 397.1 |
| 39 | Me | 3-Cl | 3.290 | 373.1 |
| 40 | Allyl | H | 3.419 | 365.0 |
| 41 | benzyl | H | 3.511 | 415.4 |
| 42 | Propargyl | 3-CF3 | 3.428 | 431.0 |
| 43 | Me | 3-CF3 | 3.382 | 407.4 |
| 44 | Propargyl | 4-Cl | 3.366 | 397.0 |
| 45 | Allyl | 4-Cl | 3.523 | 399.0 |
| 46 | benzyl | 4-Cl | 3.730 | 449.1 |
| 47 | Me | 4-Cl | 3.300 | 373.4 |
| 48 | Propargyl | 2-Cl | 3.308 | 397.0 |
| 49 | Allyl | 2-Cl | 3.463 | 399.0 |
| 50 | Me | 2-Cl | 3.238 | 373.4 |
| 51 | Propargyl | 3,4-diCl | 3.582 | 431.0 |
| 52 | Allyl | 3,4-diCl | 3.718 | 433.3 |
| 53 | benzyl | 3,4-diCl | 3.937 | 483.0 |
| 54 | Me | 3,4-diCl | 3.505 | 407.3 |
| 55 | Allyl | 2-naphthyl | 3.596 | 415.1 |
| 56 | benzyl | 2-naphthyl | 3.796 | 465.4 |
| 57 | Me | 2-naphthyl | 3.390 | 389.4 |

[1]LC Conditions: HP 1100; 40° C.; 5 µL injected; Column: YMC PRO, 2.1×50, 5µ; Gradient A: 0.02% TFA/Water, B: 0.02% TFA/Acetonitrile; Time 0 min: 90% A & 10% B; 5 min: 90% A & 10% B; Post time 1 min; Flow Rate 1.3 ml/min; Detection: 220 and 254 DAD and MSD positive mode.

Example 177

Representative Substituted Biphenylmethylidene Acetic Acid Derivatives

TABLE 3

| Compound | R | LC¹ @ 220 (min) | MS² (M + H) |
|---|---|---|---|
| 58 | 4-CF3 | 3.755 | 430.1 |
| 59 | 4-t-Bu | 4.067 | 418.2 |
| 60 | 4-Br | 3.794 | 440.0 |
| 61 | 3,5-bis CF3 | 3.953 | 498.2 |
| 62 | 3-Br | 3.771 | 440.2 |
| 63 | 3-Cl | 3.725 | 396.0 |
| 64 | H | 3.523 | 361.1 |
| 65 | 3-CF3 | 3.721 | 430.1 |
| 66 | 4-Cl | 3.728 | 396.1 |
| 67 | 2-Cl | 3.695 | 396.1 |
| 68 | 3,4-di Cl | 3.929 | 429.9 |
| 69 | 2-naphthyl | 3.830 | 412.2 |
| 70 | 4-Me | 3.682 | 376.1 |
| 71 | 3-Me | 3.678 | 376.2 |
| 72 | 2,6-di Cl | 3.744 | 430.0 |

¹LC Conditions: HP 1100; 23° C.; 10 µL injected; Column: YMC ODS-AM, 4.6×50, 5µ; Gradient A: 0.05% TFA/Water, B: 0.05% TFA/Acetonitrile; Time 0 min: 98% A & 2% B; 0.3 min: 95% A & 5% B; 3.8 min: 10% A & 90% B; 4.7 min: 10% A & 90% B; 1.9 min: 95% A & 5% B; Flow Rate 3 ml/min; Detection: 220 and 254 DAD ²MS Conditions: Micromass Quatro

TABLE 4

| Compound | R | LC¹ @ 220 (min) | MS² (M + H) |
|---|---|---|---|
| 73 | 4-CF3 | 3.766 | 430.0 |
| 74 | 4-t-Bu | 4.061 | 418.1 |
| 75 | 4-Br | 3.799 | 441.9 |
| 76 | 3,5-bis CF3 | 3.951 | 498.2 |
| 77 | 3-Br | 3.767 | 439.9 |
| 78 | 3-Cl | 3.737 | 396.2 |
| 79 | H | 3.496 | 362.1 |
| 80 | 3-CF3 | 3.739 | 430.0 |
| 81 | 4-Cl | 3.739 | 396.1 |

TABLE 4-continued

| Compound | R | LC¹ @ 220 (min) | MS² (M + H) |
|---|---|---|---|
| 82 | 2-Cl | 3.721 | 396.1 |
| 83 | 3,4-di Cl | 3.951 | 430.0 |
| 84 | 2-naphthyl | 3.855 | 412.2 |
| 85 | 4-Me | 3.698 | 376.2 |
| 86 | 3-Me | 3.710 | 376.2 |
| 87 | 2,6-di Cl | 3.787 | 430.1 |

TABLE 5

| Compound | R | LC¹ @ 220 (min) | MS² (M + H) |
|---|---|---|---|
| 88 | 4-CF3 | 3.758 | 430.2 |
| 89 | 4-t-Bu | 4.095 | 418.2 |
| 90 | 3,5-bis CF3 | 3.932 | 498.2 |
| 91 | 3-Br | 3.788 | 440.1 |
| 92 | 3-Cl | 3.745 | 396.1 |
| 93 | H | 3.543 | 362.2 |
| 94 | 3-CF3 | 3.743 | 430.1 |
| 95 | 4-Cl | 3.754 | 396.0 |
| 96 | 2-Cl | 3.737 | 396.1 |
| 97 | 3,4-di Cl | 3.934 | 430.0 |
| 98 | 2-naphthyl | 3.850 | 412.1 |
| 99 | 4-Me | 3.709 | 376.1 |
| 100 | 3-Me | 3.686 | 376.1 |
| 101 | 2,6-di Cl | 3.772 | 430.0 |

TABLE 6

| Compound | R | LC¹ @ 220 (min) | MS² (M + H) |
|---|---|---|---|
| 102 | 4-CF3 | 4.066 | 418.2 |
| 103 | 3-Br | 3.770 | 440.0 |
| 104 | 3-Cl | 3.724 | 396.0 |
| 105 | H | 3.517 | 361.9 |
| 106 | 3-CF3 | 3.723 | 430.0 |
| 107 | 2-Cl | 3.762 | 396.0 |
| 108 | 3,4-di Cl | 3.938 | 430.0 |
| 109 | 4-Me | 3.686 | 376.0 |

TABLE 6-continued

[Structure: biphenyl with RC6H4CH2O- group and -CH=N-O-CH2-COOH]

| Compound | R | LC[1] @ 220 (min) | MS[2] (M + H) |
|---|---|---|---|
| 110 | 3-Me | 3.689 | 376.1 |
| 111 | 2,6-di Cl | 3.785 | 430.0 |

Example 178

Representative Substituted Bisbenzyloxyphenylmethylidene Acetic Acid Derivatives

TABLE 7

[Structure: central phenyl with two RC6H4CH2O- substituents and -CH=N-O-CH2-COOH]

| Compound | BnO— substitution | R | LC @ 254 (min) | MS (M + H) |
|---|---|---|---|---|
| 112 | 3,4 | 4-t-Bu | 4.798 | 504 |
| 113 | 3,4 | 4-F | 3.776 | 428 |
| 114 | 3,4 | 4-CF3 | 4.247 | 528 |
| 115 | 3,4 | 4-Br | 4.267 | 550 |
| 116 | 3,4 | 3-Cl | 4.142 | 460 |
| 117 | 3,4 | 3-Br | 4.239 | 550 |
| 118 | 3,4 | 3-Me | 4.033 | 420 |
| 119 | 3,4 | 3-CF3 | 4.210 | 528 |
| 120 | 3,4 | 4-Me | 4.023 | 420 |
| 121 | 3,4 | 3,4-diF | 3.899 | 464 |
| 122 | 2,4 | 4-Me | 4.207 | 420 |
| 123 | 2,4 | 4-F | 3.913 | 428 |
| 124 | 2,4 | 4-CF3 | 4.343 | 528 |
| 125 | 2,4 | 4-Br | 4.365 | 550 |
| 126 | 2,4 | 4-t-Bu | 4.990 | 504 |
| 127 | 2,4 | 3-Cl | 4.247 | 460 |
| 128 | 2,4 | 3-Br | 4.343 | 550 |
| 129 | 2,4 | 3-Me | 4.194 | 420 |
| 130 | 2,4 | 3-CF3 | 4.297 | 528 |
| 131 | 2,4 | 3,4-diF | 4.005 | 464 |
| 132 | 2,3 | 4-Br | 4.325 | 550 |
| 133 | 2,3 | 4-F | 3.851 | 428 |
| 134 | 2,3 | 4-CF3 | 4.285 | 528 |
| 135 | 2,3 | 4-t-Bu | 4.917 | 504 |
| 136 | 2,3 | 3-Cl | 4.188 | 460 |
| 137 | 2,3 | 3-Br | 4.284 | 550 |
| 138 | 2,3 | 3-Me | 4.138 | 420 |
| 139 | 2,3 | 3-CF3 | 4.221 | 528 |
| 140 | 2,3 | 4-Me | 4.128 | 420 |
| 141 | 2,3 | 3,4-diF | 3.937 | 464 |
| 142 | 3,5 | 3-Cl | 4.303 | 460 |
| 143 | 3,5 | 4-F | 3.945 | 428 |
| 144 | 3,5 | 4-CF3 | 4.389 | 528 |
| 145 | 3,5 | 4-Br | 4.426 | 550 |
| 146 | 3,5 | 4-t-Bu | 4.999 | 504 |
| 147 | 3,5 | 3-Br | 4.401 | 550 |
| 148 | 3,5 | 3-Me | 4.214 | 420 |
| 149 | 3,5 | 3-CF3 | 4.339 | 528 |
| 150 | 3,5 | 4-Me | 4.219 | 420 |
| 151 | 3,5 | 3,4-diF | 4.017 | 464 |
| 152 | 2,5 | 3-CF3 | 4.308 | 528 |
| 153 | 2,5 | 4-F | 3.922 | 428 |
| 154 | 2,5 | 4-CF3 | 4.361 | 528 |
| 155 | 2,5 | 4-Br | 4.368 | 550 |
| 156 | 2,5 | 4-t-Bu | 4.99 | 504 |
| 157 | 2,5 | 3-Cl | 4.249 | 460 |
| 158 | 2,5 | 3-Br | 4.340 | 550 |
| 159 | 2,5 | 3-Me | 4.195 | 420 |
| 160 | 2,5 | 4-Me | 4.201 | 420 |
| 161 | 2,5 | 3,4-diF | 4.058 | 464 |

Example 179

Representative Substituted Acetylenic Oximeacetic Acid Derivatives

TABLE 8

R—≡—X—CH=N—O—CH2—COOH

| Compound | R | X | LC @ 254 (min) | MS (M + H) |
|---|---|---|---|---|
| {[((1E)-{4-[3-(4-tert-butylphenoxy)prop-1-ynyl]phenyl}methylidene)amino]oxy}acetic acid. | 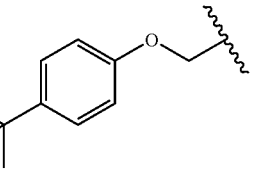 | 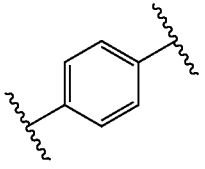 | 3.793 | 366 |
| {[((1E)-{4-[3-(4-bromophenoxy)prop-1-ynyl]phenyl}methylidene)amino]oxy}acetic acid | 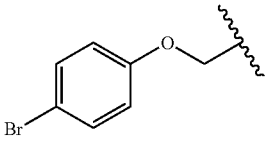 | 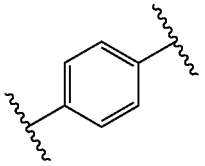 | 3.422 | 388, 390 |
| ({[((1E)-(4-{3-(3,5-bis(trifluoromethyl)phenoxy]prop-1-ynyl}phenyl)methylidene]amino}oxy)acetic acid. | 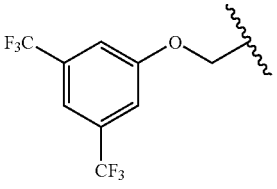 | 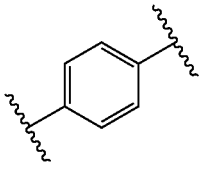 | 3.754 | 446 |
| Synthesis of {[((1E)-{4-[3-(3,5-dichlorophenoxy)prop-1-ynyl]phenyl}methylidene)amino]oxy}acetic acid | 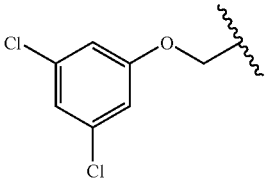 | 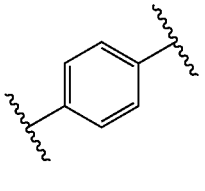 | 3.710 | 378, 380 |
| {[((1E)-{4-[3-(3-chlorophenoxy)prop-1-ynyl]phenyl}methylidene)amino]oxy}acetic acid | 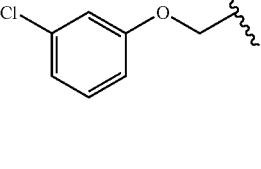 | 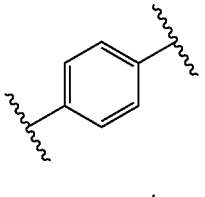 | 3.364 | 344 |
| {[((1E)-{4-[3-(4-isobutylphenoxy)prop-1-ynyl]phenyl}methylidene)amino]oxy}acetic acid | 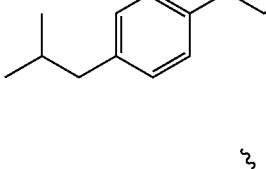 | 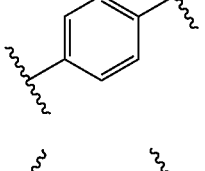 | 3.865 | 366 |
| {[((1E)-{3-[3-(4-tert-butylphenoxy)prop-1-ynyl]phenyl}methylidene)amino]oxy}acetic acid | 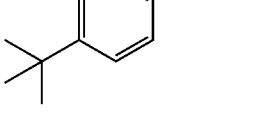 | 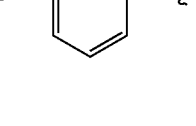 | 3.784 | 388 (M + Na) |

TABLE 8-continued

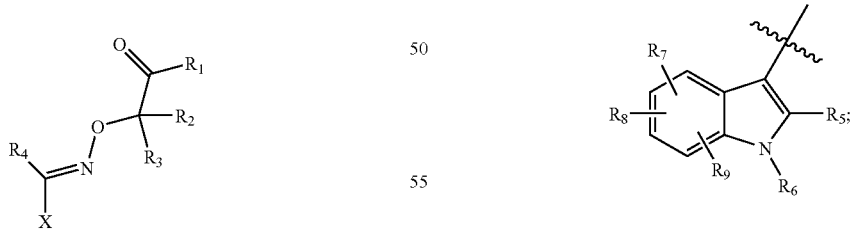

| Compound | R | X | LC @ 254 (min) | MS (M + H) |
|---|---|---|---|---|
| {[((1E)-{3-[3-(4-bromophenoxy)prop-1-ynyl]phenyl}methylidene)amino]oxy}acetic acid | 4-Br-C6H4-O-CH2- | 1,3-phenylene | 3.415 | 388, 390 |
| ({[(1E)-(3-{3-[3,5-bis(trifluoromethyl)phenoxy]prop-1-ynyl}phenyl)methylidene]amino}oxy)acetic acid | 3,5-(CF3)2-C6H3-O-CH2- | 1,3-phenylene | 3.728 | 446 |
| {[((1E)-{3-[3-(3,5-dichlorophenoxy)prop-1-ynyl]phenyl}methylidene)amino]oxy}acetic acid | 3,5-Cl2-C6H3-O-CH2- | 1,3-phenylene | 3.696 | 378, 380 |
| {[((1E)-{3-[3-(3-chlorophenoxy)prop-1-ynyl]phenyl}methylidene)amino]oxy}acetic acid | 3-Cl-C6H4-O-CH2- | 1,3-phenylene | 3.352 | 344 |
| {[((1E)-{3-[3-(4-isobutylphenoxy)prop-1-ynyl]phenyl}methylidene)amino]oxy}acetic acid | 4-iBu-C6H4-O-CH2- | 1,3-phenylene | 3.855 | 366 |

What is claimed:

1. A compound having the formula:

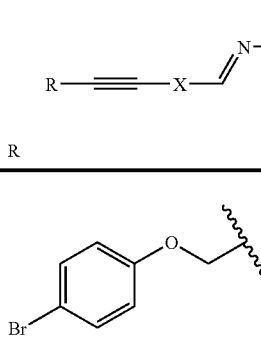

wherein:

R$_1$ is —OH, —OC$_1$-C$_8$ alkyl, or NH$_2$;

R$_2$ and R$_3$ are, independently, hydrogen, C$_1$-C$_8$ alkyl, —CH$_2$—C$_3$-C$_6$ cycloalkyl, —CH$_2$-pyridinyl, phenyl, or benzyl;

R$_4$ is hydrogen, C$_1$-C$_8$ alkyl, C$_3$-C$_6$ cycloalkyl, —CH$_2$—C$_3$-C$_6$ cycloalkyl, phenyl, benzyl, heteroaryl, or —CH$_2$-heteroaryl;

X is

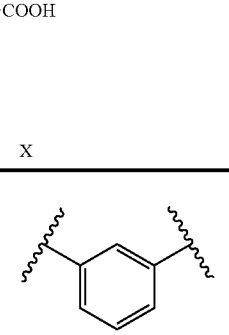

wherein:

R$_5$ is hydrogen, C$_1$-C$_8$ alkyl, C$_3$-C$_6$ cycloalkyl, —CH$_2$—C$_3$-C$_6$ cycloalkyl, phenyl, benzyl, heteroaryl, or —CH$_2$-heteroaryl;

R$_6$ is hydrogen, C$_1$-C$_8$ alkyl, —(CH$_2$)$_n$—CH═CH$_2$, —(CH$_2$)$_n$—CH═CH-alkyl, —(CH$_2$)$_n$C≡CH, —(CH$_2$)$_n$C≡CH-alkyl, aryl, (CH$_2$)$_n$-aryl, heteroaryl, (CH$_2$)$_n$-heteroaryl, —CO-aryl, —CO-heteroaryl, —CO-alkyl, —SO$_2$-alkyl, —SO$_2$-aryl, or —SO$_2$-heteroaryl;

$R_7$ is —O(CH$_2$)$_n$-aryl or —O(CH$_2$)$_n$-heteroaryl;

$R_8$ and $R_9$ are, independently, hydrogen, halogen, $C_1$-$C_6$ alkyl, $C_1$-$C_3$ perfluoroalkyl, —O—$C_1$-$C_3$ perfluoroalkyl, $C_1$-$C_3$ alkoxy, —OH, —NH$_2$ or —NO$_2$; and n is an integer from 0 to 5;

or a pharmaceutically acceptable salt form thereof.

2. The compound of claim 1 wherein $R_4$ is hydrogen, $C_1$-$C_8$ alkyl, $C_3$-$C_6$ cycloalkyl, —CH$_2$—$C_3$-$C_6$ cycloalkyl, phenyl, benzyl, pyridinyl, or —CH$_2$-pyridinyl or a pharmaceutically acceptable salt form thereof.

3. The compound of claim 1 wherein $R_5$ is hydrogen, $C_1$-$C_8$ alkyl, $C_3$-$C_6$ cycloalkyl, —CH$_2$—$C_3$-$C_6$ cycloalkyl, phenyl, benzyl, pyridinyl, or —CH$_2$-pyridinyl or a pharmaceutically acceptable salt form thereof.

4. The compound of claim 1 wherein the rings of the cycloalkyl, pyridinyl, phenyl or benzyl groups are optionally substituted by 1 to 3 groups selected from halogen, $C_1$-$C_3$ alkyl, $C_1$-$C_3$ perfluoroalkyl, —O—$C_1$-$C_3$ perfluoroalkyl, $C_1$-$C_3$ alkoxy, —OH, —NH$_2$, —CN, or —NO$_2$ or a pharmaceutically acceptable salt form thereof.

5. A compound having the formula:

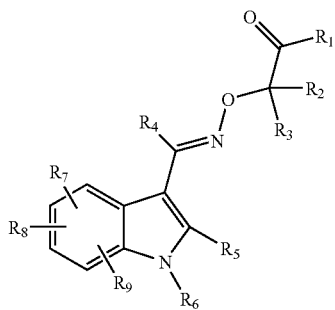

wherein:

$R_1$ is —OH, —OC$_1$-$C_8$ alkyl, or NH$_2$;

$R_2$ and $R_3$ are, independently, hydrogen, $C_1$-$C_8$ alkyl, —CH$_2$—$C_3$-$C_6$ cycloalkyl, —CH$_2$-pyridinyl, phenyl, or benzyl;

$R_4$ is hydrogen, $C_1$-$C_8$ alkyl, $C_3$-$C_6$ cycloalkyl, —CH$_2$—$C_3$-$C_6$ cycloalkyl, phenyl, benzyl, heteroaryl, or —CH$_2$-heteoaryl;

$R_5$ is hydrogen, $C_1$-$C_8$ alkyl, $C_3$-$C_6$ cycloalkyl, —CH$_2$—$C_3$-$C_6$ cycloalkyl, phenyl, benzyl, heteroaryl, or —CH$_2$-heteroaryl;

$R_6$ is hydrogen, $C_1$-$C_8$ alkyl, —(CH$_2$)$_n$—CH=CH$_2$, —(CH$_2$)$_n$—CH=CH-alkyl, —(CH$_2$)$_n$C≡CH, —(CH$_2$)$_n$C≡CH-alkyl, aryl, (CH$_2$)$_n$-aryl, heteroaryl, (CH$_2$)$_n$-heteroaryl, —CO-aryl, —CO-heteroaryl, —CO-alkyl, —SO$_2$-alkyl, —SO$_2$-aryl, or —SO$_2$-heteroaryl;

$R_7$ is —O(CH$_2$)$_n$-aryl or —O(CH$_2$)$_n$-heteroaryl;

$R_8$ and $R_9$ are, independently, hydrogen, halogen, $C_1$-$C_6$ alkyl, $C_1$-$C_3$ perfluoroalkyl, —O—$C_1$-$C_3$ perfluoroalkyl, $C_1$-$C_3$ alkoxy, —OH, —NH$_2$ or —NO$_2$, and n is an integer from 0 to 5;

or a pharmaceutically acceptable salt or ester form thereof.

6. The compound of claim 5 having the formula:

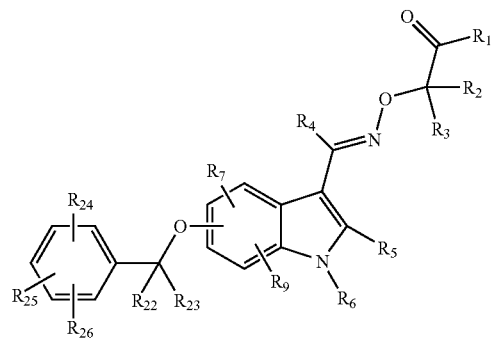

or a pharmaceutically acceptable salt or ester from thereof, wherein:

$R_{22}$ and $R_{23}$ are, each hydrogen; and $R_{24}$, $R_{25}$ and $R_{26}$ are, independently, hydrogen, halogen, $C_1$-$C_6$ alkyl, $C_1$-$C_3$ perfluoroalkyl, —O—$C_1$-$C_3$ perfluoroalkyl, $C_1$-$C_6$ alkoxy, —OH, —NH$_2$, —NO$_2$, —O(CH$_2$)$_n$-aryl, —O(CH$_2$)$_n$-heteroaryl, aryl, or heteroaryl.

7. The compound of claim 6 wherein $R_{24}$, $R_{25}$ and $R_{26}$ are, independently, hydrogen, halogen, $C_1$-$C_3$ alkyl, $C_1$-$C_3$ perfluoroalkyl, —O—$C_1$-$C_3$ perfluoroalkyl, $C_1$-$C_3$ alkoxy, —OH, —NH$_2$, or —NO$_2$, —O(CH$_2$)$_n$-aryl, —O(CH$_2$)$_n$-heteroaryl, aryl, or heteroaryl or a pharmaceutically acceptable salt form thereof.

8. The compound of claim 6 wherein $R_1$ is —OH;

$R_2$, $R_3$, $R_4$, $R_5$, $R_8$, $R_9$, $R_{22}$, $R_{23}$, $R_{24}$, and $R_{25}$ are independently hydrogen;

$R_6$ is $C_1$-$C_8$ alkyl, —(CH$_2$)$_n$—CH=CH$_2$, —(CH$_2$)$_n$—CH=CH-alkyl, —(CH$_2$)$_n$C≡CH, —(CH$_2$)$_n$C≡C-alkyl or (CH$_2$)$_n$-aryl;

$R_{26}$ is halogen, $C_1$-$C_6$ alkyl, $C_1$-$C_3$ perfluoroalkyl, $C_1$-$C_6$ alkoxy, or naphthyl or a pharmaceutically acceptable salt form thereof.

9. The compound of claim 5 selected from the group consisting of

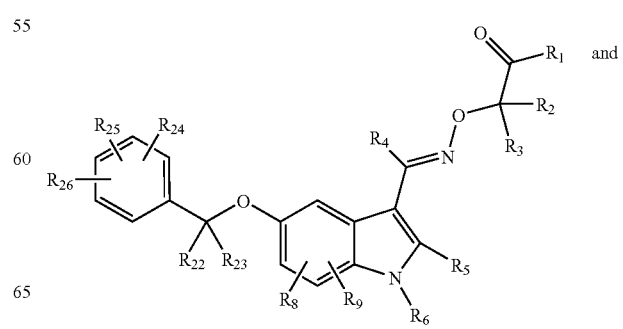

and

-continued

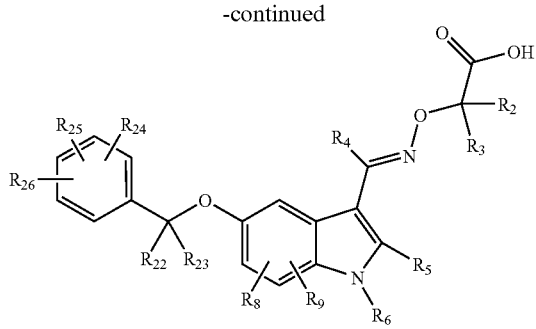

or a pharmaceutically acceptable salt or ester form thereof.

10. The compound of claim 5 that is ({[((1E)-(1-allyl-5-{[4-(trifluoromethyl)benzyl]oxy}-1H-indol-3-yl)methylidene]amino}oxy)acetic acid, ({[((1E)-(1-ethyl-5-{[4-(trifluoromethyl)benzyl]oxy}-1H-indol-3-yl)methylidene]amino}oxy)acetic acid, ({[((1E)-(1-benzyl-5-{[4-(trifluoromethyl)benzyl]oxy}-1H-indol-3-yl)methylidene]amino}oxy)acetic acid, {[((1E)-{1-allyl-5-[(4-tert-butylbenzyl)oxy]-1H-indol-3-yl}methylidene)amino]oxy}acetic acid, {[((1E)-{5-[(4-tert-butylbenzyl)oxy]-1-ethyl-1H-indol-3-yl}methylidene)amino]oxy}acetic acid or a pharmaceutically acceptable salt or ester form thereof.

11. The compound of claim 5 that is {[((1E)-{1-benzyl-5-[(4-tert-butyl benzyl)oxy]-1H-indol-3-yl}methylidene)amino]oxy}acetic acid, {[((1E)-{1-allyl-5-[(4-bromobenzyl)oxy]-1H-indol-3-yl}methylidene)amino]oxy}acetic acid, {[((1E)-{5-[(4-bromobenzyl)oxy]-1-ethyl-1H-indol-3-yl}methylidene)amino]oxy}acetic acid, {[((1E)-{1-benzyl-5-[(4-bromobenzyl)oxy]-1H-indol-3-yl}methylidene)amino]oxy}acetic acid, ({[((1E)-(1-allyl-5-{[3,5-bis(trifluoromethyl)benzyl]oxy}-1H-indol-3-yl)methylidene]amino}oxy)acetic acid, ({[((1E)-(5-{[3,5-bis(trifluoromethyl)benzyl]oxy}-1-ethyl-1H-indol-3-yl)methylidene]amino}oxy)acetic acid, ({[((1E)-(1-benzyl-5-{[3,5-bis(trifluoromethyl)benzyl]oxy}-1H-indol-3-yl)methylidene]amino}oxy)acetic acid, {[((1E)-{1-allyl-5-[(3-bromobenzyl)oxy]-1H-indol-3-yl}methylidene)amino]oxy}acetic acid, {[((1E)-{5-[(3-bromobenzyl)oxy]-1-ethyl-1H-indol-3-yl}methylidene)amino]oxy}acetic acid, {[((1E)-{1-benzyl-5-[(3-bromobenzyl)oxy]-1H-indol-3-yl}methylidene)amino]oxy}acetic acid or a pharmaceutically acceptable salt or ester form thereof.

12. The compound of claim 5 that is {[((1E)-{1-allyl-5-[(3-chlorobenzyl)oxy]-1H-indol-3-yl}methylidene)amino]oxy}acetic acid, {[((1E)-{5-[(3-chlorobenzyl)oxy]-1-ethyl-1H-indol-3-yl}methylidene)amino]oxy}acetic acid, {[((1E)-{1-benzyl-5-[(3-chlorobenzyl)oxy]-1H-indol-3-yl}methylidene)amino]oxy}acetic acid, {[((1E)-{1-allyl-5-[(4-methylbenzyl)oxy]-1H-indol-3-yl}methylidene)amino]oxy}acetic acid, {[((1E)-{1-ethyl-5-[(4-methylbenzyl)oxy]-1H-indol-3-yl}methylidene)amino]oxy}acetic acid, {[((1E)-{1-benzyl-5-[(4-methylbenzyl)oxy]-1H-indol-3-yl}methylidene)amino]oxy}acetic acid, ({[((1E)-(1-allyl-5-{[3-(trifluoromethyl)benzyl]oxy}-1H-indol-3-yl)methylidene]amino}oxy)acetic acid, ({[((1E)-(1-ethyl-5-{[3-(trifluoromethyl)benzyl]oxy}-1H-indol-3-yl)methylidene]amino}oxy)acetic acid, ({[((1E)-(1-benzyl-5-{[3-(trifluoromethyl)benzyl]oxy}-1H-indol-3-yl)methylidene]amino}oxy)acetic acid, {[((1E)-{1-allyl-5-[(3-methylbenzyl)oxy]-1H-indol-3-yl}methylidene)amino]oxy}acetic acid or a pharmaceutically acceptable salt or ester form thereof.

13. The compound of claim 5 that is {[((1E)-{1-ethyl-5-[(3-methylbenzyl)oxy]-1H-indol-3-yl}methylidene)amino]oxy}acetic acid, {[((1E)-{1-benzyl-5-[(3-methylbenzyl)oxy]-1H-indol-3-yl}methylidene)amino]oxy}acetic acid, {[((1E)-{5-[(2-chlorobenzyl)oxy]-1-ethyl-1H-indol-3-yl}methylidene)amino]oxy}acetic acid, {[((1E)-{1-benzyl-5-[(2-chlorobenzyl)oxy]-1H-indol-3-yl}methylidene)amino]oxy}acetic acid, {[((1E)-{5-[(2-chlorobenzyl)oxy]-1H-indol-3-yl}methylidene)amino]oxy}acetic acid, ({[((1E)-(1-(2-propynyl)-5-{[4-(trifluoromethyl)benzyl]oxy}-1H-indol-3-yl)methylidene]amino}oxy)acetic acid, ({[((1E)-(1-methyl-5-{[4-(trifluoromethyl)benzyl]oxy}-1H-indol-3-yl)methylidene]amino}oxy)acetic acid, [({(1E)-[5-[(4-tert-butylbenzyl)oxy]-1-(2-propynyl)-1H-indol-3-yl]methylidene}amino)oxy]acetic acid, {[((1E)-{5-[(4-tert-butylbenzyl)oxy]-1-methyl-1H-indol-3-yl}methylidene)amino]oxy}acetic acid, [({(1E)-[5-{[3,5-bis(trifluoromethyl)benzyl]oxy}-1-(2-propynyl)-1H-indol-3-yl]methylidene}amino)oxy]acetic acid or a pharmaceutically acceptable salt or ester form thereof.

14. The compound of claim 5 that is [({(1E)-[5-[(3-bromobenzyl)oxy]-1-(2-propynyl)-1H-indol-3-yl]methylidene}amino)oxy]acetic acid, {[((1E)-{5-[(3-bromobenzyl)oxy]-1-methyl-1H-indol-3-yl}methylidene)amino]oxy}acetic acid, [({(1E)-[5-[(3-chlorobenzyl)oxy]-1-(2-propynyl)-1H-indol-3-yl]methylidene}amino)oxy]acetic acid, {[((1E)-{5-[(3-chlorobenzyl)oxy]-1-methyl-1H-indol-3-yl}methylidene)amino]oxy}acetic acid, [({(1E)-[1-allyl-5-(benzyloxy)-1H-indol-3-yl]methylidene}amino)oxy]acetic acid, [({(1E)-[1-benzyl-5-(benzyloxy)-1H-indol-3-yl]methylidene}amino)oxy]acetic acid, ({[((1E)-(1-(2-propynyl)-5-{[3-(trifluoromethyl)benzyl]oxy}-1H-indol-3-yl)methylidene]amino}oxy)acetic acid, ({[((1E)-(1-methyl-5-{[3-(trifluoromethyl)benzyl]oxy}-1H-indol-3-yl)methylidene]amino}oxy)acetic acid, [({(1E)-[5-[(4-chlorobenzyl)oxy]-1-(2-propynyl)-1H-indol-3-yl]methylidene}amino)oxy]acetic acid, {[((1E)-{1-allyl-5-[(4-chlorobenzyl)oxy]-1H-indol-3-yl}methylidene)amino]oxy}acetic acid or a pharmaceutically acceptable salt or ester form thereof.

15. The compound of claim 5 that is {[((1E)-{1-benzyl-5-[(4-chlorobenzyl)oxy]-1H-indol-3-yl}methylidene)amino]oxy}acetic acid, {[((1E)-{5-[(4-chlorobenzyl)oxy]-1-methyl-1H-indol-3-yl}methylidene)amino]oxy}acetic acid, [({(1E)-[5-[(2-chloro benzyl)oxy]-1-(2-propynyl)-1H-indol-3-yl]methylidene}amino)oxy]acetic acid, {[((1E)-{1-allyl-5-[(2-chlorobenzyl)oxy]-1H-indol-3-yl}methylidene)amino]oxy}acetic acid, {[((1E)-{5-[(2-chlorobenzyl)oxy]-1-methyl-1H-indol-3-yl}methylidene)amino]oxy}acetic acid, [({(1E)-[5-[(3,4-dichlorobenzyl)oxy]-1-(2-propynyl)-1H-indol-3-yl]methylidene}amino)oxy]acetic acid, {[((1E)-{1-allyl-5-[(3,4-dichlorobenzyl)oxy]-1H-indol-3-yl}methylidene)amino]oxy}acetic acid, {[((1E)-{1-benzyl-5-[(3,4-dichlorobenzyl)oxy]-1H-indol-3-yl}methylidene)amino]oxy}acetic acid, {[((1E)-{5-[(3,4-dichlorobenzyl)oxy]-1-methyl-1H-indol-3-yl}methylidene)amino]oxy}acetic acid, [({(1E)-[1-allyl-5-(2-naphthylmethoxy)-1H-indol-3-yl]methylidene}amino)oxy]acetic acid, [({(1E)-[1-benzyl-5-(2-naphthylmethoxy)-1H-indol-3-yl]methylidene}amino)oxy]acetic acid, [({(1E)-[1-methyl-5-(2-naphthylmethoxy)-1H-indol-3-yl]methylidene}amino)oxy]acetic acid or a pharmaceutically acceptable salt or ester form thereof.

16. A pharmaceutical composition comprising a therapeutically effective amount of a compound of claim 1, or a pharmaceutically acceptable salt or ester form thereof, and a pharmaceutically acceptable excipient or carrier.

* * * * *